United States Patent
Muthuppalaniappan et al.

(10) Patent No.: US 9,758,474 B2
(45) Date of Patent: *Sep. 12, 2017

(54) IMMUNOMODULATOR AND ANTI-INFLAMMATORY COMPOUNDS

(71) Applicants: Rhizen Pharmaceuticals SA, La Chaux-de-Fonds (CH); Incozen Therapeutics Pvt. Ltd., Hyderabad (IN)

(72) Inventors: Meyyappan Muthuppalaniappan, Hyderabad (IN); Prashant K. Bhavar, Hyderabad (IN); Srikant Viswanadha, Hyderabad (IN); Swaroop K. Vakkalanka, Hyderabad (IN); Gayatri S. Merikapudi, Hyderabad (IN)

(73) Assignees: INCOZEN THERAPEUTICS PVT. LTD., Hyderabad (IN); RHIZEN PHARMACEUTICALS SA, La Chaux-de-Fonds (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/172,707

(22) Filed: Feb. 4, 2014

(65) Prior Publication Data
US 2014/0220050 A1 Aug. 7, 2014

Related U.S. Application Data

(63) Continuation of application No. 13/101,921, filed on May 5, 2011, now Pat. No. 8,686,048.

(30) Foreign Application Priority Data

May 6, 2010 (IN) ............................ 1265/CHE/2010

(51) Int. Cl.
| | |
|---|---|
| A01N 37/18 | (2006.01) |
| A01N 43/40 | (2006.01) |
| A01N 43/32 | (2006.01) |
| A01N 43/38 | (2006.01) |
| A61K 31/50 | (2006.01) |
| C07D 211/72 | (2006.01) |
| C07C 233/00 | (2006.01) |
| C12N 5/00 | (2006.01) |
| C07C 235/56 | (2006.01) |
| C07C 233/65 | (2006.01) |
| C07C 233/66 | (2006.01) |
| C07C 233/75 | (2006.01) |
| C07C 309/59 | (2006.01) |
| C07C 317/32 | (2006.01) |
| C07C 323/42 | (2006.01) |
| C07D 209/14 | (2006.01) |
| C07D 213/75 | (2006.01) |
| C07D 213/81 | (2006.01) |
| C07D 231/56 | (2006.01) |
| C07D 241/24 | (2006.01) |
| C07D 307/79 | (2006.01) |
| C07D 317/58 | (2006.01) |
| C07D 319/18 | (2006.01) |
| A61K 31/167 | (2006.01) |
| A61K 31/185 | (2006.01) |

(Continued)

(52) U.S. Cl.
CPC .......... *C07C 235/56* (2013.01); *A61K 31/167* (2013.01); *A61K 31/185* (2013.01); *A61K 31/196* (2013.01); *A61K 31/343* (2013.01); *A61K 31/357* (2013.01); *A61K 31/405* (2013.01); *A61K 31/416* (2013.01); *A61K 31/44* (2013.01); *A61K 45/06* (2013.01); *C07C 233/65* (2013.01); *C07C 233/66* (2013.01); *C07C 233/75* (2013.01); *C07C 235/84* (2013.01); *C07C 309/52* (2013.01); *C07C 309/59* (2013.01); *C07C 317/32* (2013.01); *C07C 323/42* (2013.01); *C07D 209/14* (2013.01); *C07D 213/75* (2013.01); *C07D 213/81* (2013.01); *C07D 231/56* (2013.01); *C07D 241/24* (2013.01); *C07D 307/79* (2013.01); *C07D 317/58* (2013.01); *C07D 319/18* (2013.01); *C07C 2101/02* (2013.01); *C07C 2101/08* (2013.01)

(58) Field of Classification Search
None
See application file for complete search history.

(56) References Cited

U.S. PATENT DOCUMENTS 2,474,893 A  7/1949  Friedman et al.
4,710,515 A * 12/1987 Kirk ..................... A61K 31/195
                                                          514/535

(Continued)

FOREIGN PATENT DOCUMENTS

DE  887501 C   8/1953
EP  767167 A1  4/1997

(Continued)

OTHER PUBLICATIONS

Hartmann R W et al: "Synthesis and Aromatase Inhibition of 3-Cycloalkyl-Substituted 3-(4-Aminophenyl)Piperidine-2,6-Diones", Journal of Medicinal Chemistry, American Chemical Society , US, vol. 35 , No. 12 , Jun. 12, 1992 (Jun. 12, 1992), pp. 2210-2214.

(Continued)

*Primary Examiner* — Bong-Sook Baek
(74) *Attorney, Agent, or Firm* — Blank Rome LLP

(57) ABSTRACT

The present invention provides dihydroorotate dehydrogenase inhibitors, methods of preparing them, pharmaceutical compositions containing them and methods of treatment, prevention and/or amelioration of diseases or disorders wherein the inhibition of Dihydroorotate dehydrogenase is known to show beneficial effect.

8 Claims, No Drawings

(51) Int. Cl.
*A61K 31/196* (2006.01)
*A61K 31/343* (2006.01)
*A61K 31/357* (2006.01)
*A61K 31/405* (2006.01)
*A61K 31/416* (2006.01)
*A61K 31/44* (2006.01)
*A61K 45/06* (2006.01)
*C07C 235/84* (2006.01)
*C07C 309/52* (2006.01)

(56) References Cited

U.S. PATENT DOCUMENTS

| | | | |
|---|---|---|---|
| 5,976,848 | A | 11/1999 | Davis et al. |
| 6,841,561 | B1 | 1/2005 | Tan et al. |
| 7,074,831 | B2 | 7/2006 | Jonsson et al. |
| 7,176,241 | B2 | 2/2007 | Leban et al. |
| 7,247,736 | B2 | 7/2007 | Leban et al. |
| 7,423,057 | B2 | 9/2008 | Leban et al. |
| 2003/0073862 | A1 | 4/2003 | Gustavsson et al. |
| 2003/0203951 | A1 | 10/2003 | Leban et al. |
| 2004/0176337 | A1 | 9/2004 | Saoji et al. |
| 2006/0199856 | A1 | 9/2006 | Leban et al. |
| 2007/0027193 | A1 | 2/2007 | Leban et al. |
| 2007/0224672 | A1 | 9/2007 | Leban et al. |
| 2007/0299114 | A1 | 12/2007 | Kugimiya et al. |
| 2008/0027079 | A1 | 1/2008 | Phillips et al. |
| 2009/0062318 | A1 | 3/2009 | Gangjee |
| 2009/0082374 | A1 | 3/2009 | Gangjee |
| 2009/0209557 | A1 | 8/2009 | Phillips et al. |

FOREIGN PATENT DOCUMENTS

| | | | |
|---|---|---|---|
| EP | 2135610 | A1 | 12/2009 |
| WO | WO-9734600 | A1 | 9/1997 |
| WO | WO-9938846 | A1 | 8/1999 |
| WO | WO-9941239 | A1 | 8/1999 |
| WO | WO-9945926 | A1 | 9/1999 |
| WO | WO-0124785 | A2 | 4/2001 |
| WO | WO-02080897 | A1 | 10/2002 |
| WO | WO-03006424 | A1 | 1/2003 |
| WO | WO-03006425 | A2 | 1/2003 |
| WO | WO-03030905 | A1 | 4/2003 |
| WO | WO-03097574 | A2 | 11/2003 |
| WO | WO-2004056746 | A1 | 7/2004 |
| WO | WO-2004056747 | A1 | 7/2004 |
| WO | WO-2004056797 | A1 | 7/2004 |
| WO | WO-2005075410 | A1 | 8/2005 |
| WO | WO-2006001961 | A2 | 1/2006 |
| WO | WO-2006022442 | A1 | 3/2006 |
| WO | WO-2006038606 | A1 | 4/2006 |
| WO | WO-2006044741 | A1 | 4/2006 |
| WO | WO-2006051937 | A2 | 5/2006 |
| WO | WO-2007149211 | A1 | 12/2007 |
| WO | WO-2008077639 | A1 | 7/2008 |
| WO | WO-2008097180 | A1 | 8/2008 |
| WO | WO-2009021696 | A1 | 2/2009 |
| WO | WO-2009029473 | A1 | 3/2009 |
| WO | WO-2009082691 | A1 | 7/2009 |
| WO | WO-2009133379 | A2 | 11/2009 |
| WO | WO-2009137081 | A2 | 11/2009 |
| WO | WO-2009153043 | A1 | 12/2009 |
| WO | WO-2011026107 | A1 | 3/2011 |

OTHER PUBLICATIONS

John S. Swenton et al: "Preparation of quinol N-acyl- and quinol ether imines via anodic oxidation of para-substituted anilide derivatives", The Journal of Organic Chemistry, vol. 58, No. 21, Oct. 1, 1993 (Oct. 1, 1993), pp. 5607-5614.

Ruschig H et al : "2,6-Dihyoroxybenzoesaeurederivate Als Anthelminthika//2,6-Dihydroxybe Nzoic Acid Derivatives as Anthelimintics", Arzneimittel Forschung. Drug Research, ECV Editio Cantor Verlag, Aulendorf, DE, vol. 23, No. 12, Jan. 1, 1973 (Jan. 1, 1973), pp. 1745-1758.

Serchenkova S V et al: "IR spectroscopic study of compounds of benzimide-amido-acid series", Polymer Science U.S .S.R, Pergamon , vol. 18 , No. 8, Jan. 1, 1976 (Jan. 1, 1976) , pp. 2133-2141.

International Search Report issued in connection with PCT/IB2011/000959 on Aug. 30, 2011.

Shinji Ando et al: "Substituent shielding parameters of fluorine-19 NMR on polyfluoroaromatic compounds dissolved in dimethyl sulphoxide-d6", Magnetic Resonance in Chemistry , vol. 33, No. 8, Aug. 1, 1995 (Aug. 1, 1995), pp. 639-645.

* cited by examiner

IMMUNOMODULATOR AND ANTI-INFLAMMATORY COMPOUNDS

This application is a continuation of U.S. patent application Ser. No. 13/101,921, filed May 5, 2011, which claims the benefit of Indian Provisional Patent Application No. 1265/CHE/2010 dated 6$^{th}$ May 2010, each of which is hereby incorporated by reference.

FIELD OF THE INVENTION

The present invention provides dihydroorotate dehydrogenase inhibitors, methods of preparing them, pharmaceutical compositions containing them and methods of treatment, prevention and/or amelioration of diseases or disorders wherein the inhibition of Dihydroorotate dehydrogenase is known to show beneficial effect.

BACKGROUND OF THE INVENTION

In the recent past immense research has been dedicated to the discovery and understanding of the structure and functions of enzymes and bio-molecules associated with various diseases. One such important class of enzymes that has been the subject of extensive research is dihydroorotate dehydrogenase (DHODH).

DHODH is an enzyme that catalyzes the fourth step in the de novo biosynthesis of pyrimidine. It converts dihydroorotate (DHO) to orotate (ORO). Human DHODH is a ubiquitous flavine mononucleotide (FMN) moiety flavoprotein. In bacteria (gene pyrD), it is located on the inner side of the cytosolic membrane. In some yeasts, such as in *Saccharomyces cerevisiae* (gene URA1), it is a cytosolic protein while in other eukaryotes it is found in the mitochondria (see Proc. Natl. Acad. Sci. U.S.A., 89 (19), 8966-8970).

DHODH has been classified as a family of class I or class II proteins on the basis of the cofactor. Human DHODH belongs to the family class 2 that utilizes flavine as a redox cofactor, unlike the bacterial family class 1 protein that uses fumarate or NAD+ instead. In the cell the mammalian protein is anchored at the inner mitochondrial leaflet. There, DHODH catalyzes the conversion of DHO to ORO, which represents the rate limiting step in the de novo pyrimidine biosynthesis. (see McLean et al., Biochemistry 2001, 40, 2194-2200). Kinetic studies indicate a sequential ping-pong mechanism for the conversion of DHO to ORO (see Knecht et al., Chem. Biol. Interact. 2000, 124, 61-76). The first half-reaction comprises the reduction of DHO to ORO. Electrons are transferred to the FMN which becomes oxidized to dihydroflavin mononucleotide (FMNH2). After dissociation of ORO from the enzyme, FMNH2 is regenerated by a ubiquinone molecule, which is recruited from the inner mitochondrial membrane. Kinetic and structural studies revealed two distinct binding sites for DHO/ORO and ubiquinone, respectively.

Human DHODH is composed of two domains, a large C-terminal domain (Met78-Arg396) and a smaller N-terminal domain (Met30-Leu68), connected by an extended loop. The large C-terminal domain can be best described as an α/β-barrel fold with a central barrel of eight parallel β strands surrounded by eight α helices. The redox site, formed by the substrate binding pocket and the site that binds the cofactor FMN, is located on this large C-terminal domain. The small N-terminal domain, on the other hand, consists of two α helices (labeled α1 and α2), both connected by a short loop. This small N-terminal domain harbors the binding site for the cofactor ubiquinone. The helices α1 and α2 span a slot of about 10×20 Å$^2$ in the so-called hydrophobic patch, with the short α1-α2 loop at the narrow end of that slot. The slot forms the entrance to a tunnel that ends at the FMN cavity nearby the α1-α2 loop. This tunnel narrows toward the proximal redox site and ends with several charged or polar side chains (Gln47, Tyr356, Thr360, and Arg136). Structural clues, as discussed above, along with kinetic studies suggest that ubiquinone, which can easily diffuse into the mitochondrial inner membrane, uses this tunnel to approach the FMN cofactor for the redox reaction (see Baumgartner et al., J. Med. Chem. 2006, 49, 1239-1247).

A study disclosed in The Journal of Biological Chemistry 2005, 280(23), 21847-21853; formally demonstrates the possibility to identify potent inhibitors of *P. falciparum* DHODH that do not inhibit the human enzyme. Comparison of the human DHODH crystal structures with the malaria DHODH amino acid sequence further suggests there are opportunities for species-specific inhibitor binding.

In the body, DHODH catalyzes the synthesis of pyrimidines, which are necessary for cell growth. An inhibition of DHODH inhibits the growth of (pathologically) fast proliferating cells, whereas cells which grow at normal speed may obtain their required pyrimidine bases from the normal metabolic cycle. The most important types of cells for the immune response, the lymphocytes, use exclusively the synthesis of pyrimidines for their growth and react particularly sensitively to DHODH inhibition.

DHODH inhibition results in decreased cellular levels of ribonucleotide uridine monophosphate (rUMP), thus arresting proliferating cells in the G1 phase of the cell cycle. The inhibition of de novo pyrimidine nucleotide synthesis is of great interest in view of the observations that lymphocytes seem not to be able to undergo clonal expansion when this pathway is blocked. Substances that inhibit the growth of lymphocytes are important medicaments for the treatment of auto-immune diseases.

During homeostatic proliferation, the salvage pathway which is independent of DHODH seems sufficient for the cellular supply with pyrimidine bases. Only, cells with a high turnover and particularly T and B lymphocytes need the de novo pathway to proliferate. In these cells, DHODH inhibition stops the cell cycle progression suppressing DNA synthesis and consequently cell proliferation (see Breedveld et al., Ann Rheum Dis 2000).

Therefore, inhibitors of DHODH show beneficial immunosuppressant and antiproliferative effects in human diseases characterized by abnormal and uncontrollable cell proliferation causing chronic inflammation and tissue destruction. The human enzyme dihydroorotate dehydrogenase (DHODH) represents a well-characterized target for small molecular weight Disease Modifying Antirheumatic Drugs (DMARDs).

A list of known DHODH inhibitors includes Leflunomide, Teriflunomide, Brequinar (NSC 368390) (Cancer Research 1992, 52, 3521-3527), Dichloroallyl lawsone (The Journal of Biological Chemistry 1986, 261(32), 14891-14895), Maritimus (FK 778) (Drugs of the Future 2002, 27(8), 733-739) and Redoxal (The Journal of Biological Chemistry 2002, 277(44), 41827-41834),

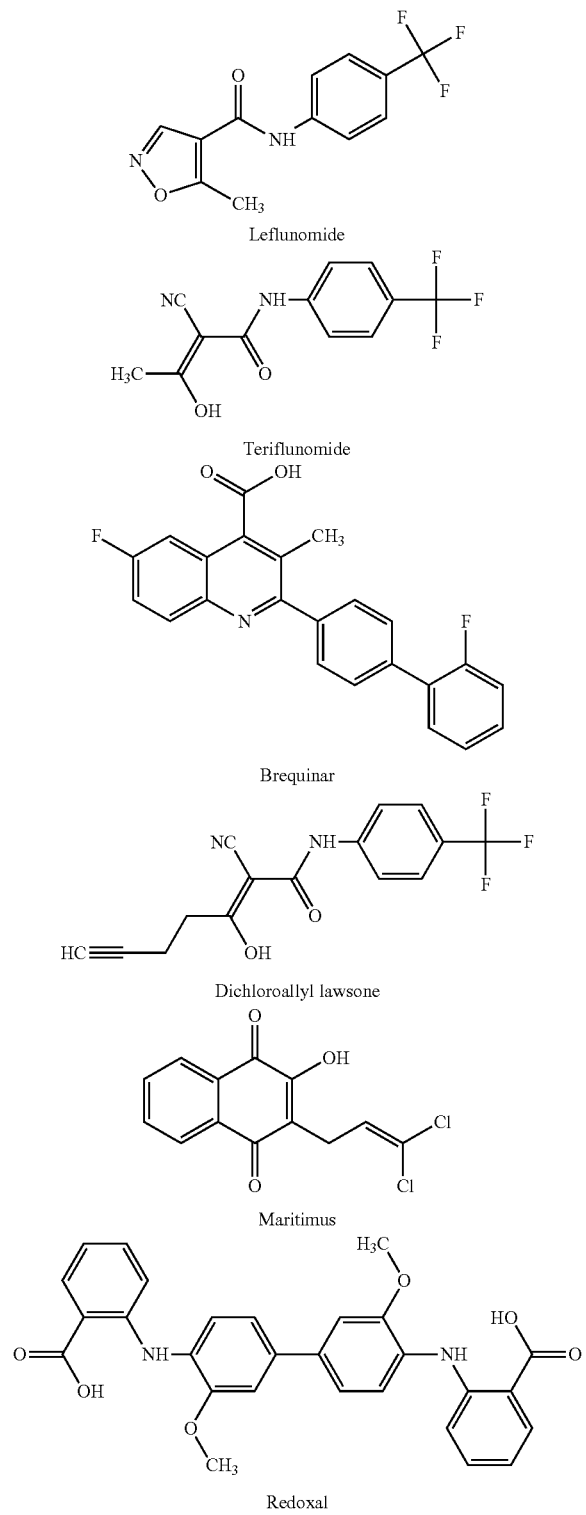

Leflunomide, teriflunomide, and brequinar have been studied significantly.

In general, inhibitors of DHODH show beneficial immunosuppressive and antiproliferative activities, most pronounced on T-cells (see Fairbanks et al., J. Biol. Chem. 1995, 270, 29682-29689). Brequinar and leflunomide are two examples of small molecular weight inhibitors of DHODH that had been in clinical development. The latter is used in the treatment of rheumatoid arthritis refractive to methotrexate (see Rozman J. Rheumatol Suppl. 1998, 53, 27-31; Pally et al., Toxicology 1998, 127, 207-222). Clinical application of both molecules suffers from various side effects. On the basis of very good efficacy in animal models, brequinar was originally developed for the therapy of organ transplant rejection but was switched to cancer as a secondary indication. The compound failed in the clinic due to its narrow therapeutic window. Oral administration of brequinar and some of its analogues resulted in toxic effects, including leukocytopenia and thrombocytopenia, when given in combination with cyclosporine. The application of leflunomide might be flawed by its long half-life time of approximately 2 weeks which represents a serious obstacle in patients that have developed side effects (see Fox et al. J. Rheumatol Suppl. 1998, 53, 20-26; Alldred et al., Expert Opin. Pharmacother. 2001, 2, 125-137).

In addition to abolish lymphocyte proliferation, inhibitors of DHODH (e.g., teriflunomide, maritimus (FK778) and brequinar) have an anti-inflammatory action by inhibition of cytokine production and nuclear factor (NF)-kB-signalling, monocyte migration and increased production of transforming growth factor beta-1 and induce a shift from T helper cell type 1 (TM) to type 2 (Th2) subpopulation differentiation (Manna et al., J. Immunol. 2000; Dimitrova et al., J. Immunol. 2002). Furthermore, the osteoclast differentiation mediated by Receptor Activator for Nuclear Factor k B Ligand (RANKL) decreased by DHODH inhibition (Urushibara et al., Arthrititis Rheum 2004). In co-crystallisation experiments with two inhibitors of DHODH that reached clinical trials, brequinar (Dexter et al., Cancer Res. 1985) and teriflunomide (A77-1726), were both found to bind in a common site, that is also believed to be the binding site of the cofactor ubiquinone (Liu et al., Struc. Fold. Des. 2000).

Leflunomide sold under the trade name Arava (EP 0 780 128, WO 97/34600), was the first DHODH inhibitor that reached the market place. Leflunomide is the prodrug of teriflunomide, which is the active metabolite inhibiting human DHODH with a moderate potency (Fox et al., J. Rheumatol. Suppl. 1998).

Leflunomide is a DMARD from Aventis, which was approved by the FDA for the treatment of rheumatoid arthritis in 1998 and by the EMEA for the treatment of psoriatic arthritis in 2004. Currently leflunomide is under active development for the treatment of systemic lupus erythematosus, Wegener's granulomatosis (Metzler et al., Rheumatology 2004, 43(3), 315-320) and HIV infection. Moreover, teriflunomide, its active metabolite is efficacious in multiple sclerosis and is currently in Phase III clinical trials (O'Connor et al., Neurology 2006).

Other data are emerging in other closely related diseases such as ankylosing spondilitis (Haibel et al., Ann. Rheum. Dis. 2005), polyarticular juvenile idiopathic arthritis (Silverman et al., Arthritis Rheum. 2005) and Sarcoidosis (Baughman et al., Sarcoidosis Vasc. Diffuse Lung Dis. 2004). Furthermore, leflunomide and FK778 have shown antiviral activity against cytomegalovirus. Leflunomide is currently indicated as second-line therapy for cytomegalovirus disease after organ transplantation (John et al., Transplantation 2004). In addition leflunomide reduces HIV replication by about 75% at a concentration that can be obtained with conventional dosing (Schlapfer et al., AIDS 2003).

DHODH inhibitors under investigation at various stages of clinical trials are 4SC-101 (Phase-II) from 4SC AG; LAS-186323 (Phase-I) from Almirall Laboratories SA and ABR-224050, ABR-222417, & ABR-214658 (Preclinical) from Active Biotech AB. The exact structures of all these molecules have not yet been disclosed.

Various DHODH inhibitors have been disclosed for the treatment or prevention of autoimmune diseases, immune and inflammatory diseases, destructive bone disorders, malignant neoplastic diseases, angiogenic-related disorders, viral diseases, and infectious diseases. See for example WO2009137081; WO2009133379; WO 2009021696; WO2009082691; WO2009029473; WO2009153043; US2009209557; US2009 062318; US2009082374; WO2008097180; WO2008077639; US2008027079; US2007 299114; US2007027193; US2007224672; WO2007149211; JP2007015952; WO2006 044741; WO2006001961; WO2006051937; WO2006038606; WO2006022442; US2006 199856; WO2005075410; U.S. Pat. No. 7,074,831; WO2004056797; U.S. Pat. No. 7,247,736; WO2004056747; WO 2004056746; JP2004099586; WO2003097574; WO2003030905; WO2003006425; WO2003 006424; US2003203951; WO2002080897; U.S. Pat. No. 7,176,241; U.S. Pat. No. 7,423,057; WO2001024785; U.S. Pat. No. 6,841,561; WO9945926; WO9938846; WO9941239; EP767167 and U.S. Pat. No. 5,976,848.

For additional reviews and literature regarding DHODH inhibitors see Bio & Med. Chem. Letters, 20(6), 2010, Pages 1981-1984; J. Med. Chem. 2009, 52, 2683-2693; J. Med. Chem. 2008, 51 (12), 3649-3653. All of these patents, patent applications, and literature disclosures are incorporated herein as reference in their entirety for all purposes.

Despite the progress made in the area of DHODH inhibition in human diseases, challenges remain in terms of the side effects and desired clinical benefits from small molecule inhibitors. Accordingly, there still remains an unmet and dire need for small molecule DHODH inhibitors for the treatment and/or amelioration of diseases and disorders known to be associated with DHODH.

SUMMARY OF THE INVENTION

The present invention relates to compounds of formula (I), methods for their preparation, pharmaceutical compositions containing them and methods of use with them. The compound of formula (I) has the structure:

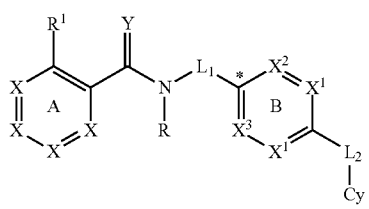

(I)

or a tautomer, stereoisomer (such as an enantiomer or diastereomer), pharmaceutically acceptable salt, pharmaceutically acceptable ester, prodrug or N-oxide thereof, wherein Ring A is independently selected from a substituted or unsubstituted monocyclic aryl and a substituted or unsubstituted monocyclic heteroaryl, wherein each occurrence of X is independently $CR^4$ or N;

Ring B is independently selected from a substituted or unsubstituted monocyclic aryl and a substituted or unsubstituted monocyclic heteroaryl, wherein each occurrence of $X^1$ is independently $CR^4$ or N;

R is hydrogen, substituted or unsubstituted $(C_{1-6})$alkyl or —$OR^a$;

$R^1$ is selected from —OH, —$NR^aOH$, —COOH, —$COOR^a$, —$CR^aR^bOH$, —$CR^aR^bCOOH$, —$SO_2R^a$, —$CR^aR^bSO_2R^a$, —$SO_3R^a$, —$CR^aR^b$—$SO_3R^a$, —C(=Y)—$NR^aR^b$ and —S(=O)$_q$—$NR^aR^b$ or an isostere of —COOH group, such as $SO_3H$, CONHOH, $B(OH)_2$, $PO_3R^aR^b$, $SO_2NR^aR^b$, a tetrazole, an amide, an ester or an acid anhydride or optionally represent halogen, substituted or unsubstituted $(C_{1-6})$alkyl or $Cy^1$;

$X^2$ is N or $CR^2$ and $X^3$ is N or $CR^3$, wherein $R^2$ and $R^3$ may be same or different and are independently selected from hydrogen, halogen, substituted or unsubstituted $(C_{1-6})$alkyl or substituted or unsubstituted $(C_{1-6})$alkoxy.

$L^1$ and $L^2$ are independently absent or selected from —$(CR^aR^b)_n$—, —O—, —S(=O)$_q$—, —$NR^a$—, —C(=Y)—, —C(=Y)—$CR^aR^b$—, —$CR^aR^b$—C(=Y)—, —C(=Y)—C(=Y)—, —$CR^aR^b$—Y—, —C(=Y)—$NR^aR^b$—, —S(=O)$_q$—$NR^aR^b$—, —$NR^aR^b$—C(=Y)—, —$NR^aR^b$—S(=O)$_q$—, substituted or unsubstituted $(C_{1-2})$alkyl, substituted or unsubstituted $(C_2)$alkenyl, and substituted or unsubstituted $(C_2)$alkynyl; optionally each of substituted or unsubstituted $(C_{1-2})$alkyl, substituted or unsubstituted $(C_2)$alkenyl, and substituted or unsubstituted $(C_2)$alkynyl may be interrupted with —O—, —C(=Y)—, —S(=O)$_q$— and —$NR^a$—;

Cy is selected from substituted or unsubstituted cycloalkyl, substituted or unsubstituted heterocyclic group, substituted or unsubstituted aryl and substituted or unsubstituted heteroaryl;

$Cy^1$ is selected from substituted or unsubstituted monocyclic cycloalkyl, substituted or unsubstituted monocyclic heterocyclic group, substituted or unsubstituted monocyclic aryl and substituted or unsubstituted monocyclic heteroaryl;

$R^4$ is independently selected hydrogen, hydroxy, halogen, cyano, —$OR^a$, —S(=O)$_q$—$R^a$, —$NR^aR^b$, —C(=Y)—$R^a$, —C(=Y)—$OR^a$, —C(=Y)—$NR^aR^b$, —S(=O)$_q$—$NR^aR^b$, substituted or unsubstituted alkyl, substituted or unsubstituted alkenyl, substituted or unsubstituted alkynyl, substituted or unsubstituted cycloalkyl, substituted or unsubstituted cycloalkylakyl, substituted or unsubstituted cycloalkenyl or when two $R^4$ substituents are present, they may be joined to a form a substituted or unsubstituted saturated or unsaturated 3-10 member ring, which may optionally include heteroatoms which may be same or different and are selected from O, $NR^a$ or S, or alternatively when two $R^4$ substituent are ortho to each other on an aromatic ring may be joined to form a substituted or unsubstituted saturated or unsaturated 4-10 member ring, which may optionally include one or more heteroatoms which may be same or different and are selected from O, $NR^a$ or S;

each occurrence of $R^a$ and $R^b$ may be the same or different and are independently selected from hydrogen, halogen, hydroxy, cyano, substituted or unsubstituted $(C_{1-6})$alkyl, —$OR^c$ (wherein $R^c$ is substituted or unsubstituted $(C_{1-6})$alkyl) or when $R^a$ and $R^b$ are directly bound to a common atom, they may be joined to form an oxo group (=O) or form a substituted or unsubstituted saturated or unsaturated 3-10 member ring, which may optionally include heteroatoms which may be the same or different and are selected from O, $NR^a$ or S;

each occurrence of Y is independently selected from O, S and NR$^a$;

each occurrence of n independently represents an integer 0, 1, 2, 3, or 4; and each occurrence of q independently represents an integer 0, 1 or 2.

Some of the compounds of the present invention appear in different tautomeric forms. For example, Ring A can include a —C(OH)=N— group which interconverts to —C(O)—NH— and back to —C(OH)=N— again.

Yet another embodiment is a compound having the formula (I) wherein ring A is selected from

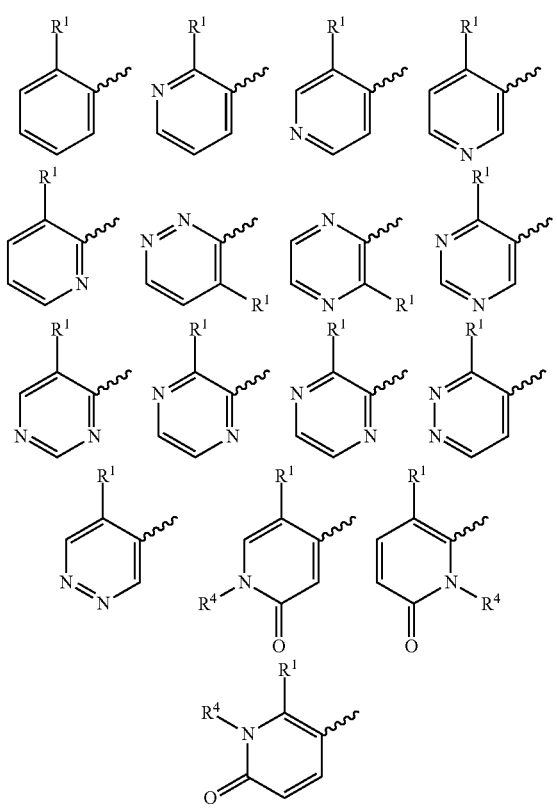

optionally substituted with one or more R$^4$.

Yet another embodiment is a compound having the formula (I) wherein R$^1$ is —COOH, Yet another embodiment is a compound having the formula (I) wherein each occurrence of Y is O.

Yet another embodiment is a compound having the formula (I) wherein the variable Y between ring A and the group —N(R)— is O.

Yet another embodiment is a compound having the formula (I) wherein R is H.

Yet another embodiment is a compound having the formula (I) wherein each occurrence of X is CH, C—Cl, or C—F.

Yet another embodiment, is a compound having the formula (I) wherein each occurrence of X$^1$ is CH, N or CF.

Yet another embodiment, is a compound having the formula (I) wherein X$^2$ is CH, N, CCl or CF.

Yet another embodiment, is a compound having the formula (I) wherein X$^3$ is CH, N, CCl or CF.

Yet another embodiment is a compound having the formula (I) wherein ring B is selected from

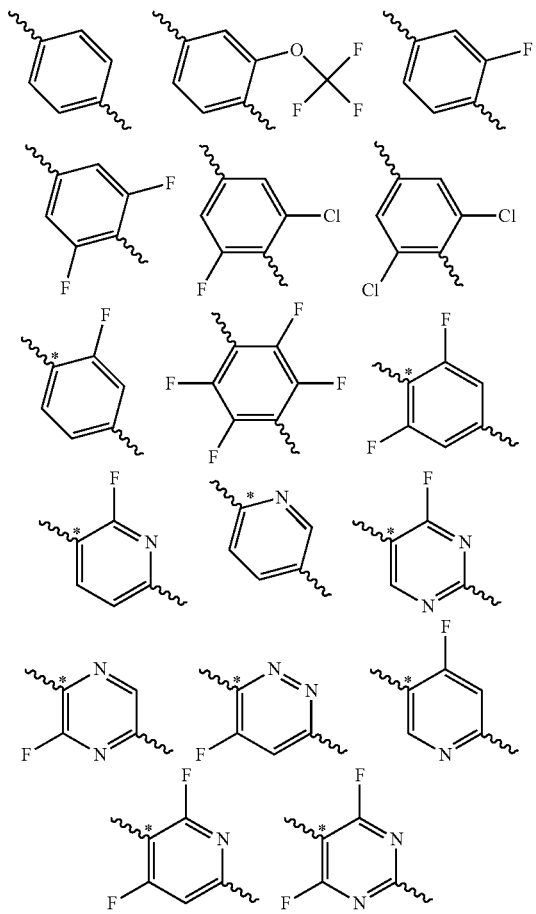

optionally substituted with one or more R$^4$.

Yet another embodiment is a compound having the formula (I), wherein L$_1$ and L$_2$ are absent.

Yet another embodiment is a compound having the formula (I), wherein L$_1$ is absent and L$_2$ is —O—CR$^a$R$^b$.

Yet another embodiment, is a compound having the formula (I), wherein Cy is selected from

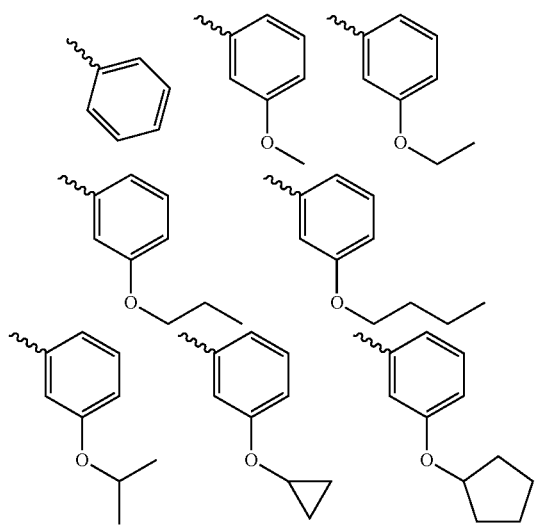

-continued

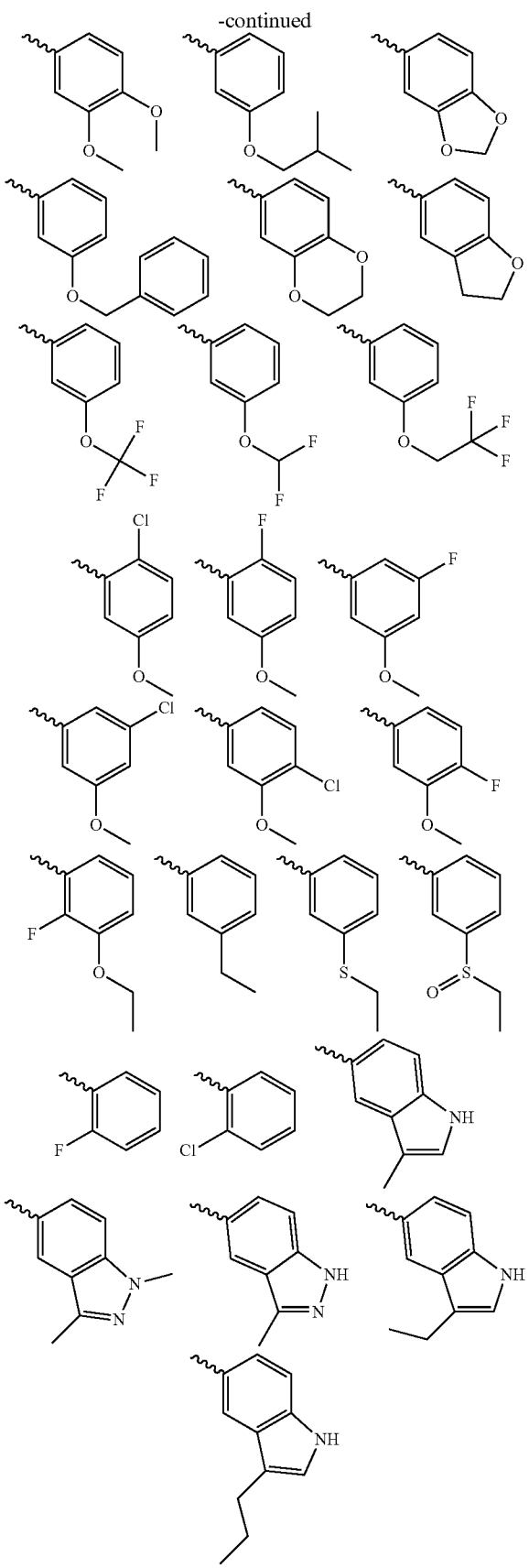

each optionally substituted with one or more R⁴.

In one preferred embodiment, Ring A is phenyl, Ring B is phenyl, Cy is phenyl or 3-ethyl-1H-indol-5-yl, $R^1$ is —COOH, Y is O, $L^1$ is absent, and $L^2$ is absent. In a more preferred embodiment, Cy is phenyl substituted with one or more $C_1$-$C_4$ alkoxy, —S—($C_1$-$C_4$ alkyl), and/or halogen. In a more preferred embodiment, Ring B is phenyl substituted with one or more fluoro groups.

Yet another embodiment is a compound of formula (IA)

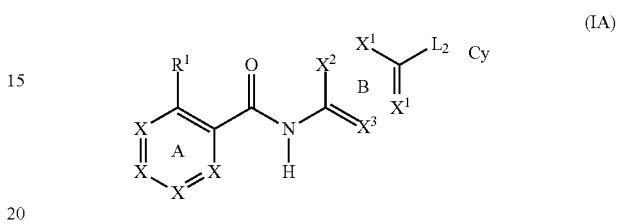

(IA)

or a tautomer, stereoisomer (such as an enantiomer or diastereomer), pharmaceutically acceptable salt, pharmaceutically acceptable ester, prodrug or N-oxide thereof, wherein Ring A is selected from

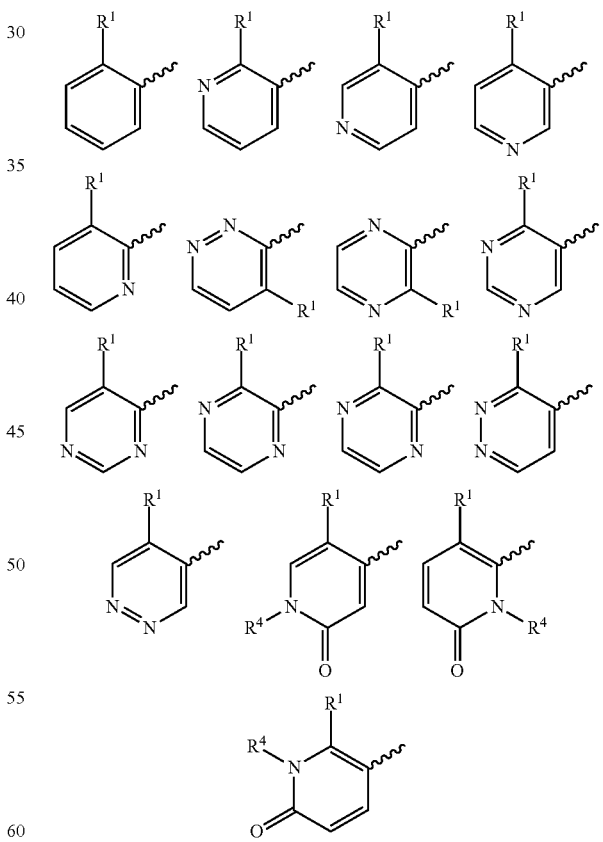

optionally substituted with one or more $R^4$, and $R^1$ is independently selected from —OH, —NR$^a$OH, —COOH, —COOR$^a$, or an isostere of —COOH group, such as SO₃H, CONHOH, B(OH)₂, PO₃R$^a$R$^b$, SO₂NHR$^a$, a tetrazole, an amide, an ester or an acid anhydride.

Ring B is selected from

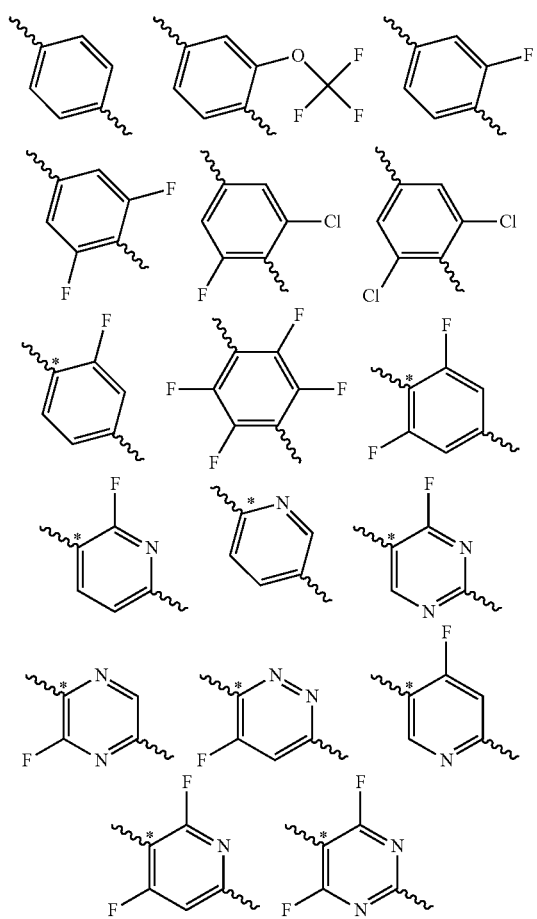

optionally substituted with one or more $R^4$.
and all other variables are the same as described above in relation to formula (I).

Yet another embodiment is a compound of formula (IA)

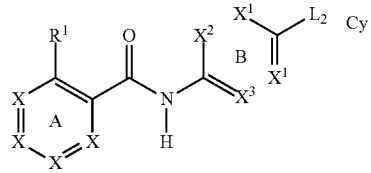

(IA)

or a tautomer, stereoisomer (such as an enantiomer or diastereomer), pharmaceutically acceptable salt, pharmaceutically acceptable ester, prodrug or N-oxide thereof, wherein Ring A is selected from

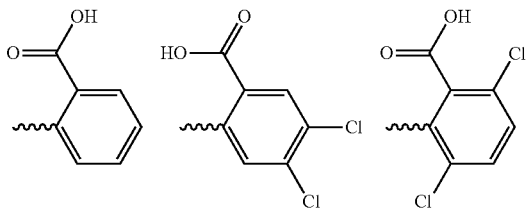

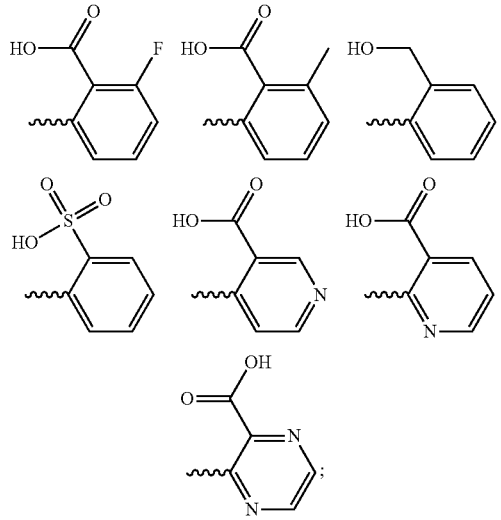

Ring B is selected from

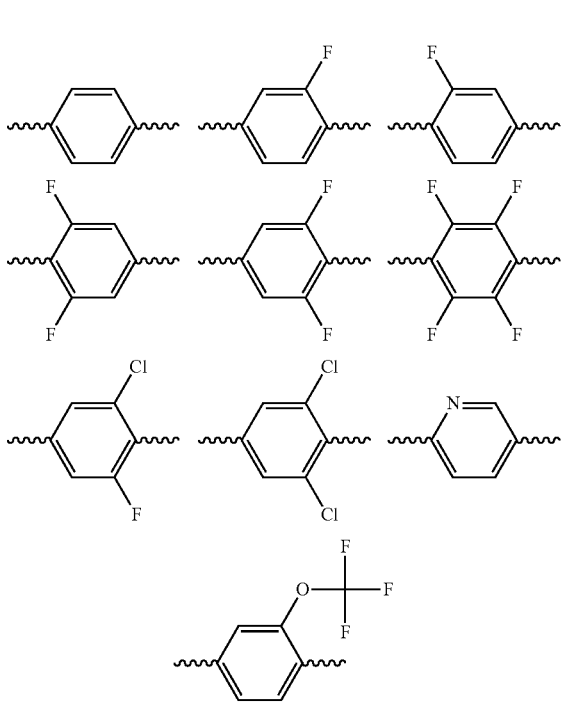

optionally substituted with one or more $R^4$;

$L_2$ is absent or is O—$CR^aR^b$—;

Cy is substituted phenyl, substituted indole or substituted indazole, such as

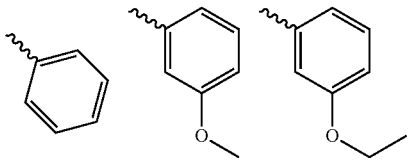

-continued

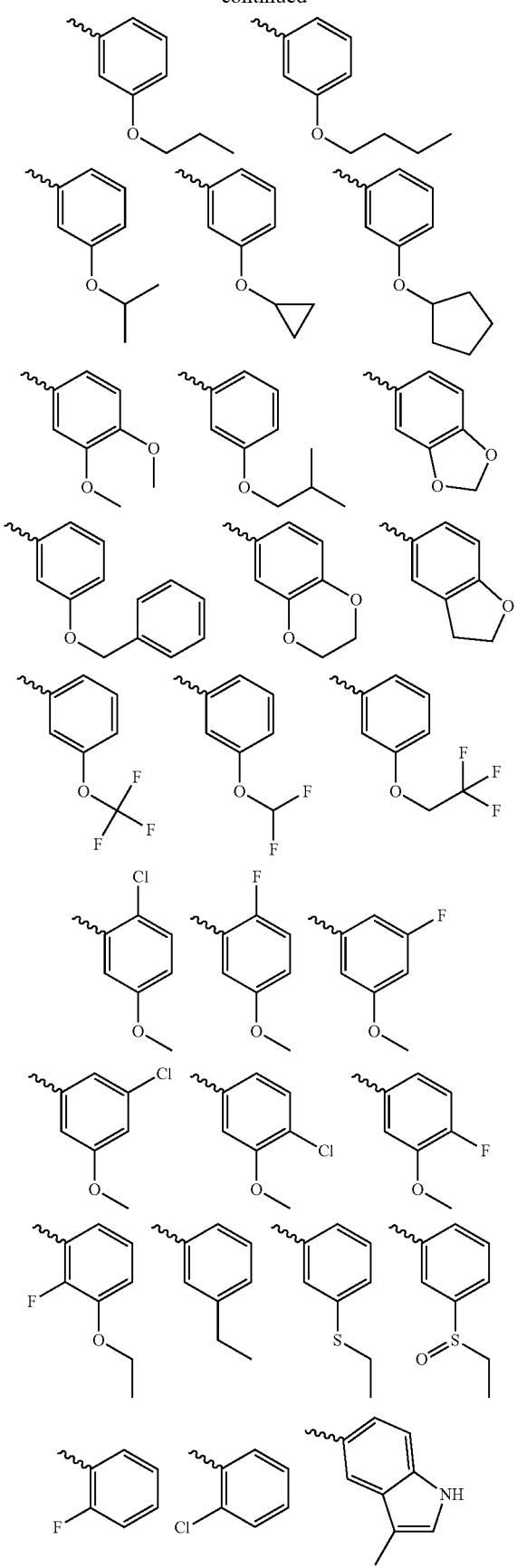

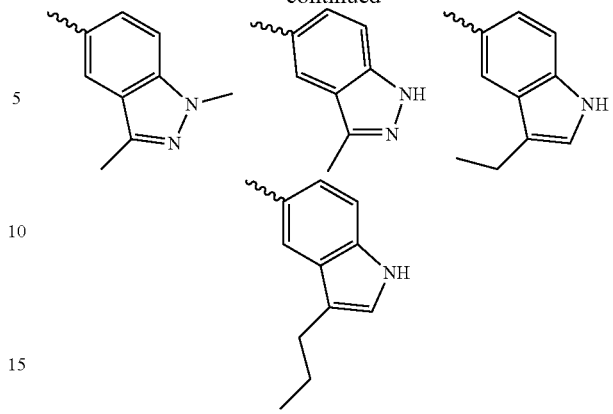

and all other variables are the same as described above in relation to formula (I).

Representative compounds of the present invention include those specified below and pharmaceutically acceptable salts thereof (Table 1). The present invention should not be construed to be limited to them.

1. 2-(3,5-Difluoro-3'-methoxybiphenyl-4-ylcarbamoyl)benzoic acid
2. 2-(3,5-Difluoro-3'-methoxybiphenyl-4-ylcarbamoyl)benzenesulfonic acid
3. 2-(6-(3-Methoxyphenyl)pyridin-3-ylcarbamoyl)benzoic acid
4. 2-(3'-Ethoxy-3-fluorobiphenyl-4-ylcarbamoyl)benzoic acid
5. 2-(3'-Ethoxy-3,5-difluorobiphenyl-4-ylcarbamoyl)benzoic acid
6. 3-(3,5-Difluoro-3'-methoxybiphenyl-4-ylcarbamoyl)pyrazine-2-carboxylic acid
7. 3-(3,5-Difluoro-3'-ethoxybiphenyl-4-ylcarbamoyl)pyrazine-2-carboxylic acid
8. 2-(2'-Chloro-3,5-difluorobiphenyl-4-ylcarbamoyl)benzoic acid
9. 3-[3'-(Benzyloxy)-3,5-difluorobiphenyl-4-ylcarbamoyl]pyrazine-2-carboxylic acid
10. 2-(3,5-Difluorobiphenyl-4-ylcarbamoyl)benzoic acid
11. 3-(3-Chloro-3'-ethoxy-5-fluorobiphenyl-4-ylcarbamoyl)pyrazine-2-carboxylic acid
12. 2-[3,5-Difluoro-3'-(trifluoromethoxy)biphenyl-4-ylcarbamoyl]benzoic acid
13. 2-[3'-(Benzyloxy)-3,5-difluorobiphenyl-4-ylcarbamoyl]benzoic acid
14. 4,5-Dichloro-2-(3-chloro-3'-ethoxy-5-fluorobiphenyl-4-ylcarbamoyl)benzoic acid
15. 2-(3-Chloro-3'-ethoxy-5-fluorobiphenyl-4-ylcarbamoyl)benzoic acid
16. 4,5-Dichloro-2-(3,5-difluoro-3'-methoxybiphenyl-4-ylcarbamoyl)benzoic acid
17. 4,5-Dichloro-2-(3'-ethoxy-3,5-difluorobiphenyl-4-ylcarbamoyl)benzoic acid
18. 2-(3,5-Dichloro-3'-methoxybiphenyl-4-ylcarbamoyl)benzoic acid
19. 2-(3-Chloro-5-fluoro-3'-propoxybiphenyl-4-ylcarbamoyl)benzoic acid
20. 2-(3-Chloro-2',5-difluorobiphenyl-4-ylcarbamoyl)benzoic acid
21. 2-(3,5-Dichloro-3'-ethoxybiphenyl-4-ylcarbamoyl)benzoic acid
22. 2-[3-Fluoro-3'-(trifluoromethoxy)biphenyl-4-ylcarbamoyl]benzoic acid 23. 2-[2'-Fluoro-3-(trifluoromethoxy)biphenyl-4-ylcarbamoyl]benzoic acid
24. 2-(3,5-Dichloro-2'-fluorobiphenyl-4-ylcarbamoyl)benzoic acid
25. 2-(3,5-Difluoro-3'-isopropoxybiphenyl-4-ylcarbamoyl)benzoic acid
26. 2-(3,5-Difluoro-3'-propoxybiphenyl-4-ylcarbamoyl)benzoic acid
27. 4,5-Dichloro-2-(2',3-dichloro-5-fluorobiphenyl-4-ylcarbamoyl)benzoic acid
28. 3,6-dichloro-2-(3'-ethoxy-3,5-difluorobiphenyl-4-ylcarbamoyl)benzoic acid
29. 2-(3'-butoxy-3-chloro-5-fluorobiphenyl-4-ylcarbamoyl)benzoic acid
30. 4,5-Dichloro-2-(2'-chloro-3,5-difluorobiphenyl-4-ylcarbamoyl)benzoic acid
31. 2-(3-Chloro-5-fluoro-3'-isobutoxybiphenyl-4-ylcarbamoyl)benzoic acid
32. 2-(2',3,5-Trifluorobiphenyl-4-ylcarbamoyl)benzoic acid
33. 2-(2',3,5-Trichlorobiphenyl-4-ylcarbamoyl)benzoic acid
34. 2-(3,5-Difluoro-3'-isobutoxybiphenyl-4-ylcarbamoyl)benzoic acid
35. 2-(3'-Butoxy-3,5-difluorobiphenyl-4-ylcarbamoyl)benzoic acid
36. N-(3-Chloro-3'-ethoxy-5-fluorobiphenyl-4-yl)-2-(hydroxymethyl)benzamide
37. N-(3'-Ethoxy-3,5-difluorobiphenyl-4-yl)-2-(hydroxymethyl)benzamide
38. 2-(3-Chloro-3'-ethoxy-5-fluorobiphenyl-4-ylcarbamoyl)-6-fluorobenzoic acid
39. 2-[3-Chloro-5-fluoro-3'-(trifluoromethoxy)biphenyl-4-ylcarbamoyl]benzoic acid
40. 2-[4-(Benzyloxy)-2,6-difluorophenylcarbamoyl]benzoic acid
41. 2-[3'-(Cyclopentyloxy)-3,5-difluorobiphenyl-4-ylcarbamoyl]benzoic acid
42. 2-(3-Chloro-3'-(cyclopentyloxy)-5-fluorobiphenyl-4-ylcarbamoyl)benzoic acid
43. 2-[3'-(Difluoromethoxy)-3,5-difluorobiphenyl-4-ylcarbamoyl]benzoic acid
44. 2-[3-Chloro-3'-(difluoromethoxy)-5-fluorobiphenyl-4-ylcarbamoyl]benzoic acid
45. 2-(2'-Chloro-3,5-difluoro-5'-methoxybiphenyl-4-ylcarbamoyl)benzoic acid
46. 2-(3,3',5-Trifluoro-5'-methoxybiphenyl-4-ylcarbamoyl)benzoic acid
47. 2-[4-(Benzo[d][1,3]dioxol-5-yl)-2,6-difluorophenylcarbamoyl]benzoic acid
48. 2-[4-(Benzo[d][1,3]dioxol-5-yl)-2-chloro-6-fluorophenylcarbamoyl]benzoic acid
49. 2-(3,5-Difluoro-3',4'-dimethoxybiphenyl-4-ylcarbamoyl)benzoic acid
50. 2-(3,3',5-Trifluoro-5'-methoxybiphenyl-4-ylcarbamoyl)benzoic acid
51. 2-(3,3'-Dichloro-5-fluoro-5'-methoxybiphenyl-4-ylcarbamoyl)benzoic acid
52. 2-[4-(2,3-Dihydrobenzofuran-5-yl)-2,6-difluorophenylcarbamoyl]benzoic acid
53. 2-[2-Chloro-4-(2,3-dihydrobenzofuran-5-yl)-6-fluorophenylcarbamoyl]benzoic acid
54. 2-[4-(1,3-Dimethyl-1H-indazol-5-yl)-2,6-difluorophenylcarbamoyl]benzoic acid
55. 2-(3'-Chloro-3,5-difluoro-5'-methoxybiphenyl-4-ylcarbamoyl)benzoic acid
56. 2-(3-Chloro-5-fluoro-3',4'-dimethoxybiphenyl-4-ylcarbamoyl)benzoic acid
57. 2-(2',3-Dichloro-5-fluoro-5'-methoxybiphenyl-4-ylcarbamoyl)benzoic acid
58. 2-(2',3,5-Trifluoro-5'-methoxybiphenyl-4-ylcarbamoyl)benzoic acid
59. 2-(4'-Chloro-3,5-difluoro-3'-methoxybiphenyl-4-ylcarbamoyl)benzoic acid
60. 2-(3,4'-Dichloro-5-fluoro-3'-methoxybiphenyl-4-ylcarbamoyl)benzoic acid
61. 2-(3-chloro-2',5-difluoro-5'-methoxybiphenyl-4-ylcarbamoyl)benzoic acid
62. 2-(3,4',5-trifluoro-3'-methoxybiphenyl-4-ylcarbamoyl)benzoic acid
63. 2-[2,6-difluoro-4-(3-methyl-1H-indol-5-yl)phenylcarbamoyl]benzoic acid
64. 2-[2,6-difluoro-4-(3-methyl-1H-indazol-5-yl)phenylcarbamoyl]benzoic acid
65. 2-(3-chloro-3'-ethyl-5-fluorobiphenyl-4-ylcarbamoyl)benzoic acid
66. 2-(3-chloro-3'-ethoxy-2',5-difluorobiphenyl-4-ylcarbamoyl)benzoic acid
67. 2-[2-chloro-4-(2,3-dihydrobenzo[b][1,4]dioxin-6-yl)-6-fluorophenylcarbamoyl]benzoic acid
68. 2-[3-chloro-5-fluoro-3'-(2,2,2-trifluoroethoxy)biphenyl-4-ylcarbamoyl]benzoic acid
69. 2-(3-fluoro-3'-methoxybiphenyl-4-ylcarbamoyl)benzoic acid
70. 2-(3'-ethoxybiphenyl-4-ylcarbamoyl)benzoic acid
71. 2-[3'-(ethylthio)-3,5-difluorobiphenyl-4-ylcarbamoyl]benzoic acid
72. 2-[3'-(ethylsulfinyl)-3,5-difluorobiphenyl-4-ylcarbamoyl]benzoic acid
73. 2-(3'-cyclopropoxy-3,5-difluorobiphenyl-4-ylcarbamoyl)benzoic acid
74. 2-(3'-ethoxy-3,5-difluorobiphenyl-4-ylcarbamoyl)-6(5)-methylbenzoic acid
75. 2-[4-(3-ethyl-1H-indol-5-yl)-2,6-difluorophenylcarbamoyl]benzoic acid
76. 2-(3'-ethoxy-3,5-difluorobiphenyl-4-ylcarbamoyl)nicotinic acid
77. 4-(3'-ethoxy-3,5-difluorobiphenyl-4-ylcarbamoyl)nicotinic acid
78. 2-[3'-(ethylthio)-2,3,5,6-tetrafluorobiphenyl-4-ylcarbamoyl]benzoic acid
79. 2-(2'-chloro-2-fluoro-5'-methoxybiphenyl-4-ylcarbamoyl)benzoic acid
80. 2-(3-fluoro-3'-propoxybiphenyl-4-ylcarbamoyl)benzoic acid
81. 2-(3'-propoxybiphenyl-4-ylcarbamoyl)benzoic acid
82. 2-[3'-(ethylthio)-2-fluorobiphenyl-4-ylcarbamoyl]benzoic acid
83. 2-[3,5-difluoro-3'-(2,2,2-trifluoroethoxy)biphenyl-4-ylcarbamoyl]benzoic acid
84. 2-(3'-ethyl-3,5-difluorobiphenyl-4-ylcarbamoyl)benzoic acid
85. 2-(biphenyl-4-ylcarbamoyl)benzoic acid
86. 2-(2'-chlorobiphenyl-4-ylcarbamoyl)benzoic acid
87. 2-(3'-methoxybiphenyl-4-ylcarbamoyl)benzoic acid
88. 2-[3'-(trifluoromethoxy)biphenyl-4-ylcarbamoyl]benzoic acid
89. 2-[3'-(ethylthio)-2,6-difluorobiphenyl-4-ylcarbamoyl]benzoic acid
90. 2-(3'-ethylbiphenyl-4-ylcarbamoyl)benzoic acid
91. 2-(3'-butoxy-2,3,5,6-tetrafluorobiphenyl-4-ylcarbamoyl)benzoic acid
92. 2-(3'-butoxy-3-fluorobiphenyl-4-ylcarbamoyl)benzoic acid 93. 2-[3,5-difluoro-3'-(trifluoromethoxy)biphenyl-4-ylcarbamoyl]benzoic acid
94. 2-(3'-cyclopropoxy-3-fluorobiphenyl-4-ylcarbamoyl)benzoic acid
95. 2-(3'-cyclopropoxybiphenyl-4-ylcarbamoyl)benzoic acid
96. 2-(3'-butoxybiphenyl-4-ylcarbamoyl)benzoic acid
97. 2-(3'-butoxy-2-fluorobiphenyl-4-ylcarbamoyl)benzoic acid
98. 2-(3'-Butoxy-2,6-difluorobiphenyl-4-ylcarbamoyl)benzoic acid
99. 2-[2,6-Difluoro-4-(3-propyl-1H-indol-5-yl)phenylcarbamoyl]benzoic acid
100. 2-[2-Chloro-4-(3-ethyl-1H-indol-5-yl)-6-fluorophenylcarbamoyl]benzoic acid TABLE 1-continued

| Ex. | Structure |
|---|---|
| 15. | (structure: 3-EtO-phenyl-biphenyl with F, Cl substituents, NH-C(O)-benzoic acid) |
| 16. | (structure: 3-MeO-phenyl-biphenyl with 2 F substituents, NH-C(O)-4,5-dichlorobenzoic acid) |
| 17. | (structure: 3-EtO-phenyl-biphenyl with 2 F substituents, NH-C(O)-4,5-dichlorobenzoic acid) |
| 18. | (structure: 3-MeO-phenyl-biphenyl with 2 Cl substituents, NH-C(O)-benzoic acid) |
| 19. | (structure: 3-n-PrO-phenyl-biphenyl with F, Cl substituents, NH-C(O)-benzoic acid) |
| 20. | (structure: 2'-F-biphenyl with F, Cl substituents, NH-C(O)-benzoic acid) |
| 21. | (structure: 3-EtO-phenyl-biphenyl with 2 Cl substituents, NH-C(O)-benzoic acid) |
| 22. | (structure: 3-F₃CO-phenyl-biphenyl with F substituent, NH-C(O)-benzoic acid) |
| 23. | (structure: 2'-F-biphenyl with OCF₃ substituent, NH-C(O)-benzoic acid) |
| 24. | (structure: 2'-F-biphenyl with 2 Cl substituents, NH-C(O)-benzoic acid) |
| 25. | (structure: 3-iPrO-phenyl-biphenyl with 2 F substituents, NH-C(O)-benzoic acid) |
| 26. | (structure: 3-n-PrO-phenyl-biphenyl with 2 F substituents, NH-C(O)-benzoic acid) |
| 27. | (structure: 2'-Cl-biphenyl with Cl, F substituents, NH-C(O)-4,5-dichlorobenzoic acid) |
| 28. | (structure: 3-EtO-phenyl-biphenyl with 2 F substituents, NH-C(O)-3,6-dichlorobenzoic acid) |
| 29. | (structure: 3-n-BuO-phenyl-biphenyl with F, Cl substituents, NH-C(O)-benzoic acid) |
| 30. | (structure: 2'-Cl-biphenyl with 2 F substituents, NH-C(O)-4,5-dichlorobenzoic acid) |

TABLE 1-continued

| Ex. | Structure |
|---|---|
| 31. | (i-BuO, F, Cl substituted biphenyl)-NH-C(O)-(2-HOOC-phenyl) |
| 32. | (2'-F, 3,5-diF biphenyl)-NH-C(O)-(2-HOOC-phenyl) |
| 33. | (2'-Cl, 3,5-diCl biphenyl)-NH-C(O)-(2-HOOC-phenyl) |
| 34. | (i-BuO, 3,5-diF biphenyl)-NH-C(O)-(2-HOOC-phenyl) |
| 35. | (n-BuO, 3,5-diF biphenyl)-NH-C(O)-(2-HOOC-phenyl) |
| 36. | (EtO, F, Cl biphenyl)-NH-C(O)-(2-HOCH$_2$-phenyl) |
| 37. | (EtO, 3,5-diF biphenyl)-NH-C(O)-(2-HOCH$_2$-phenyl) |
| 38. | (EtO, F, Cl biphenyl)-NH-C(O)-(2-HOOC-3-F-phenyl) |
| 39. | (F$_3$CO, F, Cl biphenyl)-NH-C(O)-(2-HOOC-phenyl) |
| 40. | (benzyloxy, 3,5-diF phenyl)-NH-C(O)-(2-HOOC-phenyl) |
| 41. | (cyclopentyloxy, 3,5-diF biphenyl)-NH-C(O)-(2-HOOC-phenyl) |
| 42. | (cyclopentyloxy, F, Cl biphenyl)-NH-C(O)-(2-HOOC-phenyl) |
| 43. | (F$_2$HCO, 3,5-diF biphenyl)-NH-C(O)-(2-HOOC-phenyl) |
| 44. | (F$_2$HCO, F, Cl biphenyl)-NH-C(O)-(2-HOOC-phenyl) |
| 45. | (MeO, 2'-Cl, 3,5-diF biphenyl)-NH-C(O)-(2-HOOC-phenyl) |

TABLE 1-continued

| Ex. | Structure |
|---|---|
| 46. | (chemical structure) |
| 47. | (chemical structure) |
| 48. | (chemical structure) |
| 49. | (chemical structure) |
| 50. | (chemical structure) |
| 51. | (chemical structure) |
| 52. | (chemical structure) |
| 53. | (chemical structure) |
| 54. | (chemical structure) |
| 55. | (chemical structure) |
| 56. | (chemical structure) |
| 57. | (chemical structure) |
| 58. | (chemical structure) |
| 59. | (chemical structure) |
| 60. | (chemical structure) |
| 61. | (chemical structure) |

TABLE 1-continued

| Ex. | Structure |
|---|---|
| 62. | (structure) |
| 63. | (structure) |
| 64. | (structure) |
| 65. | (structure) |
| 66. | (structure) |
| 67. | (structure) |
| 68. | (structure) |
| 69. | (structure) |
| 70. | (structure) |
| 71. | (structure) |
| 72. | (structure) |
| 73. | (structure) |
| 74. | (structure) |
| 75. | (structure) |
| 76. | (structure) |
| 77. | (structure) |

TABLE 1-continued
| Ex. | Structure |
|---|---|
| 78. | 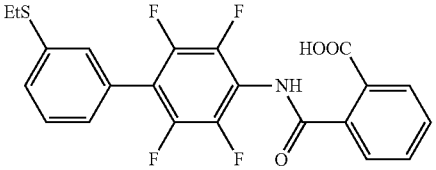 |
| 79. | 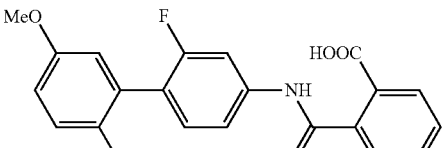 |
| 80. | 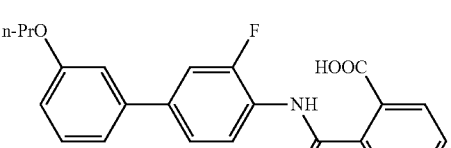 |
| 81. | 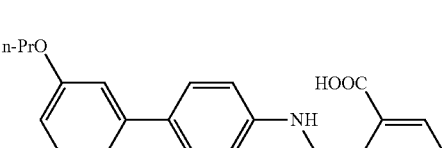 |
| 82. | 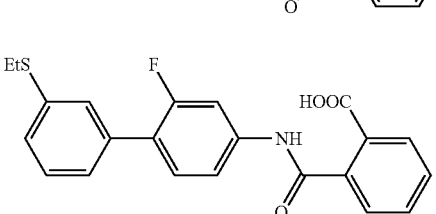 |
| 83. | 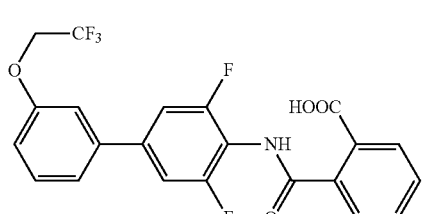 |
| 84. | 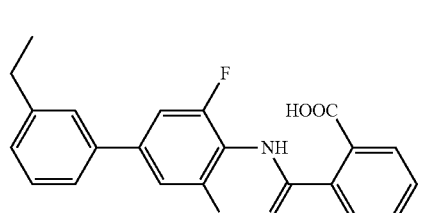 |
| 85. | 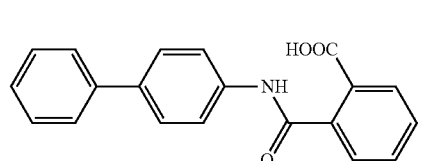 |
TABLE 1-continued
| Ex. | Structure |
|---|---|
| 86. | 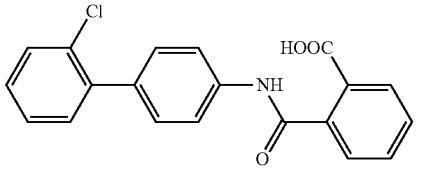 [SMILES: O=C(O)c1ccccc1C(=O)Nc1ccc(-c2ccccc2Cl)cc1] |
| 87. | 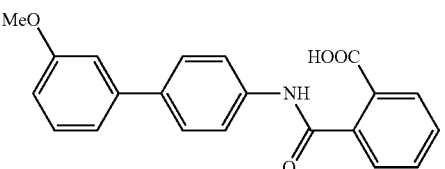 |
| 88. | 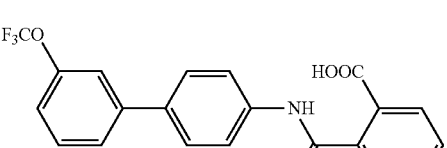 |
| 89. | 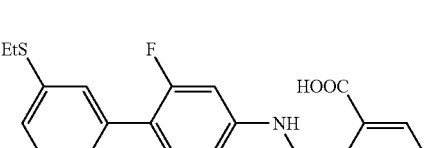 |
| 90. | 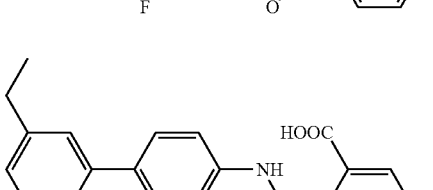 |
| 91. | 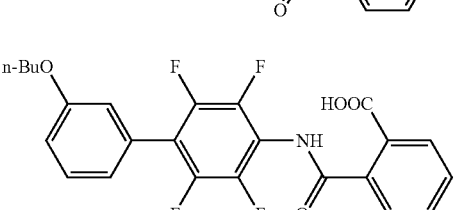 |
| 92. | 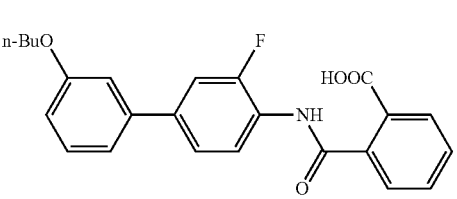 |
| 93. | 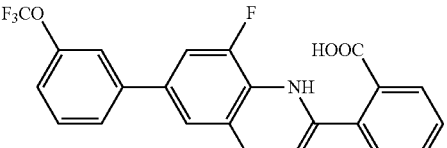 |

TABLE 1-continued

| Ex. | Structure |
|---|---|
| 94. | (cyclopropylmethoxy)-substituted biphenyl with F, linked via NH-C(O) to benzoic acid (HOOC) |
| 95. | (cyclopropylmethoxy)-substituted biphenyl linked via NH-C(O) to benzoic acid (HOOC) |
| 96. | n-BuO-substituted biphenyl linked via NH-C(O) to benzoic acid (HOOC) |
| 97. | n-BuO-substituted biphenyl with F, linked via NH-C(O) to benzoic acid (HOOC) |
| 98. | n-BuO-substituted biphenyl with two F, linked via NH-C(O) to benzoic acid (HOOC) |
| 99. | n-Pr-substituted indole-phenyl with two F, linked via NH-C(O) to benzoic acid (HOOC) |
| 100 | ethyl-substituted indole-phenyl with F and Cl, linked via NH-C(O) to benzoic acid (HOOC) |

Yet another embodiment is a method of inhibiting DHODH in a patient in need thereof by administering to the patient an effective amount of a compound of formula (I) or/and (IA).

Yet another embodiment is a method of inhibiting IL-17 in a patient in need thereof by administering to the patient an effective amount of a compound of formula (I) or/and (IA).

In particular compounds of formula (I) and (IA), or their pharmaceutically acceptable salts thereof are DHODH inhibitors useful in the treatment, prevention and/or amelioration of diseases or disorders wherein the inhibition of DHODH is known to show beneficial effect.

Another embodiment of the present invention is a method for treating an immunological disorder, inflammatory disorder, cancer or other proliferative disease via inhibition of DHODH by administering to a patient in need of such treatment an effective amount of at least one compound of formula (I) or/and (IA), as defined above.

Another embodiment of the present invention is a method for treating an immunological disorder, inflammatory disorder, cancer or other proliferative disease via inhibition of IL-17 either directly or by inhibition of DHODH by administering to a patient in need of such treatment an effective amount of at least one compound of formula (I) or/and (IA), as defined above.

Another embodiment of the present invention is a method for treating an immunological disorder, inflammatory disorder, cancer or other proliferative disease via inhibition of IL-17 as well DHODH by administering to a patient in need of such treatment an effective amount of at least one compound of formula (I) or/and (IA), as defined above.

Yet another embodiment of the present invention is a method for treating an immunological disorder, inflammatory disorder, cancer or other proliferative disease via inhibition of DHODH by administering to a patient in need of such treatment an effective amount of at least one compound of formula (I) or/and (IA), as defined above, in combination (simultaneously or sequentially) with at least one other anti-inflammatory, immunomodulator or anti-cancer agent.

The compounds of formula (I) or/and (IA), are useful in the treatment of a variety of disorders, including, but not limited to, autoimmune diseases, immune and inflammatory diseases, destructive bone disorders, cancers and malignant neoplastic diseases, angiogenic-related disorders, viral diseases, and infectious diseases. Such disorders include, but are not limited to:

Autoimmune diseases which may be prevented (prophylactically) or treated include but are not limited to rheumatoid arthritis, psoriatic arthritis, systemic lupus erythematosus, multiple sclerosis, psoriasis, ankylosing spondilytis, Wegener's granulomatosis, polyarticular juvenile idiopathic arthritis, inflammatory bowel disease such as ulcerative colitis and Crohn's disease, Reiter's syndrome, fibromyalgia and type-1 diabetes.

Immune and inflammatory diseases which may be prevented (prophylactically) or treated include but are not limited to asthma, COPD, respiratory distress syndrome, acute or chronic pancreatitis, graft versus-host disease, chronic sarcoidosis, transplant rejection, contact dermatitis, atopic dermatitis allergic rhinitis, allergic conjunctivitis, Behçet's syndrome, inflammatory eye conditions such as conjunctivitis and uveitis.

Destructive bone disorders which may be prevented or treated include but are not limited to osteoporosis, osteoarthritis and multiple myeloma-related bone disorder.

Cancers and malignant neoplastic diseases that may be prevented (prophylactically) or treated include but are not limited to prostate, ovarian and brain cancer. Carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Agiogenesis-related disorders that may be prevented or treated include but are not limited to hemangiomas, ocular neovascularization, macular degeneration or diabetic retinopathy.

Viral diseases which may be prevented or treated include but are not limited to HIV infection, hepatitis and cytomegalovirus infection.

Infectious diseases which may be prevented or treated include but are not limited to sepsis, septic shock, endotoxic shock, Gram negative sepsis, toxic shock syndrome, Shigellosis and other protozoal infestations such as malaria.

The compounds of the present invention as modulators of apoptosis, are useful in the treatment of cancer (including but not limited to those types mentioned herein above), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The compounds of present invention can modulate the level of cellular RNA and DNA synthesis. These agents are therefore useful in the treatment of viral infections (including but not limited to HIV, human papilloma virus, herpesvirus, poxvirus, Epstein-Barr virus, Sindbis virus and adenovirus).

The compounds of the present invention are useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse. The compounds are also useful in inhibiting tumor angiogenesis and metastasis.

The compounds of the present invention may also be combined with other active compounds in the treatment of diseases wherein the inhibition of DHODH is known to show beneficial effect.

In other embodiments, the diseases, conditions or disorders that benefit from inhibition of DHODH include, but are not limited to, an immune system-related disease (e.g., an autoimmune disease), a disease or disorder involving inflammation (e.g., asthma, chronic obstructive pulmonary disease, rheumatoid arthritis, inflammatory bowel disease, glomerulonephritis, neuroinflammatory diseases, multiple sclerosis, uveitis and disorders of the immune system), cancer or other proliferative disease, hepatic diseases or disorders, renal diseases or disorders.

In one embodiment, compounds described herein are used as immunosuppresants to prevent transplant graft rejections, allogeneic or xenogeneic transplantation rejection (organ, bone marrow, stem cells, other cells and tissues), and graft-versus-host disease. In other embodiments, transplant graft rejections result from tissue or organ transplants. In further embodiments, graft-versus-host disease results from bone marrow or stem cell transplantation.

More particularly, the compounds of formula (I) or/and (IA) are useful in the treatment of a variety of inflammatory diseases including, but not limited to, inflammation, glomerulonephritis, uveitis, hepatic diseases or disorders, renal diseases or disorders, chronic obstructive pulmonary disease, rheumatoid arthritis, inflammatory bowel disease, vasculitis, dermatitis, osteoarthritis, inflammatory muscle disease, allergic rhinitis, vaginitis, interstitial cystitis, scleroderma, osteoporosis, eczema, allogeneic or xenogeneic transplantation, graft rejection, graft-versus-host disease, corneal transplant rejection, lupus erythematosus, systemic lupus erythematosus, prolipherative lupus nephritis, type I diabetes, pulmonary fibrosis, dermatomyositis, thyroiditis, myasthenia gravis, autoimmune hemolytic anemia, cystic fibrosis, chronic relapsing hepatitis, primary biliary cirrhosis, allergic conjunctivitis, hepatitis and atopic dermatitis, asthma and Sjogren's syndrome.

In one embodiment, the compounds described herein are useful in the treatment of a variety of diseases including Felty's syndrome, Wegener's granulomatosis, Crohn's disease, sarcoidosis, Still's disease, pemphigoid, Takayasu arteritis, systemic slerosis, relapsing polychondritis, refractory IgA nephropathy, SAPHO[2] syndrome (SAS), cytomegalovirus infection including rhinitis or cyst, psoriasis and multiple myeloma.

The invention further provides pharmaceutical compositions comprising compounds having formula (I) or/and (IA), together with a pharmaceutically acceptable carrier.

DETAIL DESCRIPTION

Unless defined otherwise, all technical and scientific terms used herein have the same meaning as is commonly understood in the field to which the claimed subject matter belongs. In the event that there is a plurality of definitions for terms herein, those in this section prevail. Where reference is made to a URL or other such identifier or address, it is understood that such identifiers generally change and particular information on the internet comes and goes, but equivalent information is found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Definition of standard chemistry and molecular biology terms are found in reference works, including but not limited to, Carey and Sundberg "ADVANCED ORGANIC CHEMISTRY 4$^{th}$ edition" Vols. A (2000) and B (2001), Plenum Press, New York and "MOLECULAR BIOLOGY OF THE CELL 5$^{th}$ edition" (2007), Garland Science, New York. Unless otherwise indicated, conventional methods of mass spectroscopy, NMR, HPLC, protein chemistry, biochemistry, recombinant DNA techniques and pharmacology are contemplated within the scope of the embodiments disclosed herein.

Unless specific definitions are provided, the nomenclature employed in connection with, and the laboratory procedures and techniques of, analytical chemistry, and medicinal and pharmaceutical chemistry described herein are those generally used. In some embodiments, standard techniques are used for chemical analyses, pharmaceutical preparation, formulation, and delivery, and treatment of patients. In other embodiments, standard techniques are used for recombinant DNA, oligonucleotide synthesis, and tissue culture and transformation (e.g., electroporation, lipofection). In certain embodiments, reactions and purification techniques are performed e.g., using kits of manufacturer's specifications or as described herein. The foregoing techniques and procedures are generally performed of conventional methods and as described in various general and more specific references that are cited and discussed throughout the present specification.

As used herein the following definitions shall apply unless otherwise indicated. Further many of the groups defined herein can be optionally substituted. The listing of substituents in the definition is exemplary and is not to be construed to limit the substituents defined elsewhere in the specification.

The term 'alkyl' refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl).

The term substituted or unsubstituted ($C_{1-2}$)alkyl refers to an alkyl group as defined above having up to 2 carbon atoms, and the term substituted or unsubstituted ($C_{1-6}$)alkyl refers to an alkyl group as defined above having up to 6 carbon atoms.

The term "alkenyl" refers to an aliphatic hydrocarbon group containing a carbon-carbon double bond which may be a straight or branched or branched chain having about 2 to about 10 carbon atoms, e.g., ethenyl, 1-propenyl, 2-propenyl (allyl), iso-propenyl, 2-methyl-1-propenyl, 1-butenyl, and 2-butenyl.

The term substituted or unsubstituted ($C_2$)alkenyl refers to an alkenyl group as defined above having 2 carbon atoms.

The term "alkynyl" refers to a straight or branched chain hydrocarbyl radicals having at least carbon-carbon triple bond, and having in the range of 2 up to 12 carbon atoms (with radicals having in the range of about 2 up to 10 carbon atoms presently being preferred), e.g., ethynyl, propynyl, and butynyl.

The term substituted or unsubstituted ($C_2$) alkynyl refers to an alkynyl group as defined above having 2 carbon atoms.

The term "alkoxy" denotes an alkyl group as defined above attached via an oxygen linkage to the rest of the molecule. Representative examples of these groups are —$OCH_3$ and —$OC_2H_5$.

The term "cycloalkyl" denotes a non-aromatic mono or multicyclic ring system of about 3 to 12 carbon atoms such as cyclopropyl, cyclobutyl, cyclopentyl, and cyclohexyl. Examples of multicyclic cycloalkyl groups include perhydronaphthyl, adamantyl and norbornyl groups, bridged cyclic groups, and sprirobicyclic groups, e.g., sprio (4,4) non-2-yl.

The term "cycloalkylalkyl" refers to a cyclic ring-containing radical containing in the range of 3 up to 8 carbon atoms directly attached to an alkyl group which are then attached to the main structure at any carbon from the alkyl group that results in the creation of a stable structure such as cyclopropylmethyl, cyclobuyylethyl, and cyclopentylethyl.

The term "cycloalkenyl" refers to cyclic ring-containing radicals containing in the range of 3 up to 8 carbon atoms with at least one carbon-carbon double bond such as cyclopropenyl, cyclobutenyl, and cyclopentenyl. The term "cycloalkenylalkyl" refers to a cycloalkenyl group directly attached to an alkyl group which are then attached to the main structure at any carbon from the alkyl group that results in the creation of a stable structure The term "aryl" refers to an aromatic radical having in the range of 6 up to 20 carbon atoms such as phenyl, naphthyl, tetrahydronapthyl, indanyl, and biphenyl.

The term "arylalkyl" refers to an aryl group as defined above directly bonded to an alkyl group as defined above. e.g., —$CH_2C_6H_5$ and —$C_2H_5C_6H_5$.

The term "heterocyclic ring" refers to a non-aromatic 3 to 15 member ring radical which, consists of carbon atoms and at least one heteroatom selected from the group consisting of nitrogen, phosphorus, oxygen and sulfur. For purposes of this invention, the heterocyclic ring radical may be a mono-, bi-, tri- or tetracyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized. The heterocyclic ring radical may be attached to the main structure at any heteroatom or carbon atom that results in the creation of a stable structure.

The term "heteroaryl" refers to an optionally substituted 5-14 member aromatic ring having one or more heteroatoms selected from N, O, and S as ring atoms. The heteroaryl may be a mono-, bi- or tricyclic ring system. Examples of such heteroaryl ring radicals include, but are not limited to, oxazolyl, thiazolyl imidazolyl, pyrrolyl, furanyl, pyridinyl, pyrimidinyl, pyrazinyl, benzofuranyl, indolyl, benzothiazolyl, benzoxazolyl, carbazolyl, quinolyl and isoquinolyl. The heteroaryl ring radical may be attached to the main structure at any heteroatom or carbon atom that results in the creation of a stable structure.

Examples of such "heterocyclic ring" or "heteroaryl" radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide thiamorpholinyl sulfone, dioxaphospholanyl oxadiazolyl, chromanyl, and isochromanyl.

The term "heteroarylalkyl" refers to a heteroaryl ring radical as defined above directly bonded to an alkyl group. The heteroarylalkyl radical may be attached to the main structure at any carbon atom from the alkyl group that results in the creation of a stable structure.

The term "heterocyclyl" refers to a heterocylic ring radical as defined above. The heterocylcyl ring radical may be attached to the main structure at any heteroatom or carbon atom that results in the creation of a stable structure.

The term "heterocyclylalkyl" refers to a heterocylic ring radical as defined above directly bonded to an alkyl group. The heterocyclylalkyl radical may be attached to the main structure at a carbon atom in the alkyl group that results in the creation of a stable structure.

The term "cyclic ring" refers to a cyclic ring containing 3-10 carbon atoms, optionally one or more of the ring carbon atoms may be replaced with heteroatom such as N, O, or S atom.

The term "monocyclic ring" refers to a single cyclic ring containing 3-10 carbon atoms, optionally one or more of the ring carbon atoms may be replaced with heteroatom such as N, O, or S atom.

The prefix "monocyclic ring" being used such as for example monocyclic aryl, refers to single aryl ring wherein the aryl is as defined herein above. Similarly the term monocyclic heteroaryl refers to a single heteroaryl ring wherein the heteroaryl is as defined herein above. The same is applicable to each of the terms monocyclic cycloalkyl and monocyclic heterocyclic ring as well.

The term "substituted" unless otherwise specified, refers to substitution with any one or any combination of the following substituents and may be the same or different which one or more are selected from hydrogen, hydroxy, halogen, carboxyl, cyano, nitro, oxo (═O), thio (═S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclic ring, substituted or unsubstituted heterocyclcyalkyl, substituted or unsubstituted aryl, substituted or unsubstituted arylalkyl, substituted or unsubstituted heteroaryl, substituted or unsubstituted heteroarylalkyl, substituted or unsubstituted guanidine, —COOR$^x$, —C(O)R$^x$, —C(S)R$^x$, —C(O)NR$^x$R$^y$, —C(O)ONR$^x$R$^y$, —NR$^y$R$^z$, —NR$^x$CONR$^y$R$^z$, —N(R$^x$)SOR$^y$, —N(R$^x$)SO$_2$R$^y$, —(═N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$NR$^x$R$^y$—, —OR$^x$, —OR$^x$C(O)NR$^y$R$^z$, —OR$^x$C(O)OR$^y$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^y$, —R$^x$OC(O)R$^y$, —SR, —SOR$^x$, —SO$_2$R$^x$, —ONO$_2$, wherein R$^x$, R$^y$ and R$^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclic ring, substituted or unsubstituted heterocyclcyalkyl, substituted or unsubstituted aryl, substituted or unsubstituted arylalkyl, substituted or unsubstituted heteroaryl, substituted or unsubstituted heteroarylalkyl, or any two of R$^x$, R$^y$ and R$^z$ may be joined to form a substituted or unsubstituted saturated or unsaturated 3-10 membered ring, which may optionally include heteroatoms which may be the same or different and are selected from O, NR$^X$ or S. Substitution or the combination of substituents envisioned by this invention are preferably those that result in the formation of a stable or chemically feasible compounds. The term stable as used herein refers to the compounds or the structure that are not substantially altered when subjected to conditions to allow for their production, detection and preferably their recovery, purification and incorporation into a pharmaceutical composition.

The term "halogen" or "halo" refers to radicals of fluorine, chlorine, bromine and iodine.

The term "protecting group" or "PG" refers to a substituent that is employed to block or protect a particular functionality. Other functional groups on the compound may remain reactive. For example, an "amino-protecting group" is a substituent attached to an amino group that blocks or protects the amino functionality in the compound. Suitable amino-protecting groups include, but are not limited to, acetyl, trifluoroacetyl, tert-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include, but are not limited to, acetyl and silyl. A "carboxy-protecting group" refers to a substituent of the carboxy group that blocks or protects the carboxy functionality. Suitable carboxy-protecting groups include, but are not limited to, —CH$_2$CH$_2$SO$_2$Ph, cyanoethyl, 2-(trimethylsilyl) ethyl, 2-(trimethylsilyl)ethoxymethyl, -2-(p-toluenesulfonyl)ethyl, 2-(p-nitrophenylsulfenyl)ethyl, 2-(diphenylphosphino)-ethyl, and nitroethyl. For a general description of protecting groups and their use, see T. W. Greene, Protective Groups in Organic Synthesis, John Wiley & Sons, New York, 1991.

The term "stereoisomer" refers to compounds, which have identical chemical composition, but differ with regard to arrangement of the atoms and the groups in space. These include enantiomers, diastereomers, geometrical isomers, atropisomer or conformational isomers.

All the stereoisomers of compounds described herein are within the scope of this invention. Racemic mixtures are also encompassed within the scope of this invention. Therefore, single stereochemical isomers as well enantiomeric, diastereoisomeric and geometric (or conformational) mixtures of the present compounds fall within the scope of the invention.

The term "tautomers" refers to compounds, which are characterized by relatively easy interconversion of isomeric forms in equilibrium. These isomers are intended to be covered by this invention.

The term "prodrug" refers to a compound, which is an inactive precursor of a compound, converted into its active form in the body by normal metabolic processes.

The term "ester" refers to a compound, which is formed by reaction between an acid and an alcohol with elimination of water. An ester can be represented by the formula RCOOR'.

Additionally the instant invention also includes the compounds which differ only in the presence of one or more isotopically enriched atoms for example replacement of Hydrogen with Deuterium and the like.

Pharmaceutically acceptable salts forming part of this invention include salts derived from inorganic bases such as Li, Na, K, Ca, Mg, Fe, Cu, Zn, and Mn; salts of organic bases such as N,N'-diacetylethylenediamine, glucamine, triethylamine, choline, hydroxide, dicyclohexylamine, metformin, benzylamine, trialkylamine, thiamine, and the like; chiral bases like alkylphenylamine, glycinol, and phenyl glycinol, salts of natural amino acids such as glycine, alanine, valine, leucine, isoleucine, norleucine, tyrosine, cystine, cysteine, methionine, proline, hydroxy proline, histidine, ornithine, lysine, arginine, and serine; quaternary ammonium salts of the compounds of invention with alkyl halides, and alkyl sulphates such as MeI and $(Me)_2SO_4$, non-natural amino acids such as D-isomers or substituted amino acids; guanidine, substituted guanidine wherein the substituents are selected from nitro, amino, alkyl, alkenyl, alkynyl, ammonium or substituted ammonium salts and aluminum salts. Salts may include acid addition salts where appropriate which are, sulphates, nitrates, phosphates, perchlorates, borates, hydrohalides, acetates, tartrates, maleates, citrates, fumarates, succinates, palmoates, methanesulphonates, benzoates, salicylates, benzenesulfonates, ascorbates, glycerophosphates, and ketoglutarates. Pharmaceutically acceptable solvates may be hydrates or comprise other solvents of crystallization such as alcohols.

Additionally the instant invention also includes the compounds which differ only in the presence of one or more isotopically enriched atoms for example replacement of hydrogen with deuterium.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, and swine; domestic animals such as rabbits, dogs, and cats; and laboratory animals including rodents, such as rats, mice and guinea pigs. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease, disorder or condition symptoms, preventing additional symptoms, ameliorating or preventing the underlying causes of symptoms, inhibiting the disease, disorder or condition, e.g., arresting the development of the disease, disorder or condition, relieving the disease, disorder or condition, causing regression of the disease, disorder or condition, relieving a condition caused by the disease, disorder or condition, or stopping the symptoms of the disease, disorder or condition either prophylactically and/or therapeutically.

As used herein, "amelioration" refers to an improvement in a disease or condition or at least a partial relief of symptoms associated with a disease or condition and As used herein, amelioration of the symptoms of a particular disease, disorder or condition by administration of a particular compound or pharmaceutical composition refers to any lessening of severity, delay in onset, slowing of progression, or shortening of duration, whether permanent or temporary, lasting or transient that are attributed to or associated with administration of the compound or composition.

The terms "inhibits", "inhibiting", or "inhibitor" of DHODH, as used herein, refer to inhibition of the enzyme DHODH.

By "pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutical composition" refers to a mixture of a compound capable of inhibiting DHODH as described herein with other chemical components, such as carriers, stabilizers, diluents, dispersing agents, suspending agents, thickening agents, and/or excipients. The pharmaceutical composition facilitates administration of the compound to an organism. The compound and pharmaceutical composition of the present invention can be administered by various routes of administration including, but not limited to, intravenous, oral, aerosol, parenteral, ophthalmic, pulmonary and topical administration.

The terms "effective amount" or "therapeutically effective amount," as used herein, refer to a sufficient amount of an agent or a compound being administered which will relieve to some extent one or more of the symptoms of the disease or condition being treated. The result is reduction and/or alleviation of the signs, symptoms, or causes of a disease, or any other desired alteration of a biological system. For example, an "effective amount" for therapeutic uses is the amount of the composition that includes a compound capable of inhibiting DHODH as described herein required to provide a clinically significant decrease in disease symptoms. In some embodiments, an appropriate "effective" amount in any individual case is determined using techniques, such as a dose escalation study.

The term "carrier," as used herein, refers to relatively nontoxic chemical compounds or agents that facilitate the incorporation of a compound into cells or tissues.

The term "diluent" refers to chemical compounds that are used to dilute the compound of interest prior to delivery. In some embodiments, diluents are used to stabilize compounds because they provide a more stable environment. Salts dissolved in buffered solutions (which also provide pH control or maintenance) are utilized as diluents, including, but not limited to a phosphate buffered saline solution.

As used herein, the term "immune" include cells of the immune system and cells that perform a function or activity in an immune response, such as, but not limited to, T-cells, B-cells, lymphocytes, macrophages, dendritic cells, neutrophils, eosinophils, basophils, mast cells, plasma cells, white blood cells, antigen presenting cells and natural killer cells.

As used herein, "cytokine" or "cytokines" refers to small soluble proteins secreted by cells that in some embodiments, alter the behavior or properties of the secreting cell or another cell. Cytokines bind to cytokine receptors and trigger a behavior or property within the cell, for example, cell proliferation, death or differentiation. Exemplary cytokines include, but are not limited to, interleukins (e.g., IL-2, IL-3, IL-4, IL-5, IL-6, IL-7, IL-8, IL-9, IL-10, IL-11, IL-12, IL-13, IL-15, IL-16, IL-17, IL-18, IL-1α, IL-1β, and IL-1 RA), granulocyte colony stimulating factor (G-CSF), granulocyte-macrophage colony stimulating factor (GM-CSF), oncostatin M, erythropoietin, leukemia inhibitory factor (LIF), interferons, B7.1 (also known as CD80), B7.2 (also known as B70, CD86), TNF family members (TNF-α, TNF-β, LT-β, CD40 ligand, Fas ligand, CD27 ligand, CD30 ligand, 4-1BBL, Trail), and MIF.

The compounds of the present invention are also useful in combination (administered together or sequentially) with known immunomodulators and/or anti-inflammatory agents useful in the treatment of autoimmune diseases, immune and inflammatory diseases, destructive bone disorders, malignant neoplastic diseases, angiogenic-related disorders, viral diseases, and infectious diseases such as

- Anti-TNF-alpha monoclonal antibodies such as Infliximab, Certolizumab pegol, Golimumab, Adalimumab and AME-527 from Applied Molecular Evolution,
- Antimetabolite compounds such as Mizoribine, Cyclophosphamide and Azathiopirine,
- Calcineurin (PP-2B) Inhibitors/INS Expression Inhibitors such as cyclosporine A, Tacrolimus and ISA-247 from Isotechnika,
- Cyclooxygenase Inhibitors such as Aceclofenac, Diclofenac, Celecoxib. Rofecoxib. Etoricoxib, Valdecoxib, Lumiracoxib, Cimicoxib and LAS-34475 from Laboratorios Almirall, S.A.,
- TNF-alpha Antagonists such as Etanercept, Lenercept, Onercept and Pegsunercept,
- NF-kappaB (NFKB) Activation Inhibitors such as Sulfasalazine and Iguratimod,
- IL-1 Receptor Antagonists such as Anakinra and AMG-719 from Amgen,
- Dihydrofolate Reductase (DHFR) Inhibitors such as Methrotexate, Aminopterin and CH-1504 from Chelsea,
- Inhibitors of Inosine 5'-Monophosphate Dehydrogenase (IMPDH) such as Mizorbine, Ribavirin, Tiazofurin, Amitivir, Mycophenolate mofetil, Ribamidine and Merimepodib,
- Glucocorticoids such as Prednisolone, Methylprednisolone, Dexamethasone, Cortisol, Hydrocortisone, Triamcinolone acetonide, Fluocinolone acetonide, Fluocinonide, Clocortolone pivalate, Hydrocortisone aceponate, Methylprednisolone suleptanate,
- Betamethasone butyrate propionate, Deltacortisone, Deltadehydrocortisone, Prednisone, Dexamethasone sodium phosphate, Triamcinolone, Betamethasone valerate, Betamethasone, Hydrocortisone sodium succinate, Prednisolone sodium phosphate, Hydrocortisone probutate and Difluprednate,
- Anti-CD20 monoclonal antibodies such as Rituximab, Ofatumumab, Ocrelizumab, Veltuzumab and TRU-015 from Trubion Pharmaceuticals,
- B-targeted cell therapies such as BLYSS, BAFF and TACI-Ig,
- p38 Inhibitors such as AMG-548 (from Amgen), ARRY-797 (from Array Biopharma), Chlormethiazole edisylate, Doramapimod, PS-540446, BMS-582949 (from BMS), SB-203580, SB-242235, SB-235699, SB-281832, SB-681323, SB-856553 (all from GlaxoSmithKline), KC-706 (from Kemia), LEO-1606, LEO-15520 (all from Leo), SC-80036, SD-06, PH-797804 (all from Pfizer), RWJ-67657 (from R. W. Johnson), RO-3201195, RO-4402257 (all from Roche), AVE-9940 (from Aventis). SCIO-323, SCIO-469 (all from Scios), TA-5493 (from Tanabe Seiyaku), and VX-745, VX-702 (all from Vertex).
- Jak3 Inhibitors such as CP690550 from Pfizer, R-348
- Syk inhibitors such as R-112, R-406 and Fostamatinib (R-788) all from Rigel,
- MEK inhibitors such as ARRY-142886, ARRY-438162 (all from Array Biopharma), AZD-6244 (from AstraZeneca), PD-098059, PD-0325901 (all from Pfizer), AR-119, AS703026
- P2X7 receptor antagonist such as AZD-9056 from AstraZeneca,
- S1 P1 agonists such as Fingolimod, CS-0777 from Sankyo and R-3477 from Actelion, ONO-4641, and KRP-203 from Novartis,
- Anti-CD49 monoclonal antibodies such as Natalizumab,
- Integrin Inhibitors such as Cilengitide, Firategrast, Valategrast hydrochloride, SB-273005, SB-683698 (all from Glaxo), HMR-1031 from Sanofi-Aventis, R-1295 from Roche, BMS-587101 from BMS and CDP-323 from UCB Celltech,
- Anti-CD88 monoclonal antibodies such as Eculizumab and Pexelizumab,
- IL-6 receptor antagonist such as CBP-1011 from InKine and C-326 from Amgen,
- (w) Anti IL-6 monoclonal antibodies such as Elsilimomab, CNTO-328 from Centocor and VX-30 from Vaccinex,
- Anti-CD152 monoclonal antibodies such as Ipilimumab and Ticilimumab,
- Fusion proteins comprising the extracellular domain of human cytotoxic T-lymphocyte-associated antigen 4 (CTLA-4) linked to portions of human immunoglobulin G1 such as Abatacept,
- Agents useful in the treatment of bone disorders such as Bisphosphonates such as Tiludronate disodium, Clodronate disodium, Disodium pamidronate, Etidronate disodium, Xydiphone (K1Na salt), Alendronate sodium, Neridronate, Dimethyl-APD, Olpadronic acid sodium salt, Minodronic acid, Apomine, Ibandronate sodium hydrate and Risedronate sodium,
- VEGF Try kinase inhibitors such as Pegaptanib octasodium, Vatalanib succinate,
- Sorafenib, Vandetanib, Sunitinib malate, Cediranib, Pazopanib hydrochloride and AE-941 from AEterna Zentaris,
- Other compounds efficacious in autoimmune diseases such as Gold salts, hydroxycloroquinine, Penicilamine, K-832, SMP114 and AD452,
- Purine-Nucleoside phosphorylase inhibitors such as Forodesine hydrochloride, R-3421 from Albert Einstein College of Medicine, CI-972 and CI-1000 both from Pfizer,
- Anti-RANKL monoclonal antibodies such as Denosumab,
- Anti-CD25 monoclonal antibodies such as Inolimomab, Dacliximab, Basiliximab and LMB-2 from the US National Cancer Institute,
- Histone Deacetylase (HDAC) Inhibitors such as Divalproex sodium, Acetyldinaline, Depsipeptide, Sodium butyrate, Sodium phenylbutyrate, Vorinostat, MS-27-275 from Mitsui, Valproic acid, Pyroxamide, Tributyrin, PX-105684 from TopoTarget, MG-0103 from MethylGene, G2M-777 from TopoTarget and CG-781 from Celera and
- Anti colony-stimulating factor (GM-CSF) monoclonal antibodies such as KB-002 from KaloBios.

The compounds of the invention are used for the treatment of rheumatoid arthritis, psoriatic arthritis, ankylosing spondilytis, multiple sclerosis, Wegener's granulomatosis, systemic lupus erythematosus, psoriasis and sarcoidosis it may be advantageous to use them in combination with other active compounds known to be useful in the treatment of such diseases such as rheumatoid arthritis, psoriatic arthritis, ankylosing spondilytis, multiple sclerosis, Wegener's granulomatosis, systemic lupus erythematosus, psoriasis and sarcoidosis.

The combinations of the invention may be used in the treatment of diseases and/or disorders wherein the inhibition of DHODH is known to show beneficial effect. Thus, the present application encompasses methods of treatment of these disorders, as well as the use of the combinations of the invention in the manufacture of a medicament for the treatment of these disorders.

The compounds of the present invention are also useful in combination (administered together or sequentially) with known anti-cancer treatments such as radiation therapy or with cytostatic or cytotoxic or anticancer agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidylate synthase inhibitors, such as 5-fluorouracil; and anti-metabolites, such as methotrexate, other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2) and other protein kinase modulators as well.

In some embodiments, diseases, disorders or conditions that are treated or prevented using compounds disclosed herein that are capable of inhibiting DHODH, compositions thereof, and methods provided herein to identify compounds capable of inhibiting DHODH, include diseases, conditions or disorders involving inflammation and/or that are related to the immune system. These diseases include but are not limited to asthma, chronic obstructive pulmonary disease, rheumatoid arthritis, inflammatory bowel disease, glomerulonephritis, neuroinflammatory diseases such as multiple sclerosis, and disorders of the immune system.

Thus, in some embodiments, inhibition of DHODH results in a method for treating immune and immune-related disorders, including, for example, chronic immune diseases/disorders, acute immune diseases/disorders, autoimmune and immunodeficiency diseases/disorders, diseases/disorders involving inflammation, organ transplant graft rejections and graft-versus-host disease and altered (e.g., hyperactive) immune responses.

Examples of immune disorders include psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

In other embodiments, compounds disclosed herein that are capable of inhibiting DHODH, compositions thereof, and methods provided herein to identify compounds capable of modulating DHODH inhibitors, are used in connection with treatment of malignancies, including, but not limited to, malignancies of lymphoreticular origin, bladder cancer, breast cancer, colon cancer, endometrial cancer, head and neck cancer, lung cancer, melanoma, ovarian cancer, prostate cancer and rectal cancer. DHODH is thought to play an important role in cell proliferation in cancer cells.

The following general methodology described herein provides the manner and process of making and using the compound of the present invention and are illustrative rather than limiting. Further modification of provided methodology and additionally new methods may also be devised in order to achieve and serve the purpose of the invention. Accordingly, it should be understood that there may be other embodiments which fall within the spirit and scope of the invention as defined by the specification hereto.

General Method of Preparation of Compounds of the Invention

The compounds of the present invention may be prepared by the following processes. Unless otherwise indicated, the variables (e.g. A, B, Cy, $R^1$, R, Y, $L_1$, X, $X_1$, $X_2$, $X_3$ and $L_2$) when used in the below formulae are to be understood to present those groups described above in relation to formula (I) to (IA).

Scheme 1:

This scheme provides a method for the preparation of a compound of formula (I) wherein A is a substituted or unsubstituted monocyclic aryl and substituted or unsubstituted monocyclic heteroaryl and other variables such as B, Cy, $R^1$, R, Y, $L_1$, X, $X_1$, $X_2$, $X_3$ and $L_2$ are the same as described above in relation to formula (I).

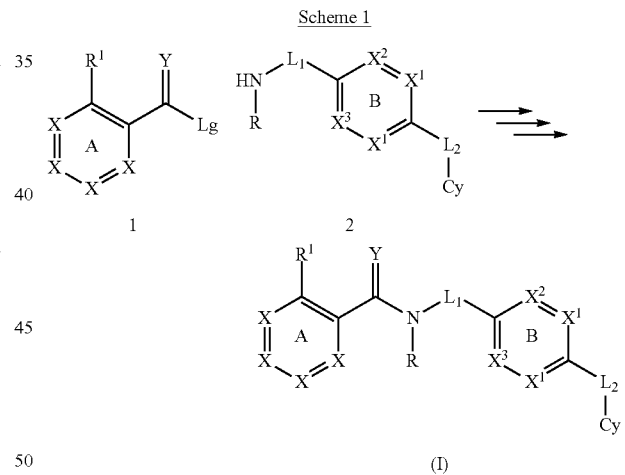

The compound of formula (1) wherein Lg is a leaving group such as hydroxyl or halogen, can be coupled with a compound of formula (2) in a suitable solvent using an amide coupling reagent such as DCC or optionally in the presence of a suitable base to give an intermediate (for example $R^1$ is COOEt) which can then be transformed either in single or multiple steps to the desired compound of formula (I), for example to $R^1$ is COOH wherein A is a substituted or unsubstituted monocyclic aryl or a substituted or unsubstituted monocyclic heteroaryl and other variables such as L, B, Cy, $R^2$, $R^3$, $R^4$, m and n are the same as described above in relation to formula (I).

Scheme 2:

This scheme provides a method for the preparation of a compound of formula (I) wherein $R^1$ is COOH, $L_2$ is absent, and other variables such as A, B, Cy, $R^1$, R, Y, $L_1$, X, $X_1$, $X_2$, and $X_3$ are the same as described above in relation to formula (I).

Scheme 2

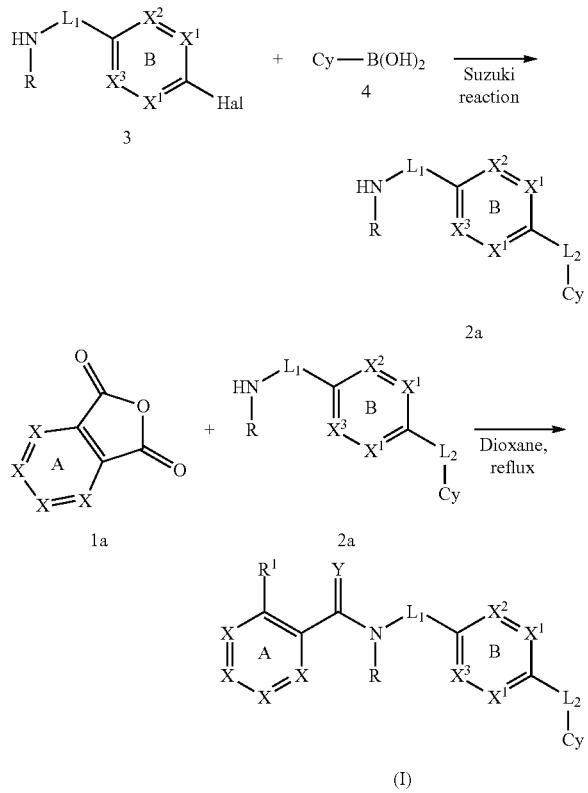

The compound of formula (3), wherein Hal represents halogen, can be coupled with a compound of formula (4) in the presence of $Pd(PPh_3)_4$ and a metal carbonate such as $K_2CO_3$ (Suzuki coupling) to give a compound of formula (2a). The compound of formula (2a) can be reacted with a suitable compound of formula (Ia) in the presence of a suitable solvent to give the desired compound of formula (I) wherein $R^1$ is COOH, $L_2$ is absent and other variables such as A, B, Cy, R, Y, $L_1$, X, $X_1$, $X_2$, and $X_3$ are the same as described above in relation to formula (I).

Scheme 3:

This scheme provides a method for the preparation of a compound of formula (I) wherein $R^1$ is COOH, $L_2$ is —O—, and other variables such as A, B, Cy, $R^1$, R, Y, $L_1$, X, $X_1$, $X_2$, $X_3$ and n are the same as described above in relation to formula (I).

Scheme 3

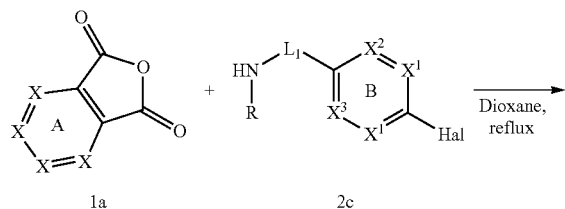

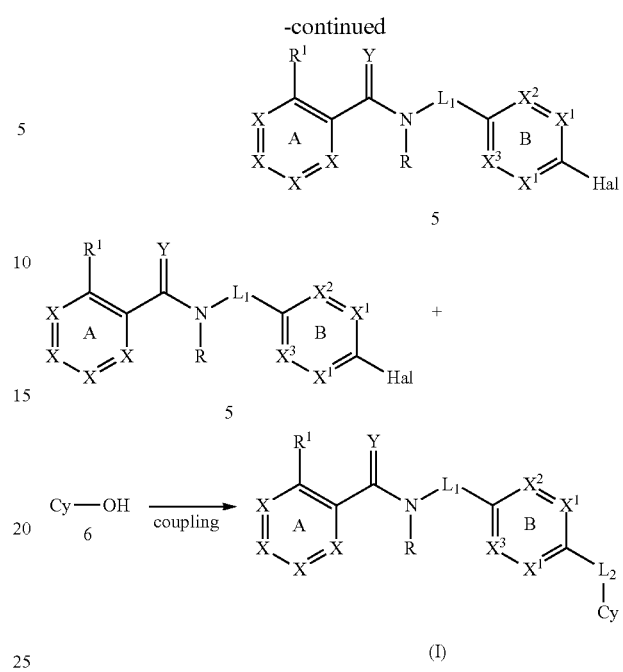

The compound of formula (1a) can be reacted with a suitable compound of formula (2a) wherein Hal represents halogen in the presence of a suitable solvent to give the desired compound of formula (5). The compound of formula (5) can be coupled with a compound of formula (6) in the presence of a suitable base such as $K_2CO_3$ to give the desired compound of formula (I) wherein $R^1$ is COOH, $L_2$ is —O— and other variables such as A, B, Cy, R, Y, $L_1$, X, $X_1$, $X_2$, and $X_3$ are the same as described above in relation to formula (I).

Similar methodologies with certain modifications as known to those skilled in the art can be used to synthesize compound of formula (I) or/and (IA), wherein the variables are to be understood to present those groups described above in relation to formula (I) or/and (IA), using suitable intermediates and reagents.

EXPERIMENTAL

Unless otherwise mentioned, work-up implies distribution of reaction mixture between the aqueous and organic phases indicated within parenthesis, separation and drying over $Na_2SO_4$ of the organic layer and evaporating the solvent to give a residue. Unless otherwise stated, purification is by column chromatography using silica gel as the stationary phase and a mixture of petroleum ether (boiling at 60-80° C.) and ethyl acetate or dichloromethane and methanol of suitable polarity as the mobile phases. RT refers to ambient temperature (25-28° C.).

General Procedure—for Suzuki Coupling:

To a solution of an aryl bromide (1 eq.) in dioxane and water (5:1) were added an arylboronic acid or an arylboronic acid pinacol ester (1.3 eq), tetrakis(triphenylphosphine)palladium(0)-(0.08 eq) and potassium carbonate (3.3 eq). The mixture was degassed with $N_2$ for 30 min. and refluxed until both the staRTing materials disappeared as monitored by TLC. Work-up ($H_2O$/AcOEt) and purification gave the desired product.

Intermediates 1, 4-27, 32-54, 56-63, 65-84 and 86-89 were prepared using general procedure-1.

Intermediate 1:
3,5-difluoro-3'-methoxybiphenyl-4-amine

The title compound (992 mg) was prepared from 2,6-difluoro-4-bromo aniline (1.1 g, 5.3 mmol) and 3-methoxyphenylboronic acid (1.04 g, 6.8 mmol) as a pale-yellow liquid. $^1$H-NMR (δ ppm, CDCl$_3$+DMSO-d$_6$, 400 MHz): 7.21-7.20 (m, 1H), 6.99-6.89 (m, 3H), 6.87-6.83 (m, 1H), 6.74-6.68 (m, 1H), 3.97 (bs, 2H), 3.69 (s, 3H).

Intermediate 2:
2-(3-methoxyphenyl)-5-nitropyridine

The title compound (612 mg) was prepared from 2-chloro-5-nitropyridine (500 mg, 3.15 mmol) and 3-methoxyphenylboronic acid (623 mg, 4.1 mmol) as a pale yellow solid. $^1$H-NMR (δ ppm, CDCl$_3$, 400 MHz): 9.50 (d, J 2.6, 1H), 8.53 (dd, J 2.6, 8.8, 1H), 7.91 (d, J 8.8, 1H), 7.69-7.68 (m, 1H), 7.63 (d, J 7.8, 1H), 7.44 (t, J 7.9, 1H), 7.08-7.05 (m, 1H), 3.91 (s, 3H).

Intermediate 3:
6-(3-methoxyphenyl)pyridin-3-amine

Iron powder (739 mg, 13.24 mmol) and ammonium chloride (100 mg, 3.18 mmol) were added to a solution of intermediate 2 (610 mg, 2.65 mmol) in EtOH/H$_2$O (2:1, 15 mL) and the mixture refluxed for one hour. The mixture was filtered through celite and celite washed with ethanol. Work-up (H$_2$O/AcOEt) and concentration of the combined layers afforded intermediate 3 (330 mg) as a waxy solid. $^1$H-NMR (δ ppm, DMSO-d$_6$, 400 MHz): 8.00 (d, J 2.7, 1H), 7.61 (d, J 8.5, 1H), 7.47-7.45 (m, 2H), 7.27 (t, J 8, 1H), 6.97 (dd, J 2.8, 8.5, 1H), 6.83-6.81 (m, 1H), 5.46 (s, 2H), 3.78 (s, 3H).

Intermediate 4: 3'-ethoxy-3-fluorobiphenyl-4-amine

The title compound (1.34 g) was prepared from 2-fluoro-4-bromo aniline (2.5 g, 13.1 mmol) and 3-ethoxyphenylboronic acid (2.8 g, 17.0 T mmol) as a pale-yellow liquid. $^1$H-NMR (δ ppm, DMSO-d$_6$, 400 MHz): 7.38-7.20 (m, 3H), 7.10 (d, J 7.9, 1H), 7.07-7.05 (m, 1H), 6.83-6.76 (m, 2H), 5.24 (s, 2H), 4.06 (q, J 7, 2H), 1.32 (t, J 7, 3H).

Intermediate 5:
3'-ethoxy-3,5-difluorobiphenyl-4-amine

The title compound (0.219 g) was prepared from 2,6-difluoro-4-bromo aniline (0.5 g, 2.4 mmol) and 3-ethoxyphenylboronic acid (0.517 g, 3.12 mmol) as a pale-yellow liquid. $^1$H-NMR (δ ppm, DMSO-d$_6$, 400 MHz): 7.30-7.24 (m, 3H), 7.14 (d, J 7.9, 1H), 7.11 (s, 1H), 6.82 (dd, J 2.1, 8.1, 1H), 5.31 (s, 2H), 4.07 (q, J 7, 2H), 1.32 (t, J 7, 3H).

Intermediate 6:
2'-chloro-3,5-difluorobiphenyl-4-amine

The title compound (0.140 g) was prepared from 2,6-difluoro-4-bromo aniline (0.22 g, 1.06 mmol) and 2-chlorophenylboronic acid (0.21 g, 1.38 mmol) as a white solid. $^1$H-NMR (δ ppm, DMSO-d$_6$, 400 MHz): 7.52-7.50 (m, 1H), 7.40-7.35 (m, 3H), 7.00 (d, J 2.1, 7.6, 2H), 5.39 (s, 2H).

Intermediate 7: 3,5-difluorobiphenyl-4-amine

The title compound (0.401 g) was prepared from 2,6-difluoro-4-bromo aniline (0.5 g, 2.4 mmol) and phenylboronic acid (0.38 g, 3.12 mmol) as a white solid. $^1$H-NMR (δ ppm, DMSO-d$_6$, 400 MHz): 7.60 (d, J 7.4, 2H), 7.38 (t, J 7.5, 2H), 7.30-7.25 (m, 3H), 5.33 (s, 2H).

Intermediate 8: 3,5-difluoro-3'-(trifluoromethoxy)biphenyl-4-amine

The title compound (0.812 g) was prepared from 2,6-difluoro-4-bromo aniline (1 g, 4.8 mmol) and 3-(trifluoromethoxy)phenylboronic acid (1.28 g, 6.24 mmol) as a colourless liquid.

Intermediate 9:
3'-(benzyloxy)-3,5-difluorobiphenyl-4-amine

The title compound (0.143 g) was prepared from 2,6-difluoro-4-bromo aniline (0.3 g, 1.4 mmol) and 3-(benzyloxy)phenylboronic acid (0.426 g, 1.8 mmol) as a colourless liquid. $^1$H-NMR (δ ppm, DMSO-d$_6$, 400 MHz): 7.49-7.44 (m, 2H), 7.39 (t, J 7.2, 2H), 7.35-7.26 (m, 4H), 7.24 (s, 1H), 7.18 (d, J 7.8, 1H), 6.91 (dd, J 1.9, 8.0, 1H), 5.33 (s, 2H), 5.16 (s, 2H).

Intermediate 10:
3-chloro-3'-ethoxy-5-fluorobiphenyl-4-amine

The title compound (0.360 g) was prepared from 4-bromo-2-chloro-6-fluoroaniline (0.5 g, 2.0 mmol) and 3-ethoxyphenylboronic acid (0.441 g, 2.65 mmol) as a yellow liquid. $^1$H-NMR (δ ppm, DMSO-d$_6$, 400 MHz): 7.43-7.38 (m, 2H), 7.27 (t, J 7.9, 1H), 7.14 (d, J 7.9, 1H), 7.10 (s, 1H), 6.82 (dd, J 2.1, 8.1, 1H), 5.51 (s, 2H), 4.07 (q, J 7, 2H), 1.32 (t, J 7, 3H).

Intermediate 11:
3,5-dichloro-3'-methoxybiphenyl-4-amine

The title compound (0.550 g) was prepared from 2,6-dichloro-4-bromoaniline (0.5 g, 2.0 mmol) and 3-methoxyphenylboronic acid (0.409 g, 2.69 mmol) as a white solid. $^1$H-NMR (δ ppm, DMSO-d$_6$, 400 MHz): 7.58 (s, 2H), 7.29 (t, J 7.8, 1H), 7.18-7.10 (m, 2H), 6.85 (dd, J 2, 8.1, 1H), 5.63 (s, 2H), 3.81 (s, 3H).

Intermediate 12:
3-chloro-5-fluoro-3'-propoxybiphenyl-4-amine

The title compound (0.273 g) was prepared from 4-bromo-2-chloro-6-fluoroaniline (0.5 g, 2.2 mmol) and 3-propoxyphenylboronic acid (0.521 g, 2.9 mmol) as a yellow liquid. $^1$H-NMR (δ ppm, DMSO-d$_6$, 400 MHz): 7.44-7.39 (m, 3H), 7.27 (t, J 7.9, 1H), 7.16-7.10 (m, 2H), 5.51 (s, 2H), 3.97 (t, J 6.5, 2H), 1.75-1.70 (m, 2H), 0.98 (t, J 7.9, 3H).

Intermediate 13:
3-chloro-2',5-difluorobiphenyl-4-amine

The title compound (0.392 g) was prepared from 4-bromo-2-chloro-6-fluoroaniline (0.5 g, 2.2 mmol) and 2-fluorophenylboronic acid (0.363 g, 2.6 mmol) as a pale-yellow liquid. $^1$H-NMR (δ ppm, DMSO-d$_6$, 400 MHz): 7.51 (td, J 1.7, 7.8, 1H), 7.38-7.32 (m, 1H), 7.28 (s, 2H), 7.27-7.22 (m, 2H), 5.62 (s, 2H).

Intermediate 14:
3,5-dichloro-3'-ethoxybiphenyl-4-amine

The title compound (0.550 g) was prepared from 4-Bromo-2,6-dichloroaniline (0.5 g, 2.2 mmol) and 3-ethoxyphenylboronic acid (0.447 g, 2.7 mmol) as a yellow liquid which was about 70% pure as adjudged by $^1$H-NMR data. $^1$H-NMR (δ ppm, DMSO-d$_6$, 400 MHz): 7.56 (s, 2H), 7.28 (s, 1H), 7.16-7.08 (m, 2H), 6.83 (dd, J 2, 8.1, 1H), 5.62 (s, 2H), 4.10 (q, J 7, 2H), 1.32 (t, J 7, 3H).

Intermediate 15: 3-fluoro-3'-(trifluoromethoxy)biphenyl-4-amine

The title compound (0.5 g) was prepared from 4-Bromo-2-fluoroaniline (1 g, 5.3 mmol) and 3-(trifluoromethoxy) phenylboronic acid (1.4 g, 6.8 mmol) as a yellow liquid. $^1$H-NMR (δ ppm, DMSO-d$_6$, 400 MHz): 7.62 (d, J 8, 1H), 7.53 (s, 1H), 7.48 (t, J 8, 1H), 7.42 (dd, J 2, 9.1, 1H), 7.28 (dd, J 2, 8.3, 1H), 7.23 (d, J 11, 1H), 6.82 (t, J 8.5, 1H), 5.40 (s, 2H).

Intermediate 16: 2'-fluoro-3-(trifluoromethoxy)biphenyl-4-amine

The title compound (0.294 g) was prepared from 2-trifluoromethoxy-4-bromo aniline (0.5 g, 1.9 mmol) and 2-fluorophenylboronic acid (0.345 g, 2.5 mmol) as a yellow liquid. $^1$H-NMR (δ ppm, DMSO-d$_6$, 400 MHz): 7.47 (td, J 1.2, 4.7, 1H), 7.33-7.20 (m, 5H), 6.89 (d, J 8.8, 1H), 5.62 (s, 2H).

Intermediate 17: 3,5-dichloro-2'-fluorobiphenyl-4-amine

The title compound (0.367 g) was prepared from 4-Bromo-2,6-dichloro aniline (0.5 g, 1.9 mmol) and 2-fluorophenylboronic acid (0.363 g, 2.6 mmol) as a white solid. $^1$H-NMR (δ ppm, DMSO-d$_6$, 400 MHz): 7.50 (t, J 6.3, 1H), 7.43 (s, 2H), 7.39-7.31 (m, 1H), 7.29-7.21 (m, 2H), 5.73 (s, 2H).

Intermediate 18: 3,5-difluoro-3'-isopropoxybiphenyl-4-amine

The title compound (0.34 g) was prepared from 4-Bromo-2,6-difluoro aniline (0.5 g, 2.4 mmol) and 3-isopropoxyphenylboronic acid (0.337 g, 3.1 mmol) as a red liquid. $^1$H-NMR (δ ppm, DMSO-d$_6$, 400 MHz): 7.30-7.22 (m, 3H), 7.16-7.07 (m, 2H), 6.89 (dd, J 2.3, 8.1, 1H), 5.32 (s, 2H), 4.68 (septet, J 6, 1H), 1.26 (d, J 6, 6H).

Intermediate 19: 3,5-difluoro-3'-propoxybiphenyl-4-amine

The title compound (0.3 g) was prepared from 4-Bromo-2,6-difluoro aniline (0.5 g, 2.4 mmol) and 3-propoxyphenylboronic acid (0.337 g, 3.1 mmol) as a red liquid. $^1$H-NMR (δ ppm, DMSO-d$_6$, 400 MHz): 7.30-7.24 (m, 3H), 7.18-7.10 (m, 2H), 6.86-6.80 (m, 1H), 5.31 (s, 2H), 3.97 (t, J 6.5, 2H), 1.75-1.65 (m, 2H), 0.98 (t, J 7.4, 3H).

Intermediate 20: 2',3-dichloro-5-fluorobiphenyl-4-amine

The title compound (0.260 g) was prepared from 4-bromo-2-chloro-6-fluoroaniline (0.5 g, 2.4 mmol) and 2-chlorophenylboronic acid (0.453 g, 2.9 mmol) as a white solid. $^1$H-NMR (δ ppm, DMSO-d$_6$, 400 MHz): 7.60 (d, J 7.3, 1H), 7.42-7.31 (m, 3H), 7.18-7.11 (m, 2H), 5.6 (s, 2H).

Intermediate 21: 3'-butoxy-3-chloro-5-fluorobiphenyl-4-amine

The title compound (0.190 g) was prepared from 4-bromo-2-chloro-6-fluoroaniline (0.2 g, 0.89 mmol) and 3-butoxyphenylboronic acid (0.224 g, 1.16 mmol) as a yellow solid. $^1$H-NMR (δ ppm, DMSO-d$_6$, 400 MHz): 7.44-7.41 (m, 2H), 7.27 (t, J 7.9, 1H), 7.17-7.10 (m, 2H), 6.81-6.84 (m, 1H), 5.50 (s, 2H), 4.01 (t, J 5.3, 2H), 1.72-1.65 (m, 2H), 1.50-1.41 (m, 2H), 0.93 (t, J 7.4, 3H).

Intermediate 22: 3-chloro-5-fluoro-3'-isobutoxybiphenyl-4-amine

The title compound (0.180 g) was prepared from 4-bromo-2-chloro-6-fluoroaniline (0.2 g, 0.89 mmol) and 3-isobutoxyphenylboronic acid (0.224 g, 1.16 mmol) as a yellow solid. $^1$H-NMR (δ ppm, DMSO-d$_6$, 400 MHz): 7.44-7.41 (m, 2H), 7.27 (t, J 7.9, 1H), 7.17-7.10 (m, 2H), 6.84-6.81 (m, 1H), 5.50 (s, 2H), 3.83 (d, J 6.5, 2H), 2.07-1.97 (m, 1H), 1.00 (d, J 6.7, 6H).

Intermediate 23: 2',3,5-trifluorobiphenyl-4-amine

The title compound (0.492 g) was prepared from 4-bromo-2,6-difluoroaniline (0.5 g, 2.4 mmol) and 2-fluorophenylboronic acid (0.436 g, 3.12 mmol) as a yellow liquid. $^1$H-NMR (δ ppm, DMSO-d$_6$, 400 MHz): 7.51 (td, J 1.5, 7.9, 1H), 7.38-7.31 (m, 1H), 7.29-721 (m, 2H), 7.14 (d, J 8.6, 2H), 5.44 (s, 2H).

Intermediate 24: 2',3,5-trichlorobiphenyl-4-amine

The title compound (0.4 g) was prepared from 4-bromo-2,6-dichloroaniline (0.5 g, 2.1 mmol) and 2-chlorophenylboronic acid (0.421 g, 2.7 mmol) as a white solid. $^1$H-NMR (δ ppm, DMSO-d$_6$, 400 MHz): 7.55-7.50 (m, 1H), 7.40-7.32 (m, 3H), 7.29 (s, 2H), 5.72 (s, 2H).

Intermediate 25: 3,5-difluoro-3'-isobutoxybiphenyl-4-amine

The title compound (0.16 g) was prepared from 4-bromo-2,6-difluoroaniline (0.2 g, 0.96 mmol) and 3-isobutoxyphenylboronic acid (0.242 g, 1.2 mmol) as a yellow liquid.

Intermediate 26: 3,5-difluoro-3'-butoxybiphenyl-4-amine

The title compound (0.104 g) was prepared from 4-bromo-2,6-difluoroaniline (0.2 g, 0.96 mmol) and 3-butoxyphenylboronic acid (0.242 g, 1.2 mmol) as a colourless liquid.

Intermediate 27: 3-chloro-5-fluoro-3'-(trifluoromethoxy)biphenyl-4-amine

The title compound (0.280 g) was prepared from 4-bromo-2-chloro-6-difluoroaniline (0.5 g, 2.27 mmol) and 3-(trifluoromethoxy)phenylboronic acid (0.6 g, 2.89 mmol) as a pale-yellow liquid. $^1$H-NMR (δ ppm, DMSO-d$_6$, 400 MHz): 7.68-7.64 (m, 1H), 7.62 (s, 1H), 7.53-7.46 (m, 3H) 7.29-7.22 (m, 1H), 5.64 (s, 2H).

Intermediate 28: 5-(benzyloxy)-1,3-difluoro-2-nitrobenzene

Potassium carbonate (544 mg, 3.94 mmol) and benzyl alcohol (0.3 ml, 2.8 mmol) were added to a solution of 2,4,6-trifluoronitrobenzene (500 mg, 2.8 mmol) in DMF (5 ml). This mixture was stirred at RT overnight. Work up (EtOAc/H₂O) afforded the title compound (521 mg) as a yellow liquid which was used in the next step without fuRTher purification.

Intermediate 29: 4-(benzyloxy)-2,6-difluoroaniline

Iron powder (502 mg, 9 mmol) and ammonium chloride (192 mg, 3.6 mmol) were added to a solution of intermediate 28 (500 mg, 1.8 mmol) in EtOH/H₂O (2:1, 15 mL) and the mixture refluxed for two hours. The mixture was filtered through celite and celite washed with ethanol. Work-up (H₂O/AcOEt) from the combined filtrates and purification of afforded the title compound (24 mg) as a colourless liquid. ¹H-NMR (δ ppm, DMSO-d₆, 400 MHz): 7.42-7.36 (m, 3H), 7.35-7.28 (m, 2H), 6.68 (dd, J 1.6, 8.8, 2H), 4.97 (s, 2H), 4.64 (s, 2H).

Intermediate 30:1-bromo-3-(cyclopentyloxy)benzene

Potassium carbonate (400 mg, 2.8 mmol) was added to 3-Bromophenol (500 mg, 2.8 mmol) dissolved in acetonitrile and the mixture was refluxed for 1 h and cooled to RT. cyclopentyl bromide (430 mg, 2.8 mmol) was added and the mixture refluxed again overnight. Work up (H₂O/EtOAc) and purification afforded the title compound as a pale-yellow liquid. ¹H-NMR (δ ppm, CDCl₃, 400 MHz): 7.11 (t, J 8.3, 1H), 7.05-7.00 (m, 2H), 6.82-6.76 (m, 1H), 4.76-4.68 (m, 1H), 1.94-1.73 (m, 6H), 1.65-1.54 (m, 2H).

Intermediate 31: 2-(3-(cyclopentyloxy)phenyl)-4,4,5,5-tetramethyl-1,3,2-dioxaborolane A mixture of intermediate 30 (335 mg, 1.4 mmol), bis(pinacolato)diboron (351 mg, 1.4 mmol) and potassium acetate (450 mg, 4.6 mmol) in dioxane was degassed with N₂ for 30 min. Tetrakis(triphenylphosphine)palladium (0) (128 mg, 0.11 mmol) was added and the degassing continued again for fuRTher 15 min. This mixture was refluxed overnight. After completion of the reaction, work up (H₂O/EtOAc) and column purification afforded the title compound (165 mg) as a yellow liquid.

Intermediate 32: 3'-(cyclopentyloxy)-3,5-difluorobiphenyl-4-amine

The title compound (22 mg) was prepared from 4-bromo-2,6-difluoroaniline (165 mg, 0.6 mmol) and intermediate 31 (120 mg, 0.6 mmol) as a pale-yellow liquid. ¹H-NMR (δ ppm, DMSO-d₆, 400 MHz): 7.29-7.22 (m, 3H), 7.12 (d, J 8, 1H), 7.06 (s, 1H), 6.82-6.76 (m, 1H), 5.30 (s, 2H), 4.96-4.88 (m, 1H), 1.96-1.82 (m, 2H), 1.75-1.65 (m, 4H), 1.60-1.51 (m, 2H).

Intermediate 33: 3-chloro-3'-(cyclopentyloxy)-5-fluorobiphenyl-4-amine

The title compound (450 mg) was prepared from 4-bromo-2-chloro-6-fluoroaniline (600 mg, 2.7 mmol) and intermediate 31 (1 g, 3.4 mmol) as a yellow liquid. ¹H-NMR (δ ppm, DMSO-d₆, 400 MHz): 7.42-7.36 (m, 2H), 7.26 (t, J 8, 1H), 7.11 (d, J 7.8, 1H), 7.08-7.05 (m, 1H), 6.80 (dd, J 2.3, 8.1, 1H), 5.49 (s, 2H), 4.92-4.84 (m, 1H), 1.97-1.87 (m, 2H), 1.77-1.62 (m, 4H), 1.60-1.50 (m, 2H).

Intermediate 34: 3'-(difluoromethoxy)-3,5-difluorobiphenyl-4-amine

The title compound (144 mg) was prepared from 4-bromo-2,6-difluoroaniline (200 mg, 0.96 mmol) and 3-(difluoromethoxy)phenylboronic acid (234 mg, 1.25 mmol) as a white solid. ¹H-NMR (δ ppm, DMSO-d₆, 400 MHz): 7.49 (d, J 7.9, 1H), 7.43-7.39 (m, 2H), 7.38-7.30 (m, 2H), 7.32 (t, J 74, 1H), 7.06 (dd, J 1.8, 7.9, 1H), 5.42 (s, 2H).

Intermediate 35: 2-[3'-(difluoromethoxy)-3,5-difluorobiphenyl-4-ylcarbamoyl]benzoic acid The title compound (155 mg) was prepared from 4-bromo-2-chloro-6-fluoroaniline (89 mg, 1.16 mmol) and 3-(difluoromethoxy)phenylboronic acid (217 mg, 1.16 mmol) as a white solid. ¹H-NMR (δ ppm, DMSO-d₆, 400 MHz): 7.52-7.47 (m, 3H), 7.46-7.44 (m, 1H), 7.43-7.40 (m, 2H), 7.32 (t, J 74.2, 1H), 5.60 (s, 2H).

Intermediate 36: 2'-chloro-3,5-difluoro-5'-methoxybiphenyl-4-amine

The title compound (97 mg) was prepared from 4-bromo-2,6-difluoroaniline (100 mg, 0.48 mmol) and 2-chloro-5-methoxyphenylboronic acid (116 mg, 0.62 mmol) as a yellow solid. ¹H-NMR (δ ppm, DMSO-d₆, 400 MHz): 7.40 (d, J 9.6, 1H), 7.02 (d, J 7.7, 2H), 6.92 (s, 2H), 5.39 (s, 2H), 3.77 (s, 3H).

Intermediate 37: 3,3',5-trifluoro-5'-methoxybiphenyl-4-amine

The title compound (51 mg) was prepared from 4-bromo-2,6-difluoroaniline (100 mg, 0.48 mmol) and 3-fluoro-5-methoxyphenylboronic acid (106 mg, 0.62 mmol) as a yellow solid. ¹H-NMR (δ ppm, DMSO-d₆, 400 MHz): 7.35 (dd, J 2.1, 8.1, 2H), 7.06 (d, J 10.2, 1H), 7.01 (s, 1H), 6.71 (dd, J 2, 8.8, 1H), 5.42 (s, 2H), 3.81 (s, 3H).

Intermediate 38: 4-(benzo[d][1,3]dioxol-5-yl)-2,6-difluoroaniline

The title compound (143 mg) was prepared from 4-bromo-2,6-difluoroaniline (200 mg, 0.96 mmol) and benzo[d][1,3]dioxol-5-ylboronic acid (207 mg, 1.25 mmol) as a white solid. ¹H-NMR (δ ppm, DMSO-d₆, 400 MHz): 7.23-7.18 (m, 3H), 7.08 (dd, J 1.8, 8.2, 1H), 6.91 (d, J 8.1, 1H), 6.01 (s, 2H), 5.24 (s, 2H).

Intermediate 39: 4-(benzo[d][1,3]dioxol-5-yl)-2-chloro-6-fluoroaniline

The title compound (143 mg) was prepared from 4-bromo-2-chloro-6-fluoroaniline (200 mg, 0.89 mmol) and benzo[d][1,3]dioxol-5-ylboronic acid (192 mg, 1.16 mmol) as a white solid. ¹H-NMR (δ ppm, DMSO-d₆, 400 MHz): 7.36-7.30 (m, 2H), 7.20 (d, J 1.7, 1H), 7.06 (dd, J 1.4, 8.1, 1H), 6.91 (d, J 8.1, 1H), 6.01 (s, 2H), 5.42 (s, 2H).

Intermediate 40: 3,5-difluoro-3',4'-dimethoxybiphenyl-4-amine

The title compound (39 mg) was prepared from 4-bromo-2,6-difluoroaniline (100 mg, 0.48 mmol) and 3,4-dimethoxyphenylboronic acid (113 mg, 0.62 mmol) as a pale-yellow solid. ¹H-NMR (δ ppm, DMSO-d₆, 400 MHz): 7.25 (dd, J 2, 8.3, 2H), 7.18-7.10 (m, 2H), 6.94 (d, J 8.4, 1H), 5.21 (s, 2H), 3.81 (s, 3H), 3.75 (s, 3H).

Intermediate 41: 3-chloro-3',5-difluoro-5'-methoxybiphenyl-4-amine

The title compound (71 mg) was prepared from 4-bromo-2-chloro-6-fluoroaniline (100 mg, 0.44 mmol) and 3-fluoro- 5-methoxyphenylboronic acid (97 mg, 0.57 mmol) as a pale-yellow solid. $^1$H-NMR (δ ppm, DMSO-d$_6$, 400 MHz): 7.51-7.45 (m, 2H), 7.05 (d, J 10.3, 1H), 7.00 (s, 1H), 6.73 (dd, J 2.1, 4.2, 1H), 5.60 (s, 2H), 3.81 (s, 3H).

Intermediate 42: 3,3'-dichloro-5-fluoro-5'-methoxy-biphenyl-4-amine

The title compound (41 mg) was prepared from 4-bromo-2-chloro-6-fluoroaniline (100 mg, 0.44 mmol) and 3-chloro-5-methoxyphenylboronic acid (107 mg, 0.57 mmol) as a pale-yellow solid.

Intermediate 43: 4-(2,3-dihydrobenzofuran-5-yl)-2,6-difluoroaniline

The title compound (182 mg) was prepared from 4-bromo-2,6-difluoroaniline (200 mg, 0.96 mmol) and 2,3-dihydrobenzofuran-5-ylboronic acid (204 mg, 1.25 mmol) as a white solid. $^1$H-NMR (δ ppm, DMSO-d$_6$, 400 MHz): 7.46 (s, 1H), 7.30 (dd, J 1.8, 8.3, 1H), 7.16 (dd, J 2.1, 8.2, 2H), 6.75 (d, J 8.3, 1H), 5.18 (s, 2H), 4.52 (t, J 8.7, 2H), 3.18 (t, J 8.5, 2H).

Intermediate 44: 2-chloro-4-(2,3-dihydrobenzofuran-5-yl)-6-fluoroaniline

The title compound (86 mg) was prepared from 4-bromo-2-chloro-6-fluoroaniline (200 mg, 0.89 mmol) and 2,3-dihydrobenzofuran-5-ylboronic acid (189 mg, 1.16 mmol) as a pale-yellow solid. $^1$H-NMR (δ ppm, DMSO-d$_6$, 400 MHz): 7.46 (s, 1H), 7.33-7.25 (m, 3H), 6.75 (d, J 8.3, 1H), 5.36 (s, 2H), 4.52 (t, J 8.7, 2H), 3.18 (t, J 8.6, 2H).

Intermediate 45: 4-(1,3-dimethyl-1H-indazol-5-yl)-2,6-difluoroaniline

Potassium acetate (0.344 g, 3.51 mmol) and bis(pinacolato)diboron (351 mg, 1.4 mmol) were added to a solution of 5-bromo-1,3-dimethyl-1H-indazole (240 mg, 1.06 mmol) in dioxane (10 ml) and mixture was degassed with nitrogen for 30 min. tetrakis(triphenylphosphine) palladium(0) was added and degassed for further 30 min. Reaction mixture was refluxed for 2 h. After completion of the reaction, work-up (AcOEt/H$_2$O) followed by column afforded 1,3-dimethyl-5-(4,4,5,5-tetramethyl-1,3,2-dioxaborolan-2-yl)-1H-indazole (85 mg) as a white solid. The title compound (26 mg) was prepared from 4-bromo-2,6-difluoroaniline (50 mg, 0.24 mmol) and 1,3-dimethyl-5-(4,4,5,5-tetramethyl-1,3,2-dioxaborolan-2-yl)-1H-indazole (85 mg, 0.31 mmol) as a white solid. $^1$H-NMR (δ ppm, DMSO-d$_6$, 400 MHz): 7.93 (s, 1H), 7.66 (dd, J 1.5, 8.8, 1H), 7.55 (d, J 8.8, 1H), 7.33 (dd, J 2, 8.2, 2H), 5.22 (s, 2H), 3.94 (s, 3H), 2.49 (s, 3H).

Intermediate 46: 3'-chloro-3,5-difluoro-5'-methoxy-biphenyl-4-amine

The title compound (39 mg) was prepared from 4-bromo-2,6-difluoroaniline (100 mg, 0.48 mmol) and 3-chloro-5-methoxyphenylboronic acid (116 mg, 0.62 mmol) as a pale-yellow solid. $^1$H-NMR (δ ppm, DMSO-d$_6$, 400 MHz): 7.36 (dd, J 2.2, 8.1, 2H), 7.25 (s, 1H), 7.12 (s, 1H), 6.91 (t, J 1.9, 1H), 5.43 (s, 2H), 3.81 (s, 3H).

Intermediate 47: 3-chloro-5-fluoro-3',4'-dimethoxy-biphenyl-4-amine

The title compound (39 mg) was prepared from 4-bromo-2-chloro-6-fluoroaniline (100 mg, 0.442 mmol) and 3,4-dimethoxyphenylboronic acid (80 mg, 0.62 mmol) as a pale-yellow solid.

Intermediate 48: 2',3-dichloro-5-fluoro-5'-methoxy-biphenyl-4-amine

The title compound (39 mg) was prepared from 4-bromo-2-chloro-6-fluoroaniline (100 mg, 0.44 mmol) and 2-chloro-5-methoxyphenylboronic acid (106 mg, 0.62 mmol) as a pale-yellow solid.

Intermediate 49: 2',3,5-trifluoro-5'-methoxybiphenyl-4-amine

The title compound (31 mg) was prepared from 4-bromo-2,6-difluoroaniline (100 mg, 0.48 mmol) and 2-fluoro-5-methoxyphenylboronic acid (106 mg, 0.62 mmol) as a pale-yellow solid.

Intermediate 50: 4'-chloro-3,5-difluoro-3'-methoxy-biphenyl-4-amine

The title compound (81 mg) was prepared from 4-bromo-2,6-difluoroaniline (100 mg, 0.48 mmol) and 4-chloro-5-methoxyphenylboronic acid (116 mg, 0.62 mmol) as a white solid.

Intermediate 51: 3,4'-dichloro-5-fluoro-3'-methoxy-biphenyl-4-amine

The title compound (82 mg) was prepared from 4-bromo-2-chloro-6-fluoroaniline (100 mg, 0.44 mmol) and 4-chloro-5-methoxyphenylboronic acid (107 mg, 0.62 mmol) as a pale-yellow solid.

Intermediate 52: 3-chloro-2',5-difluoro-5'-methoxy-biphenyl-4-amine

The title compound (70 mg) was prepared from 4-bromo-2-chloro-6-fluoroaniline (100 mg, 0.44 mmol) and 2-fluoro-5-methoxyphenylboronic acid (98 mg, 0.58 mmol) as a white solid. $^1$H-NMR (δ ppm, DMSO-d$_6$, 400 MHz): 7.30-7.24 (m, 2H), 7.17 (t, J 9.1, 1H), 7.02-6.97 (m, 1H), 6.90-6.84 (m, 1H), 5.61 (s, 2H), 3.77 (s, 3H).

Intermediate 53: 3,4',5-trifluoro-3'-methoxybiphenyl-4-amine

The title compound (480 mg) was prepared from 4-bromo-2,6-difluoroaniline (200 mg, 0.96 mmol) and 4-fluoro-5-methoxyphenylboronic acid (210 mg, 1.24 mmol) as a white solid. $^1$H-NMR (δ ppm, DMSO-d$_6$, 400 MHz): 7.39-7.29 (m, 3H), 7.21-7.12 (m, 2H), 5.33 (s, 2H), 3.90 (s, 3H).

Intermediate 54: 2,6-difluoro-4-(3-methyl-1H-indol-5-yl)aniline

The title compound (68 mg) was prepared from 4-bromo-2,6-difluoroaniline (100 mg, 0.48 mmol) and 3-methyl-5-(4,4,5,5-tetramethyl-1,3,2-dioxaborolan-2-yl)-1H-indole (160 mg, 0.62 mmol) as a white solid. $^1$H-NMR (δ ppm, DMSO-d$_6$, 400 MHz): 10.71 (s, 1H), 7.67 (s, 1H), 7.33-7.29 (m, 2H), 7.28-7.21 (m, 2H), 7.09 (s, 1H), 5.12 (s, 2H), 2.27 (s, 3H).

Intermediate 55: 2,6-difluoro-4-(3-methyl-1H-indazol-5-yl)aniline

Following the general procedure-1, tert-butyl 5-(4-amino-3,5-difluorophenyl)-3-methyl-1H-indazole-1-carboxylate (106 mg) was prepared from 4-bromo-2,6-difluoroaniline (250 mg, 1.2 mmol) and teRT-butyl 3-methyl-5-(4,4,5,5-tetramethyl-1,3,2-dioxaborolan-2-yl)-1H-indazole-1-carboxylate (559 mg, 1.56 mmol) as a white solid. teRT-butyl 5-(4-amino-3,5-difluorophenyl)-3-methyl-1H-indazole-1-carboxylate (205 mg) was dissolved in dichloromethane (4 ml), trifluoroacetic acid (0.8 ml) was added and stirred at RT for 4 h. The solvent was removed and the residue co-evaporated 4 times with dihloromethane. Solid obtained was dried under high vacuum to obtain the title compound (243 mg) as a white solid. $^1$H-NMR (δ ppm, DMSO-d$_6$, 400 MHz): 9.01 (bs, 1H), 7.92 (s, 1H), 7.58 (dd, J 1.4, 8.7, 1H), 7.44 (d, J 8.7, 1H), 7.32 (dd, J 2, 8.2, 2H), 5.22 (s, 2H), 2.50 (s, 3H).

Intermediate 56: 3-chloro-3'-ethyl-5-fluorobiphenyl-4-amine

The title compound (83 mg) was prepared from 4-bromo-2,6-difluoroaniline (100 mg, 0.48 mmol) and 3-ethylphenylboronic acid (86 mg, 0.57 mmol) as a yellow liquid.

Intermediate 57: 3-chloro-3'-ethoxy-2',5-difluorobiphenyl-4-amine

The title compound (65 mg) was prepared from 4-bromo-2-chloro-6-fluoroaniline (120 mg, 0.53 mmol) and 3-ethoxy-2-fluorophenylboronic acid (120 mg, 0.69 mmol) as a colourless liquid.

Intermediate 58: 2-chloro-4-(2,3-dihydrobenzo[b][1,4]dioxin-6-yl)-6-fluoroaniline The title compound (68 mg) was prepared from 4-bromo-2,6-difluoroaniline (100 mg, 0.48 mmol) and 2,3-dihydrobenzo[b][1,4]dioxin-6-ylboronic acid (160 mg, 0.62 mmol) as a white solid.

Intermediate 59: 3-chloro-5-fluoro-3'-(2,2,2-trifluoroethoxy)biphenyl-4-amine

The title compound (85 mg) was prepared from 4-bromo-2-chloro-6-fluoroaniline (100 mg, 0.44 mmol) and 3-(2,2,2-trifluoroethoxy)phenylboronic acid (127 mg, 0.57 mmol) as a white solid. $^1$H-NMR (δ ppm, DMSO-d$_6$, 400 MHz): 7.53-7.44 (m, 2H), 7.38-7.26 (m, 3H), 6.94 (d, J 7, 1H), 5.55 (s, 2H), 4.83 (q, J 8.9, 2H).

Intermediate 60: 3-fluoro-3'-methoxybiphenyl-4-amine

The title compound (430 mg) was prepared from 4-bromo-6-fluoroaniline (500 mg, 2.63 mmol) and 3-Methoxyphenylboronic acid (519 mg, 3.42 mmol) as a red liquid. $^1$H-NMR (δ ppm, DMSO-d$_6$, 400 MHz): 7.34 (dd, J 2, 13.1, 1H), 7.27 (t, J 7.9, 1H), 7.22 (dd, J 2, 8.3, 1H), 7.12 (d, J 7.9, 1H), 7.09-7.07 (m, 1H), 6.84-6.78 (m, 2H), 5.29 (s, 2H), 3.78 (s, 3H).

Intermediate 61: 3'-ethoxybiphenyl-4-amine

The title compound (200 mg) was prepared from 4-bromoaniline (300 mg, 1.74 mmol) and 3-ethoxyphenylboronic acid (380 mg, 2.29 mmol) as a colourless liquid. $^1$H-NMR (δ ppm, DMSO-d$_6$, 400 MHz): 7.33 (d, J 8.5, 2H), 7.26-7.22 (m, 1H), 7.06 (d, J 7.9, 1H), 7.01 (s, 1H), 6.75 (dd, J 5.8, 8.1, 1H), 6.60 (d, J 8.5, 2H), 5.20 (s, 2H), 4.04 (q, J 7, 2H), 1.16 (t, J 7, 3H).

Intermediate 62: 3'-(ethylthio)-3,5-difluorobiphenyl-4-amine

The title compound (900 mg) was prepared from 4-bromo-2,6-difluoroaniline (1 g, 4.8 mmol) and 3-(ethylthio)phenylboronic acid (1.13 g, 6.24 mmol) as a colourless liquid.

Intermediate 63: 3'-cyclopropoxy-3,5-difluorobiphenyl-4-amine

The title compound (170 mg) was prepared from 4-bromo-2,6-difluoroaniline (1.2 g, 5.76 mmol) and 2-(3-cyclopropoxyphenyl)-4,4,5,5-tetramethyl-1,3,2-dioxaborolane (1.5 g, 5.76 mmol) as a yellow liquid.

Intermediate 64: 3-ethyl-5-(4,4,5,5-tetramethyl-1,3,2-dioxaborolan-2-yl)-1H-indole 5-Bromoisatin (5 g, 22.12 mmol) was added drop-wise to ethyl magnesium iodide formed from ethyl iodide (14 ml, 176.96 mmol) and magnesium (8.6 g, 176.96 mmol) in Et$_2$O (50 ml) and stirred at RT overnight. Work-up (EtOAc/H$_2$O) after adding aq. 10% NH$_4$Cl solution and purification gave 5-bromo-3-ethyl-3-hydroxyindolin-2-one (1 g). To a solution of this intermediate (1 g, 3.93 mmol) in THF (40 ml) was added a 2M solution borane-dimethyl sulphide in THF (10 ml, 19.65 mmol) and stirred at RT for 3 h. Work up (EtOAc/H$_2$O) and purification using afforded 5-Bromo-3-ethyl indole (800 mg). To a solution of 5-Bromo-3-ethyl indole (800 mg, 3.57 mmol) in dioxane (10 ml) were added bis(pinacolato)diboron (1.078 g, 4.64 mmol), potassium acetate (1.15 g, 11.78 mmol) and [1,1'-bis(diphenylphosphino)ferrocene]dichloro palladium(II).CH$_2$Cl$_2$, degassed for 30 min. and refluxed overnight. Work-up followed by purification afforded title compound (800 mg) as an off-white solid.

Intermediate 65: 4-(3-ethyl-1H-indol-5-yl)-2,6-difluoroaniline

The title compound (220 mg) was prepared from 4-bromo-2,6-difluoroaniline (662 mg, 2.57 mmol) and intermediate 64 (440 mg, 1.78 mmol) as a yellow liquid. $^1$H-NMR (δ ppm, DMSO-d$_6$, 400 MHz): 10.74 (s, 1H), 7.69 (s, 1H), 7.33-7.29 (m, 2H), 7.23 (dd, J 1.8, 8.3, 2H), 7.09 (s, 1H), 5.12 (s, 2H), 2.73 (q, J 7.5, 2H), 1.27 (q, J 7.5, 3H).

Intermediate 66: 3'-(ethylthio)-2,3,5,6-tetrafluorobiphenyl-4-amine

The title compound (280 mg) was prepared from 4-bromo-2,3,5,6-tetrafluoroaniline (300 mg, 1.22 mmol) and 3-(ethylthio)phenylboronic acid (291 mg, 1.6 mmol) as a colourless liquid.

Intermediate 67: 2'-chloro-2-fluoro-5'-methoxybiphenyl-4-amine

The title compound (280 mg) was prepared from 4-bromo-3-fluoroaniline (227 mg, 1.2 mmol) and 2-chloro-5-methoxyphenylboronic acid (290 mg, 1.6 mmol) as a pale-yellow liquid.

Intermediate 68: 3-fluoro-3'-propoxybiphenyl-4-amine

The title compound (280 mg) was prepared from 4-bromo-2-fluoroaniline (390 mg, 1.6 mmol) and 3-propoxyphenylboronic acid (369 mg, 2 mmol) as a colourless liquid.

Intermediate 69: 3'-propoxybiphenyl-4-amine

The title compound (280 mg) was prepared from 4-bromoaniline (300 mg, 1.7 mmol) and 3-propoxyphenylboronic acid (408 mg, 2.3 mmol) as a colourless liquid.

Intermediate 70: 3'-(ethylthio)-2-fluorobiphenyl-4-amine

The title compound (430 mg) was prepared from 4-bromo-3-fluoroaniline (300 mg, 1.6 mmol) and 3-(ethylthio)phenylboronic acid (370 mg, 2.0 mmol) as a yellow liquid.

Intermediate 71: 3,5-difluoro-3'-(2,2,2-trifluoroethoxy)biphenyl-4-amine

The title compound (89 mg) was prepared from 4-bromo-2,6-difluoroaniline (80 mg, 0.38 mmol) and 3-(2,2,2-trifluoroethoxy)phenylboronic acid (108 mg, 0.5 mmol) as a colourless liquid.

Intermediate 72: 3'-ethyl-3,5-difluorobiphenyl-4-amine

The title compound (89 mg) was prepared from 4-bromo-2,6-difluoroaniline (100 mg, 0.48 mmol) and 3-ethylphenylboronic acid (99 mg, 0.6 mmol) as a colourless liquid.

Intermediate 73: 2'-chlorobiphenyl-4-amine

The title compound (176 mg) was prepared from 4-bromoaniline (300 mg, 1.74 mmol) and 2-chlorophenylboronic acid (354 mg, 2.26 mmol) as a yellow solid.

Intermediate 74: 3'-methoxybiphenyl-4-amine

The title compound (58 mg) was prepared from 4-bromoaniline (300 mg, 1.74 mmol) and 3-methoxyphenylboronic acid (344 mg, 2.26 mmol) as a yellow liquid.

Intermediate 75: 3'-(trifluoromethoxy)biphenyl-4-amine

The title compound (280 mg) was prepared from 4-bromoaniline (300 mg, 1.74 mmol) and 3-(trifluoromethoxy)phenylboronic acid (466 mg, 2.26 mmol) as a pale-yellow liquid.

Intermediate 76: 3'-(ethylthio)-2,6-difluorobiphenyl-4-amine

The title compound (500 mg) was prepared from 4-bromo-3,5-difluoroaniline (300 mg, 1.74 mmol) and 3-(ethylthio)phenylboronic acid (340 mg, 1.86 mmol) as a yellow liquid.

Intermediate 77: 3'-ethylbiphenyl-4-amine

The title compound (300 mg) was prepared from 4-bromoaniline (270 mg, 1.56 mmol) and 3-ethylphenylboronic acid (300 mg, 2.04 mmol) as a colourless liquid.

Intermediate 78: 3'-butoxy-2,3,5,6-tetrafluorobiphenyl-4-amine

The title compound (250 mg) was prepared from 4-bromo-2,3,5,6-tetrafluoroaniline (300 mg, 1.23 mmol) and 3-butoxyphenylboronic acid (310 mg, 1.59 mmol) as a yellow liquid.

Intermediate 79: 3'-butoxy-3-fluorobiphenyl-4-amine

The title compound (170 mg) was prepared from 4-bromo-2-fluoroaniline (240 mg, 1.26 mmol) and 3-butoxyphenylboronic acid (310 mg, 1.59 mmol) as a yellow liquid.

Intermediate 80: 3'-cyclopropoxy-3-fluorobiphenyl-4-amine

The title compound (230 mg) was prepared from 4-bromo-2-fluoroaniline (1 g, 5.26 mmol) and 3-isopropoxyphenylboronic acid (1.8 g, 6.84 mmol) as a yellow liquid.

Intermediate 81: 3'-cyclopropoxybiphenyl-4-amine

The title compound (98 mg) was prepared from 4-bromoaniline (1 g, 5.81 mmol) and 3-isopropoxyphenylboronic acid (1.96 g, 7.55 mmol) as a yellow liquid.

Intermediate 82: 3'-butoxy-3-fluorobiphenyl-4-amine

The title compound (84 mg) was prepared from 4-bromoaniline (200 mg, 1.16 mmol) and 3-butoxyphenylboronic acid (293 mg, 1.5 mmol) as a yellow liquid.

Intermediate 83: 3'-butoxy-2-fluorobiphenyl-4-amine

The title compound (241 mg) was prepared from 4-bromo-3-fluoroaniline (200 mg, 1.05 mmol) and 3-butoxyphenylboronic acid (265 mg, 1.4 mmol) as a colourless liquid.

Intermediate 84: 3'-butoxy-2,6-difluorobiphenyl-4-amine

The title compound (172 mg) was prepared from 4-bromo-3,5-difluoroaniline (200 mg, 1 mmol) and 3-butoxyphenyl boronic acid (242 mg, 1.2 mmol) as a colourless liquid.

Intermediate 85: 3-propyl-5-(4,4,5,5-tetramethyl-1,3,2-dioxaborolan-2-yl)-1H-indole The title compound (500 mg) was prepared as a colourless viscous liquid by using the procedure followed for intermediate 64 from propyl magnesium bromide generated from propyl bromide (16.2 ml, 176.96 mmol) and magnesium (4.3 g, 176.96 mmol) in ether (50 ml), 5-bromoisatin (5 g, 22.12 mmol), THF (20 ml), 2M borane-dimethyl sulphide in THF (10 ml, 19.65 mmol), bis(pinacolato)diboron (600 mg, 2.3 mmol), potassium acetate (600 mg, 2.3 mmol) and [1,1'-bis(diphenylphosphino)ferrocene]dichloro palladium(II) $\cdot CH_2Cl_2$ (44 mg, 0.03 mmol) and dioxane (10 ml).

Intermediate 86: 2,6-difluoro-4-(3-propyl-1H-indol-5-yl)aniline

The title compound (240 mg) was prepared from 4-bromo-2,6-difluoroaniline (400 mg, 1.55 mmol) and intermediate 85 (500 mg, 2.11 mmol) as a colourless gummy liquid.

Intermediate 87: 2-chloro-4-(3-ethyl-1H-indol-5-yl)-6-fluoroaniline

The title compound (60 mg) was prepared from 4-bromo-2-chloro-6-fluoroaniline (300 mg, 1.1 mmol) and intermediate 64 (316 mg, 1.42 mmol) as a brown viscous liquid.

Intermediate 88: 2'-chloro-3-fluoro-5'-methoxybiphenyl-4-amine

The title compound (134 mg) was prepared from 4-bromo-2-fluoroaniline (150 mg, 0.79 mmol) and 2-chloro-5-methoxylphenylboronic acid (191 mg, 1.02 mmol) as a colourless liquid.

Intermediate 89: 2'-chloro-5'-methoxybiphenyl-4-amine

The title compound (154 mg) was prepared from 4-bromoaniline (150 mg, 0.87 mmol) and 2-chloro-5-methoxyphenyl boronic acid (211 mg, 1.13 mmol) as a colourless viscous liquid.

General Procedure for Amide Formation:
Procedure-1

A solution of an anhydride (1.3 eq.) and an amine (1 eq) were dissolved in dioxane and refluxed overnight. Dioxane was evaporated and the resultant residue dissolved in AcOEt and extracted into aq. 2N NaHCO₃ solution. The aqueous layer was acidified with aq. 2N HCl to obtain a solid, which was filtered and dried to give the desired amide.

Examples 1-11, 14, 16-17 and 20 were synthesised using general procedure-1.
Procedure-2

An amine (1 eq) was dissolved in toluene and an anhydride (1 eq) was added in portions and the mixture heated to 60° C. for 4 h. Solidified product was filtered and washed with aq. 2N HCl and dried under vacuum to obtain the desired product.

Examples 12 and 13 were synthesised using general procedure-2.
Procedure-3

An amine (1 eq) was dissolved in acetic acid and an anhydride (2 eq) was added and the mixture stirred at RT overnight. The solid that separated out was filtered and washed with petroleum ether and dried under vacuum to obtain the desired product.

Examples 15, 18, 19, 21-35, 38-71 and 73-100 were prepared using general procedure-3.

Example 1

2-(3,5-Difluoro-3'-methoxybiphenyl-4-ylcarbamoyl) benzoic acid

The title compound (52 mg) was obtained from intermediate 1 (150 mg, 0.64 mmol) and phthalic anhydride (189 mg) as a white solid. M.P.: 168-173° C. $^1$H-NMR (δ ppm, DMSO-$d_6$, 400 MHz): 13.05 (s, 1H), 10.19 (s, 1H), 7.83 (d, J 7.4, 1H), 7.69-7.63 (m, 1H), 7.62-7.52 (m, 4H), 7.39 (t, J 7.9, 1H), 7.34-7.27 (m, 2H), 6.98 (d, J 6.8, 1H), 3.83 (s, 3H). MS (m/z): 381.55 ([M–H]⁻).

Example 2

2-(3,5-Difluoro-3'-methoxybiphenyl-4-ylcarbamoyl) benzenesulfonic acid

The title compound (64 mg) was obtained from intermediate 1 (150 mg, 0.64 mmol) and 2-sulphobenzoic acid cyclic anhydride (235 mg) as a brown solid. M.P.: 97-102° C. $^1$H-NMR (δ ppm, DMSO-$d_6$, 400 MHz): 11.48 (s, 1H), 7.92 (d, J 7.1, 1H), 7.80 (d, J 7, 1H), 7.57-7.49 (m, 4H), 7.38 (t, J 7.8, 1H), 7.34-7.28 (m, 2H), 6.97 (d, J 8.1, 1H), 3.83 (s, 3H). MS (m/z): 417.6 ([M–H]⁻).

Example 3

2-(6-(3-Methoxyphenyl)pyridin-3-ylcarbamoyl)benzoic acid

The title compound (48 mg) was obtained from intermediate 3 (100 mg, 0.5 mmol) and phthalic anhydride (147 mg, 1 mmol) as a white solid. M.P.: 194-199° C. $^1$H-NMR (δ ppm, DMSO-$d_6$, 400 MHz): 13.17 (bs, 1H), 10.64 (s, 1H), 8.88 (d, J 2, 1H), 8.22 (dd, J 2.2, 8.7, 1H), 7.97 (d, J 8.7, 1H), 7.90 (d, J 7, 1H), 7.70-7.66 (m, 1H), 7.63-7.56 (m, 4H), 7.38 (t, J 8, 1H), 6.98-6.95 (m, 1H), 3.82 (s, 3H). MS (m/z): 347.30 ([M–H]⁻).

Example 4

2-(3'-Ethoxy-3-fluorobiphenyl-4-ylcarbamoyl)benzoic acid

The title compound (26 mg) was obtained from intermediate 4 (100 mg, 0.5 mmol) and phthalic anhydride (128 mg, 1 mmol) as a white solid. M.P.: 151-157° C. $^1$H-NMR (δ ppm, DMSO-$d_6$, 400 MHz): 13.06 (s, 1H), 10.22 (s, 1H), 7.95 (t, J 8.5, 1H), 7.89 (d, J 7.7, 1H), 7.68-7.52 (m, 5H), 7.35 (t, J 7.9, 1H), 7.25 (d, J 8.2, 1H), 7.21 (s, 1H), 6.92 (d, J 8.4, 1H), 4.10 (q, J 7, 2H), 1.34 (t, J 7, 3H). MS (m/z): 379.24 ([M]⁻).

Example 5

2-(3'-Ethoxy-3,5-difluorobiphenyl-4-ylcarbamoyl) benzoic acid

The title compound (15 mg) was obtained from intermediate 5 (100 mg, 0.43 mmol) and pthalic anhydride (118 mg, 0.86 mmol) as a white solid. M.P.: 136-141° C. $^1$H-NMR (δ ppm, DMSO-d$_6$, 400 MHz): 13.04 (s, 1H), 10.19 (s, 1H), 7.83 (d, J 7.4, 1H), 7.69-7.64 (m, 1H), 7.62-7.51 (m, 4H), 7.37 (t, J 7.9, 1H), 7.32-7.25 (m, 2H), 6.96 (dd, J 1.7, 8.3, 1H), 4.11 (q, J 7, 2H), 1.34 (t, J 7, 3H). MS (m/z): 395.81 ([M−H]$^-$).

Example 6

3-(3,5-Difluoro-3'-methoxybiphenyl-4-ylcarbamoyl) pyrazine-2-carboxylic acid

The title compound (270 mg) was obtained from intermediate 1 (150 mg, 0.64 mmol) and 2,3-pyrazinedicarboxylic anhydride (190 mg, 1.26 mmol) as a white solid. M.P.: 180.1-183.4° C. $^1$H-NMR (δ ppm, DMSO-d$_6$, 400 MHz): 13.82 (bs, 1H), 10.7 (s, 1H), 8.92 (d, J 5.7, 2H), 7.59 (d, J 9.1, 2H), 7.42-7.38 (m, 1H), 7.36-7.28 (m, 2H), 7.00 (d, J 8, 1H), 3.83 (s, 3H). MS (m/z): 384.05 ([M−H]$^-$).

Example 7

3-(3,5-Difluoro-3'-ethoxybiphenyl-4-ylcarbamoyl) pyrazine-2-carboxylic acid

The title compound (84 mg) was obtained from intermediate 5 (100 mg, 0.4 mmol) and 2,3-pyrazinedicarboxylic anhydride (120 mg, 0.8 mmol) as a white solid. M.P.: 133.4-137.3° C. $^1$H-NMR (δ ppm, DMSO-d$_6$, 400 MHz): 13.76 (s, 1H), 10.68 (s, 1H), 8.92 (dd, J 2.3, 7.7, 2H), 7.58 (d, J 9.2, 2H), 7.41-7.36 (m, 1H), 7.34-7.26 (m, 2H), 6.98 (d, J 8, 1H), 4.11 (q, J 6.9, 2H), 1.35 (t, J 6.9, 3H). MS (m/z): 398.19 ([M−H]$^-$).

Example 8

2-(2'-Chloro-3,5-difluorobiphenyl-4-ylcarbamoyl) benzoic acid

The title compound (110 mg) was obtained from intermediate 6 (140 mg, 0.59 mmol) and phthalic anhydride (170 mg, 1.17 mmol) as a white solid. M.P.: 143.5-145.1° C. $^1$H-NMR (δ ppm, DMSO-d$_6$, 400 MHz): 13.06 (s, 1H), 10.2 (s, 1H), 7.85 (d, J 7.6, 1H), 7.67 (t, J 7.3, 1H), 7.63-7.56 (m, 3H), 7.52-7.43 (m, 3H), 7.28 (d, J 8.4, 2H). MS (m/z): 386.15 ([M−H]$^-$).

Example 9

3-[3'-(Benzyloxy)-3,5-difluorobiphenyl-4-ylcarbamoyl]pyrazine-2-carboxylic acid

The title compound (42 mg) was obtained from intermediate 9 (65 mg, 0.21 mmol) and 2,3-Pyrazinedicarboxylic anhydride (62 mg, 0.42 mmol) as a white solid. M.P.: 142-144.5° C. $^1$H-NMR (δ ppm, DMSO-d$_6$, 400 MHz): 13.77 (bs, 1H), 10.69 (s, 1H), 8.92 (dd, J 2.4, 7.7, 2H), 7.60 (d, J 9.2, 2H), 7.48 (d, J 7.3, 2H), 7.44-7.32 (m, 6H), 7.07 (d, J 6.5, 1H), 5.20 (s, 2H). MS (m/z): 460.28 ([M−H]$^-$).

Example 10

2-(3,5-Difluorobiphenyl-4-ylcarbamoyl)benzoic acid

The title compound (85 mg) was obtained from intermediate 7 (100 mg, 0.48 mmol) and phthalic anhydride (144 mg, 0.86 mmol) as a white solid. M.P.: 161.2-165.7° C. $^1$H-NMR (δ ppm, DMSO-d$_6$, 400 MHz): 13.04 (s, 1H), 10.19 (s, 1H), 7.83 (d, J 7.6, 1H), 7.76 (d, J 7.4, 2H), 7.65 (d, J 8.2, 1H), 7.62-7.48 (m, 6H), 7.43 (d, J 7.2, 1H). MS (m/z): 352.06 ([M−H]$^-$).

Example 11

3-(3-Chloro-3'-ethoxy-5-fluorobiphenyl-4-ylcarbamoyl)pyrazine-2-carboxylic acid

The title compound (30 mg) was obtained from intermediate 10 (100 mg, 0.38 mmol) and 2,3-pyrazinedicarboxylic anhydride (112 mg, 0.75 mmol) as a white solid. M.P.: 148-153° C. $^1$H-NMR (δ ppm, DMSO-d$_6$, 400 MHz): 13.74 (bs, 1H), 10.72 (s, 1H), 8.93 (dd, J 2.3, 6.4, 2H), 7.76 (s, 1H), 7.70 (d, J 10.7, 1H), 7.42-7.36 (m, 1H), 7.34-7.26 (m, 2H), 6.98 (dd, J 1.8, 8.1, 1H), 4.12 (q, J 6.9, 2H), 1.34 (t, J 6.9, 3H). MS (m/z): 414.01 ([M−H]$^-$).

Example 12

2-[3,5-Difluoro-3'-(trifluoromethoxy)biphenyl-4-ylcarbamoyl]benzoic acid

The title compound (15 mg) was obtained from intermediate 8 (100 mg, 0.34 mmol) and phthalic anhydride (50 mg, 0.34 mmol) as a white solid. M.P.: 148.2-151.4° C. $^1$H-NMR (δ ppm, DMSO-d$_6$, 400 MHz): 13.07 (s, 1H), 10.24 (s, 1H), 7.83 (t, J 6.2, 2H), 7.79 (s, 1H), 7.54-7.50 (m, 6H), 7.42 (d, J 8.8, 1H). MS (m/z): 436.13 ([M−H]$^-$).

Example 13

2-[3'-(Benzyloxy)-3,5-difluorobiphenyl-4-ylcarbamoyl]benzoic acid

The title compound (12 mg) was obtained from intermediate 9 (100 mg, 0.32 mmol) and phthalic anhydride (47 mg, 0.32 mmol) as a white solid. M.P.: 140.3-143.4° C. $^1$H-NMR (δ ppm, DMSO-d$_6$, 400 MHz): 13.04 (s, 1H), 10.19 (s, 1H), 7.83 (d, J 7.6, 1H), 7.68-7.64 (m, 1H), 7.62-7.53 (m, 4H), 7.48 (d, J 7.2, 2H), 7.42-7.37 (m, 4H), 7.36-7.32 (m, 2H), 7.05 (dd, J 2, 7.7, 1H), 5.20 (s, 2H). MS (m/z): 457.83 ([M−H]$^-$).

Example 14

4,5-Dichloro-2-(3-chloro-3'-ethoxy-5-fluorobiphenyl-4-ylcarbamoyl)benzoic acid

The title compound (42 mg) was obtained from intermediate 10 (100 mg, 0.38 mmol) and phthalic anhydride (160 mg, 0.75 mmol) as an off-white solid. M.P.: 260-265° C. $^1$H-NMR (δ ppm, DMSO-d$_6$, 400 MHz): 15.33 (s, 1H), 8.16 (s, 1H), 7.96 (s, 1H), 7.71 (s, 1H), 7.64 (d, J 11, 1H), 7.36 (t, J 7.8, 1H), 7.27-7.22 (m, 2H), 6.95 (dd, J 1.8, 8.1, 1H), 4.12 (d, J 7, 2H), 1.34 (t, J 7, 3H). MS (m/z): 481.02 ([M−H]$^-$).

Example 15

2-(3-Chloro-3'-ethoxy-5-fluorobiphenyl-4-ylcarbamoyl)benzoic acid

The title compound (86 mg) was obtained from intermediate 10 (145 mg, 0.55 mmol) and phthalic anhydride (160 mg, 1.1 mmol) as a white solid. M.P.: 135-140° C. $^1$H-NMR (δ ppm, DMSO-d$_6$, 400 MHz): 13.02 (s, 1H), 10.23 (s, 1H), 7.82 (d, J 7.6, 1H), 7.72 (s, 1H), 7.70-7.58 (m, 4H), 7.38 (t, J 7.8, 1H), 7.33-7.26 (m, 2H), 6.97 (dd, J 2, 8.1, 1H), 4.12 (q, J 6.9, 2H), 1.35 (t, J 6.9, 3H). MS (m/z): 412.05 ([M−H]$^−$).

Example 16

4,5-Dichloro-2-(3,5-difluoro-3'-methoxybiphenyl-4-ylcarbamoyl)benzoic acid

The title compound (95 mg) was obtained from intermediate 1 (100 mg, 0.42 mmol) and 5,6-dichloroisobenzofuran-1,3-dione (182 mg, 0.84 mmol) as a white solid. M.P.: 158.6-162.2° C. $^1$H-NMR (δ ppm, DMSO-d$_6$, 400 MHz): 13.58 (s, 1H), 10.40 (s, 1H), 7.57 (d, J 9.1, 2H), 8.03 (s, 1H), 7.83 (s, 1H), 7.39 (t, J 7.9, 1H), 7.34-7.28 (m, 2H), 6.98 (dd, J 1.9, 6.9, 1H), 3.83 (s, 3H). MS (m/z): 451.24 ([M−H]$^−$).

Example 17

4,5-Dichloro-2-(3'-ethoxy-3,5-difluorobiphenyl-4-ylcarbamoyl)benzoic acid

The title compound (87 mg) was obtained from intermediate 5 (100 mg, 0.42 mmol) and 5,6-dichloroisobenzofuran-1,3-dione (173 mg, 0.8 mmol) as a white solid. M.P.: 190.1-192.4° C. $^1$H-NMR (δ ppm, DMSO-d$_6$, 400 MHz): 13.58 (s, 1H), 10.39 (s, 1H), 8.03 (s, 1H), 7.82 (s, 1H), 7.56 (d, J 9.2, 2H), 7.37 (t, J 7.9, 1H), 7.33-7.26 (m, 2H), 6.97 (dd, J 1.8, 8.1, 1H), 4.11 (q, J 7, 2H), 1.34 (t, J 7, 3H). MS (m/z): 464.92 ([M−H]$^−$).

Example 18

2-(3,5-Dichloro-3'-methoxybiphenyl-4-ylcarbamoyl)benzoic acid

The title compound (20 mg) was obtained from intermediate 11 (150 mg, 0.56 mmol) and phthalic anhydride (165 mg, 1.12 mmol) as a white solid. M.P.: 163-168° C. $^1$H-NMR (δ ppm, DMSO-d$_6$, 400 MHz): 13.0 (s, 1H), 10.37 (s, 1H), 7.86 (s, 2H), 7.80 (d, J 7.5, 1H), 7.74-7.65 (m, 2H), 7.60 (t, J 7.5, 1H), 7.40 (t, J 7.9, 1H), 7.34-7.27 (m, 2H), 6.99 (d, J 7.5, 1H), 3.84 (s, 3H). MS (m/z): 415.15 ([M−H]$^−$).

Example 19

2-(3-Chloro-5-fluoro-3'-propoxybiphenyl-4-ylcarbamoyl)benzoic acid

The title compound (38 mg) was obtained from intermediate 12 (100 mg, 0.36 mmol) and phthalic anhydride (105 mg, 0.72 mmol) as a white solid. M.P.: 144-148° C. $^1$H-NMR (δ ppm, DMSO-d$_6$, 400 MHz): 13.03 (s, 1H), 10.24 (s, 1H), 7.82 (d, J 7.5, 1H), 7.73 (s, 1H), 7.70-7.57 (m, 4H), 7.38 (t, J 7.7, 1H), 7.32-7.26 (m, 2H), 6.98 (d, J 8.1, 1H), 4.02 (t, J 6.5, 2H), 1.77-1.72 (m, 2H), 0.99 (t, J 7.4, 3H). MS (m/z): 426.05 ([M−H]$^−$).

Example 20

2-(3-Chloro-2',5-difluorobiphenyl-4-ylcarbamoyl)benzoic acid

The title compound (15 mg) was obtained from intermediate 13 (100 mg, 0.34 mmol) and phthalic anhydride (100 mg, 0.68 mmol) as a white solid. M.P.: 163-167° C. $^1$H-NMR (δ ppm, DMSO-d$_6$, 400 MHz): 13.05 (s, 1H), 10.3 (s, 1H), 7.83 (d, J 7.6, 1H), 7.70-7.58 (m, 5H), 7.57-7.46 (m, 2H), 7.40-7.31 (m, 2H). MS (m/z): 386.15 ([M−H]$^−$).

Example 21

2-(3,5-Dichloro-3'-ethoxybiphenyl-4-ylcarbamoyl)benzoic acid

The title compound (30 mg) was obtained from intermediate 14 (150 mg, 0.53 mmol) and phthalic anhydride (157 mg, 1.06 mmol) as a white solid. M.P.: 135.9-138.2° C. $^1$H-NMR (δ ppm, DMSO-d$_6$, 400 MHz): 13.0 (s, 1H), 10.37 (s, 1H), 7.86 (s, 2H), 7.80 (d, J 7.3, 1H), 7.74-7.64 (m, 2H), 7.62-7.55 (m, 1H), 7.38 (t, J 7.9, 1H), 7.32-7.26 (m, 2H), 7.00-6.96 (m, 1H), 4.12 (q, J 7, 2H), 1.34 (t, J 7, 3H). MS (m/z): 429.30 ([M−H]$^−$).

Example 22

2-[3-Fluoro-3'-(trifluoromethoxy)biphenyl-4-ylcarbamoyl]benzoic acid

The title compound (124 mg) was obtained from intermediate 15 (100 mg, 0.44 mmol) and phthalic anhydride (130 mg, 0.9 mmol) as a white solid. M.P.: 128.3-132.1° C. $^1$H-NMR (δ ppm, DMSO-d$_6$, 400 MHz): 13.07 (s, 1H), 10.28 (s, 1H), 7.99 (t, J 8.3, 1H), 7.88 (d, J 7.4, 1H), 7.77 (d, J 8, 1H), 7.67 (s, 1H), 7.69-7.52 (m, 6H), 7.37 (d, J 8.2, 1H). MS (m/z): 417.86 ([M−H]$^−$).

Example 23

2-[2'-Fluoro-3-(trifluoromethoxy)biphenyl-4-ylcarbamoyl]benzoic acid

The title compound (82 mg) was obtained from intermediate 16 (100 mg, 0.36 mmol) and phthalic anhydride (109 mg, 0.72 mmol) as a white solid. M.P.: 142.2-148.1° C. $^1$H-NMR (δ ppm, DMSO-d$_6$, 400 MHz): 13.08 (s, 1H), 10.36 (s, 1H), 8.03 (d, J 8.2, 1H), 7.90 (d, J 7.8, 1H), 7.68 (t, J 7.5, 1H), 7.65-7.54 (m, 4H), 7.49-7.41 (m, 2H), 7.38-7.30 (m, 2H). MS (m/z): 418.00 ([M−H]$^−$).

Example 24

2-(3,5-Dichloro-2'-fluorobiphenyl-4-ylcarbamoyl)benzoic acid

The title compound (78 mg) was obtained from intermediate 17 (100 mg, 0.39 mmol) and phthalic anhydride (115 mg, 0.78 mmol) as a white solid. M.P.: 185.4-193.6° C. $^1$H-NMR (δ ppm, DMSO-d$_6$, 400 MHz): 13.02 (s, 1H), 10.42 (s, 1H), 7.81 (d, J 7.4, 1H), 7.74 (s, 2H), 7.72-7.58 (m, 4H), 7.53-7.47 (m, 1H), 7.40-7.31 (m, 2H). MS (m/z): 402.11 ([M−H]$^−$).

Example 25

2-(3,5-Difluoro-3'-isopropoxybiphenyl-4-ylcarbamoyl)benzoic acid

The title compound (64 mg) was obtained from intermediate 18 (100 mg, 0.38 mmol) and phthalic anhydride (112 mg, 0.76 mmol) as a white solid. M.P.: 122-125° C. $^1$H-NMR (δ ppm, DMSO-d$_6$, 400 MHz): 13.05 (s, 1H), 10.20 (s, 1H), 7.83 (d, J 7.5, 1H), 7.66 (t, J 7.3, 1H), 7.60-7.52 (m, 4H), 7.37 (t, J 7.8, 1H), 7.30-7.24 (m, 2H), 6.96 (dd, J 2.1, 8.2, 1H), 4.76 (septet, J 6.0, 1H), 1.28 (d, J 6, 6H). MS (m/z): 410.02 ([M–H]⁻).

Example 26

2-(3,5-Difluoro-3'-propoxybiphenyl-4-ylcarbamoyl)benzoic acid

The title compound (68 mg) was obtained from intermediate 19 (100 mg, 0.38 mmol) and phthalic anhydride (112 mg, 0.76 mmol) as a white solid. M.P.: 128.6-132.1° C. $^1$H-NMR (δ ppm, DMSO-$d_6$, 400 MHz): 13.05 (s, 1H), 10.19 (s, 1H), 7.83 (d, J 7.7, 1H), 7.66 (t, J 7.4, 1H), 7.62-7.52 (m, 4H), 7.37 (t, J 7.8, 1H), 7.32-7.26 (m, 2H), 6.97 (dd, J 2, 8.1, 1H), 4.01 (t, J 6.5, 2H), 1.77-1.67 (m, 2H), 0.99 (t, J 7.4, 3H). MS (m/z): 410.16 ([M–H]⁻).

Example 27

4,5-Dichloro-2-(2',3-dichloro-5-fluorobiphenyl-4-ylcarbamoyl)benzoic acid

The title compound (110 mg) was obtained from intermediate 20 (100 mg, 0.39 mmol) and 5,6-dichloroisobenzofuran-1,3-dione (169 mg, 0.78 mmol) as a white solid. M.P.: 202.3-206.5° C. $^1$H-NMR (δ ppm, DMSO-$d_6$, 400 MHz): 13.60 (s, 1H), 10.50 (s, 1H), 8.04 (s, 1H), 7.82 (s, 1H), 7.63-7.58 (m, 1H), 7.52-7.43 (m, 5H). MS (m/z): 471.69 ([M–H]⁻).

Example 28

3,6-dichloro-2-(3'-ethoxy-3,5-difluorobiphenyl-4-ylcarbamoyl)benzoic acid

The title compound (51 mg) was obtained from intermediate 5 (100 mg, 0.4 mmol) and 4,7-dichloroisobenzofuran-1,3-dione (173 mg, 0.8 mmol) as a white solid. M.P.: 126.9-131.4° C. $^1$H-NMR (δ ppm, DMSO-$d_6$, 400 MHz): 13.96 (s, 1H), 10.56 (s, 1H), 7.68 (s, 2H), 7.55 (d, J 9.1, 2H), 7.38 (t, J 7.9, 1H), 7.32-7.26 (m, 2H), 6.97 (dd, J 1.7, 12.2, 1H), 4.12 (q, J 7, 2H), 1.34 (t, J 7, 3H).

Example 29

2-(3'-butoxy-3-chloro-5-fluorobiphenyl-4-ylcarbamoyl)benzoic acid

The title compound (39 mg) was obtained from intermediate 21 (90 mg, 0.31 mmol) and phthalic anhydride (90 mg, 0.6 mmol) as a white solid. M.P.: 128-130° C. $^1$H-NMR (δ ppm, DMSO-$d_6$, 400 MHz): 13.02 (s, 1H), 10.23 (s, 1H), 7.82 (d, J 7.9, 1H), 7.73 (s, 1H), 7.60-7.57 (m, 4H), 7.37 (t, J 7.9, 1H), 7.32-7.25 (m, 2H), 6.99-6.96 (m, 1H), 4.06 (t, J 6.4, 2H), 1.73-1.68 (m, 2H), 1.45 (h, J 7.5, 2H), 0.94 (t, J 7.4, 3H). MS (m/z): 440.19 ([M–H]⁻).

Example 30

4,5-Dichloro-2-(2'-chloro-3,5-difluorobiphenyl-4-ylcarbamoyl)benzoic acid

The title compound (150 mg) was obtained from intermediate 6 (100 mg, 4.18 mmol) and 5,6-dichloroisobenzofuran-1,3-dione (181 mg, 8.4 mmol) as a white solid. M.P.: 202-205.5° C. $^1$H-NMR (δ ppm, DMSO-$d_6$, 400 MHz): 13.61 (s, 1H), 10.45 (s, 1H), 8.04 (s, 1H), 7.83 (s, 1H), 7.62-7.58 (m, 1H), 7.52-7.49 (m, 1H), 7.48-7.43 (m, 2H), 7.30 (d, J 8.5, 2H). MS (m/z): 455.94 ([M–H]⁻).

Example 31

2-(3-Chloro-5-fluoro-3'-isobutoxybiphenyl-4-ylcarbamoyl)benzoic acid

The title compound (150 mg) was obtained from intermediate 22 (100 mg, 4.18 mmol) and 5,6-dichloroisobenzofuran-1,3-dione (181 mg, 8.4 mmol) as a white solid. M.P.: 202-205.5° C. $^1$H-NMR (δ ppm, DMSO-$d_6$, 400 MHz): 13.03 (s, 1H), 10.23 (s, 1H), 7.82 (d, J 7.4, 1H), 7.73 (s, 1H), 7.70-7.57 (m, 4H), 7.38 (t, J 7.8, 1H), 7.32-7.26 (m, 2H), 6.99 (dd, J 1.7, 8.2, 1H), 3.83 (d, J 6.5, 2H), 2.10-1.99 (m, 1H), 1.00 (d, J 6.7, 6H). MS (m/z): 439.84 ([M–H]⁻).

Example 32

2-(2',3,5-Trifluorobiphenyl-4-ylcarbamoyl)benzoic acid

The title compound (72 mg) was obtained from intermediate 23 (100 mg, 0.44 mmol) and phthalic anhydride (130 mg, 0.88 mmol) as a white solid. M.P.: 152.2-156.3° C. $^1$H-NMR (δ ppm, DMSO-$d_6$, 400 MHz): 13.06 (s, 1H), 10.25 (s, 1H), 7.84 (d, J 7.6, 1H), 7.70-7.56 (m, 4H), 7.52-7.45 (m, 1H), 7.43-7.38 (m, 2H), 7.36-7.31 (m, 2H). MS (m/z): 369.91 ([M–H]⁻).

Example 33

2-(2',3,5-Trichlorobiphenyl-4-ylcarbamoyl)benzoic acid

The title compound (20 mg) was obtained from intermediate 24 (100 mg, 0.37 mmol) and phthalic anhydride (130 mg, 0.88 mmol) as a white solid. M.P.: 182-185° C. $^1$H-NMR (δ ppm, DMSO-$d_6$, 400 MHz): 13.01 (s, 1H), 10.40 (s, 1H), 7.82 (d, J 7.2, 1H), 7.72-7.67 (m, 2H), 7.64-7.59 (m, 4H), 7.53-7.50 (m, 1H), 7.49-7.45 (m, 2H). MS (m/z): 419.61 ([M–H]⁻).

Example 34

2-(3,5-Difluoro-3'-isobutoxybiphenyl-4-ylcarbamoyl)benzoic acid

The title compound (34 mg) was obtained from intermediate 25 (100 mg, 0.36 mmol) and phthalic anhydride (106 mg, 0.72 mmol) as a white solid. M.P.: 112.6-116.4° C. $^1$H-NMR (δ ppm, DMSO-$d_6$, 400 MHz): 13.04 (s, 1H), 10.18 (s, 1H), 7.83 (d, J 7.5, 1H), 7.68-7.64 (m, 1H), 7.62-7.52 (m, 4H), 7.37 (t, J 7.8, 1H), 7.33-7.25 (m, 2H), 6.98 (d, J 8.2, 1H), 3.84 (d, J 6.5, 2H), 2.10-1.99 (m, 1H), 1.00 (d, J 6.7, 6H). MS (m/z): 423.95 ([M–H]⁻).

Example 35

2-(3'-Butoxy-3,5-difluorobiphenyl-4-ylcarbamoyl)benzoic acid

The title compound (32 mg) was obtained from intermediate 26 (100 mg, 0.36 mmol) and phthalic anhydride (106 mg, 0.72 mmol) as a white solid. M.P.: 119.3-123.3° C.

¹H-NMR (δ ppm, DMSO-d₆, 400 MHz): 13.04 (s, 1H), 10.19 (s, 1H), 7.83 (d, J 7.4, 1H), 7.69-7.63 (m, 1H), 7.62-7.52 (m, 4H), 7.37 (t, J 7.9, 1H), 7.32-7.26 (m, 2H), 6.97 (dd, J 1.6, 8, 1H), 4.05 (t, J 6.4, 2H), 1.72 (q, J 6.4, 2H), 1.47 (h, J 7.5, 2H), 0.94 (t, J 7.3, 3H). MS (m/z): 423.88 ([M−H]⁻).

Example 36

N-(3-Chloro-3'-ethoxy-5-fluorobiphenyl-4-yl)-2-(hydroxymethyl)benzamide

Oxalyl chloride (0.86 ml, 9.8 mml) and two drops of DMF were added to a solution of 2-(methoxycarbonyl)benzoic acid (590 mg, 3.27 mmol) in dichloromethane (10 ml) and cooled to 0° C. and stirred at RT for 30 min. After 30 min., the solvent was removed to obtain methyl 2-(chloroformyl)benzoate (quantitative). A solution of this intermediate (401 mg, 2.03 mmol) in dichloromethane was added to a solution of intermediate 10 (540 mg, 2.03 mmol) and pyridine (0.19 ml, 2.43 mmol) in dichloromethane (5 ml) at 0° C. and stirred at RT for 30 min. Work-up (CH₂Cl₂/H₂O) and purification gave methyl 2-(3-chloro-3'-ethoxy-5-fluorobiphenyl-4-ylcarbamoyl)benzoate (250 mg) as an off-white solid. Lithium borohydride (20 mg, 0.94 mmol) was added to a solution of this product (200 mg, 0.47 mmol) in THF (5 ml) at 0° C. and the mixture stirred at RT for 2 hrs. Work-up (EtOAc/aq. 10% NH₄Cl then H₂O) and purification afforded the title compound (30 mg) as a white solid. M.P.: 139.2-141.5° C. ¹H-NMR (δ ppm, DMSO-d₆, 400 MHz): 10.22 (s, 1H), 7.76 (s, 1H), 7.73-7.60 (m, 3H), 7.54 (t, J 6.7, 1H), 7.43-7.36 (m, 2H), 7.33-7.26 (m, 2H), 6.97 (dd, J 1.8, 8.1, 1H), 5.32 (t, J 5.6, 1H), 4.72 (d, J 5.6, 2H), 4.12 (q, J 7, 2H), 1.35 (t, J 7, 3H).

Example 37

N-(3'-Ethoxy-3,5-difluorobiphenyl-4-yl)-2-(hydroxymethyl)benzamide

A solution of methyl 2-(chloroformyl)benzoate (prepared as described under example 37, 361 mg, 2.0 mmol) in dichloromethane was added slowly to a solution of intermediate 5 (500 mg, 2.0 mmol) and pyridine (0.19 ml, 2.43 mmol) in dichloromethane (5 ml) and stirred at 0° C. and stirred at RT for 30 min. Work-up (CH₂Cl₂/H₂O) and purification gave methyl 2-(3'-ethoxy-3,5-difluorobiphenyl-4-ylcarbamoyl)benzoate (212 mg) as a pale-yellow solid. Lithium borohydride (21 mg, 0.96 mmol) was added to a solution of this intermediate (200 mg, 0.48 mmol) in THF (3 ml) at 0° C. and the mixture stirred at RT for 2 hrs. work-up (EtOAc/aq. 10% NH₄Cl then H₂O) and purification gave the title compound (21 mg) as a white solid. M.P.: 94.8-99.1° C. ¹H-NMR (δ ppm, DMSO-d₆, 400 MHz): 10.16 (s, 1H), 7.64 (d, J 7.8, 1H), 7.61-7.51 (m, 4H), 7.42-7.35 (m, 2H), 7.32-7.26 (m, 2H), 6.97 (dd, J 2, 7.6, 1H), 5.31 (t, J 5.6, 1H), 4.70 (d, J 5.6, 2H), 4.11 (q, J 7, 2H), 1.35 (t, J 7, 3H).

Example 38

2-(3-Chloro-3'-ethoxy-5-fluorobiphenyl-4-ylcarbamoyl)-6-fluorobenzoic acid

The title compound (20 mg) was obtained from intermediate 10 (100 mg, 0.38 mmol) and 4-fluoroisobenzofuran-1,3-dione (125 mg, 0.75 mmol) as a white solid. M.P.: 156.3-158.2° C. ¹H-NMR (δ ppm, DMSO-d₆, 400 MHz): 13.42 (s, 1H), 10.44 (s, 1H), 7.79-7.69 (m, 2H), 7.59-7.50 (m, 3H), 7.42-7.34 (m, 1H), 7.32-7.24 (m, 2H), 6.97 (d, J 7.6, 1H), 4.12 (t, J 7, 2H), 1.33 (q, J 7, 3H).

Example 39

2-[3-Chloro-5-fluoro-3'-(trifluoromethoxy)biphenyl-4-ylcarbamoyl]benzoic acid The title compound (38 mg) was obtained from intermediate 27 (150 mg, 0.6 mmol) and phthalic anhydride (176 mg, 1.2 mmol) as a white solid. M.P.: 153-156.5° C. ¹H-NMR (δ ppm, DMSO-d6, 400 MHz): 13.04 (s, 1H), 10.28 (s, 1H), 7.87-7.73 (m, 5H), 7.69-7.55 (m, 4H), 7.43 (d, J 7.6, 1H). MS (m/z): 451.95 ([M−H]⁻).

Example 40

2-[4-(Benzyloxy)-2,6-difluorophenylcarbamoyl]benzoic acid

The title compound (134 mg) was obtained from intermediate 29 (160 mg, 0.65 mmol) and phthalic anhydride (193 mg, 1.3 mmol) as a white solid. M.P.: 176.2-180.6° C. ¹H-NMR (δ ppm, DMSO-d6, 400 MHz): 12.98 (bs, 1H), 9.88 (s, 1H), 7.79 (d, J 7.6, 1H), 7.67-7.61 (m, 1H), 7.60-7.52 (m, 2H), 7.45 (d, J 7, 2H), 7.40 (t, J 7, 2H), 7.37-7.32 (m, 1H), 6.90 (d, J 9.4, 2H), 5.14 (s, 2H).

Example 41

2-[3'-(Cyclopentyloxy)-3,5-difluorobiphenyl-4-ylcarbamoyl]benzoic acid

The title compound (38 mg) was obtained from intermediate 32 (150 mg, 0.6 mmol) and phthalic anhydride (176 mg, 1.2 mmol) as a white solid. M.P.: 153-156.5° C. ¹H-NMR (δ ppm, DMSO-d6, 400 MHz): 13.05 (s, 1H), 10.18 (s, 1H), 7.83 (d, J 7.6, 1H), 7.69-7.64 (m, 1H), 7.62-7.49 (m, 4H), 7.36 (t, J 8, 1H), 7.30-7.25 (m, 1H), 7.23 (m, 1H), 6.95 (dd, J 2, 8.1, 1H), 5.00-4.92 (m, 1H), 2.00-1.90 (m, 2H), 1.76-1.68 (m, 4H), 1.64-1.54 (m, 2H). MS (m/z): 436.13 ([M−H]⁻).

Example 42

2-(3-Chloro-3'-(cyclopentyloxy)-5-fluorobiphenyl-4-ylcarbamoyl)benzoic acid The title compound (38 mg) was obtained from intermediate 33 (100 mg, 0.33 mmol) and phthalic anhydride (96 mg, 0.65 mmol) as a white solid. M.P.: 122-126° C. ¹H-NMR (δ ppm, DMSO-d₆, 400 MHz): 13.02 (s, 1H), 10.23 (s, 1H), 7.82 (d, J 7.4, 1H), 7.71 (s, 1H), 7.68-7.58 (m, 4H), 7.37 (t, J 7.6, 1H), 7.30-7.21 (m, 2H), 6.95 (dd, J 2.2, 8.1, 1H), 5.00-4.93 (s, 1H), 2.00-1.88 (m, 2H), 1.80-1.68 (m, 4H), 1.63-1.54 (m, 2H). MS (m/z): 452.16 ([M−H]⁻).

Example 43

2-[3'-(Difluoromethoxy)-3,5-difluorobiphenyl-4-ylcarbamoyl]benzoic acid

The title compound (36 mg) was obtained from intermediate 34 (40 mg, 0.15 mmol) and phthalic anhydride (43 mg, 0.29 mmol) as a white solid. M.P.: 148.2-150.5° C. ¹H-NMR (δ ppm, DMSO-d$_6$, 400 MHz): 13.05 (s, 1H), 10.22 (s, 1H), 7.84 (d, J 7.7, 1H), 7.69-7.51 (m, 8H), 7.36 (t, J 74, 1H), 7.22 (dd, J 1.8, 9.7, 1H).

Example 44

2-[3-Chloro-3'-(difluoromethoxy)-5-fluorobiphenyl-4-ylcarbamoyl]benzoic acid

The title compound (41 mg) was obtained from intermediate 35 (40 mg, 0.14 mmol) and phthalic anhydride (41 mg, 0.28 mmol) as a white solid. M.P.: 156.5-159.5° C. $^1$H-NMR (δ ppm, DMSO-d$_6$, 400 MHz): 13.03 (s, 1H), 10.26 (s, 1H), 7.83 (d, J 7.6, 1H), 7.79 (s, 1H), 7.75-7.70 (m, 1H), 7.69-7.58 (m, 5H), 7.54 (t, J 6.1, 1H), 7.37 (t, J 74, 1H), 7.22 (dd, J 1.8, 7.8, 1H).

Example 45

2-(2'-Chloro-3,5-difluoro-5'-methoxybiphenyl-4-ylcarbamoyl)benzoic acid

The title compound (41 mg) was obtained from intermediate 36 (40 mg, 0.15 mmol) and phthalic anhydride (44 mg, 0.3 mmol) as a white solid. M.P.: 167-172° C. $^1$H-NMR (δ ppm, DMSO-d$_6$, 400 MHz): 13.06 (s, 1H), 10.23 (s, 1H), 7.85 (d, J 7.6, 1H), 7.69-7.65 (m, 1H), 7.62-7.55 (m, 2H), 7.48 (d, J 8.6, 1H), 7.29 (d, J 8.3, 2H), 7.08-7.00 (m, 2H), 2.49 (s, 3H).

Example 46

2-(3,3',5-Trifluoro-5'-methoxybiphenyl-4-ylcarbamoyl)benzoic acid

The title compound (37 mg) was obtained from intermediate 37 (40 mg, 0.15 mmol) and phthalic anhydride (46 mg, 0.31 mmol) as a white solid. M.P.: 166.2-167.8° C. $^1$H-NMR (δ ppm, DMSO-d$_6$, 400 MHz): 13.04 (s, 1H), 10.22 (s, 1H), 7.84 (d, J 7.6, 1H), 7.70-7.52 (m, 5H), 7.23 (d, J 9.8, 1H), 7.18 (s, 1H), 6.88 (d, J 10.8, 1H), 3.85 (s, 3H).

Example 47

2-[4-(Benzo[d][1,3]dioxol-5-yl)-2,6-difluorophenylcarbamoyl]benzoic acid

The title compound (37 mg) was obtained from intermediate 38 (40 mg, 0.15 mmol) and phthalic anhydride (46 mg, 0.31 mmol) as a white solid. M.P.: 166.2-167.8° C. $^1$H-NMR (δ ppm, DMSO-d$_6$, 400 MHz): 13.02 (s, 1H), 10.14 (s, 1H), 7.83 (d, J 5.9, 1H), 7.67-7.64 (m, 1H), 7.60-7.56 (m, 2H), 7.47 (d, J 9.2, 2H), 7.38 (s, 1H), 7.26 (dd, J 1.5, 8.2, 1H), 7.01 (d, J 8.1, 1H), 6.07 (s, 2H).

Example 48

2-[4-(Benzo[d][1,3]dioxol-5-yl)-2-chloro-6-fluorophenylcarbamoyl]benzoic acid

The title compound (23 mg) was obtained from intermediate 39 (50 mg, 0.19 mmol) and phthalic anhydride (55 mg, 0.38 mmol) as a white solid. M.P.: 182-184.5° C. $^1$H-NMR (δ ppm, DMSO-d$_6$, 400 MHz): 13.00 (s, 1H), 10.21 (s, 1H), 7.81 (d, J 7.5, 1H), 7.68-7.56 (m, 5H), 7.39 (s, 1H), 7.26 (dd, J 1.4, 9.4, 1H), 7.01 (d, J 8.1, 1H), 6.08 (s, 2H).

Example 49

2-(3,5-Difluoro-3',4'-dimethoxybiphenyl-4-ylcarbamoyl)benzoic acid

The title compound (23 mg) was obtained from intermediate 40 (50 mg, 0.19 mmol) and phthalic anhydride (55 mg, 0.38 mmol) as a white solid. M.P.: 182-184.5° C. $^1$H-NMR (δ ppm, DMSO-d$_6$, 400 MHz): 13.03 (s, 1H), 10.14 (s, 1H), 7.83 (d, J 7.6, 1H), 7.67-7.64 (m, 1H), 7.58 (t, J 7.1, 2H), 7.52 (d, J 9.3, 2H), 7.33-7.28 (m, 2H), 7.04 (d, J 9, 1H), 3.86 (s, 3H), 3.79 (s, 3H).

Example 50

2-(3,3',5-Trifluoro-5'-methoxybiphenyl-4-ylcarbamoyl)benzoic acid

The title compound (35 mg) was obtained from intermediate 41 (40 mg, 0.14 mmol) and phthalic anhydride (44 mg, 0.28 mmol) as a white solid. M.P.: 164-166° C. $^1$H-NMR (δ ppm, DMSO-d$_6$, 400 MHz): 13.02 (s, 1H), 10.25 (s, 1H), 7.85-7.78 (m, 2H), 7.73 (d, J 11.2, 1H), 7.69-7.56 (m, 3H), 7.24 (d, J 9.9, 1H), 7.18 (s, 1H), 6.88 (d, J 10.8, 1H), 3.85 (s, 3H).

Example 51

2-(3,3'-Dichloro-5-fluoro-5'-methoxybiphenyl-4-ylcarbamoyl)benzoic acid

The title compound (41 mg) was obtained from intermediate 42 (40 mg, 0.14 mmol) and phthalic anhydride (44 mg, 0.28 mmol) as a white solid. M.P.: 159.6-161.2° C. $^1$H-NMR (δ ppm, DMSO-d$_6$, 400 MHz): 13.01 (s, 1H), 10.25 (s, 1H), 7.82 (d, J 7.9, 1H), 7.79 (s, 1H), 7.74 (d, J 10.7, 1H), 7.69-7.57 (m, 3H), 7.43 (s, 1H), 7.28 (s, 1H), 7.08 (s, 1H), 3.86 (s, 3H).

Example 52

2-[4-(2,3-Dihydrobenzofuran-5-yl)-2,6-difluorophenylcarbamoyl]benzoic acid

The title compound (46 mg) was obtained from intermediate 43 (50 mg, 0.2 mmol) and phthalic anhydride (59 mg, 0.40 mmol) as a white solid. M.P.: 176-177.5° C. $^1$H-NMR (δ ppm, DMSO-d$_6$, 400 MHz): 13.02 (s, 1H), 10.12 (s, 1H), 7.83 (d, J 7.6, 1H), 7.67 (s, 2H), 7.61-7.53 (m, 2H), 7.49 (d, J 7.6, 1H), 7.43 (d, J 9.2, 2H), 6.84 (d, J 8.3, 1H), 4.57 (t, J 8.7, 2H), 3.23 (t, J 8.6, 2H).

Example 53

2-[2-Chloro-4-(2,3-dihydrobenzofuran-5-yl)-6-fluorophenylcarbamoyl]benzoic acid

The title compound (44 mg) was obtained from intermediate 44 (40 mg, 0.15 mmol) and phthalic anhydride (44 mg, 0.30 mmol) as a white solid. M.P.: 177-179° C. $^1$H-NMR (δ ppm, DMSO-d$_6$, 400 MHz): 13.01 (s, 1H), 10.18 (s, 1H), 7.82 (d, J 7.6, 1H), 7.69-7.55 (m, 6H), 7.50 (d, J 8.2, 1H), 6.85 (d, J 8.4, 1H), 4.58 (t, J 8.8, 2H), 3.23 (t, J 8.8, 2H).

Example 54

2-[4-(1,3-Dimethyl-1H-indazol-5-yl)-2,6-difluorophenylcarbamoyl]benzoic acid

The title compound (16 mg) was obtained from intermediate 45 (25 mg, 0.09 mmol) and phthalic anhydride (27 mg, 0.18 mmol) as a white solid. M.P.: 276.4-277.5° C. $^1$H-NMR (δ ppm, DMSO-$d_6$, 400 MHz): 13.02 (s, 1H), 10.14 (s, 1H), 8.14 (s, 1H), 7.83 (d, J 7.2, 1H), 7.79 (d, J 9, 1H), 7.68-7.57 (m, 6H), 3.98 (s, 1H), 2.53 (s, 3H).

Example 55

2-(3'-Chloro-3,5-difluoro-5'-methoxybiphenyl-4-ylcarbamoyl)benzoic acid

The title compound (37 mg) was obtained from intermediate 46 (35 mg, 0.13 mmol) and phthalic anhydride (39 mg, 0.25 mmol) as a white solid. M.P.: 171-175° C. $^1$H-NMR (δ ppm, DMSO-$d_6$, 400 MHz): 13.04 (s, 1H), 10.22 (s, 1H), 7.83 (d, J 7.7, 1H), 7.70-7.55 (m, 5H), 7.42 (s, 1H), 7.28 (s, 1H), 7.07 (s, 1H), 3.85 (s, 3H).

Example 56

2-(3-Chloro-5-fluoro-3',4'-dimethoxybiphenyl-4-ylcarbamoyl)benzoic acid

The title compound (24 mg) was obtained from intermediate 47 (30 mg, 0.1 mmol) and phthalic anhydride (31 mg, 0.2 mmol) as a white solid. M.P.: 179.6-182.1° C. $^1$H-NMR (δ ppm, DMSO-$d_6$, 400 MHz): 13.0 (s, 1H), 10.18 (s, 1H), 7.82 (d, J 7.7, 1H), 7.72 (s, 1H), 7.68-7.57 (m, 4H), 7.33-7.28 (m, 2H), 7.04 (d, J 8.8, 1H), 3.86 (s, 3H), 3.79 (s, 3H).

Example 57

2-(2',3-Dichloro-5-fluoro-5'-methoxybiphenyl-4-ylcarbamoyl)benzoic acid

The title compound (54 mg) was obtained from intermediate 48 (30 mg, 0.1 mmol) and phthalic anhydride (30 mg, 0.2 mmol) as a white solid. M.P.: 165-167° C. $^1$H-NMR (δ ppm, DMSO-$d_6$, 400 MHz): 13.03 (s, 1H), 10.27 (s, 1H), 7.83 (d, J 7.4, 1H), 7.70-7.57 (m, 3H), 7.51-7.47 (m, 2H), 7.43 (d, J 10, 1H), 7.08-7.01 (m, 2H), 3.80 (s, 3H).

Example 58

2-(2',3,5-Trifluoro-5'-methoxybiphenyl-4-ylcarbamoyl)benzoic acid

The title compound (23 mg) was obtained from intermediate 49 (30 mg, 0.1 mmol) and phthalic anhydride (38 mg, 0.22 mmol) as a white solid. M.P.: 173.4-176.5° C. $^1$H-NMR (δ ppm, DMSO-$d_6$, 400 MHz): 13.04 (s, 1H), 10.24 (s, 1H), 7.84 (d, J 7.7, 1H), 7.67 (t, J 7.1, 1H), 7.60 (t, J 8, 2H), 7.41 (d, J 8.6, 2H), 7.27 (t, J 9.5, 1H), 7.15-7.12 (m, 1H), 7.03-6.96 (m, 1H), 3.80 (s, 3H).

Example 59

2-(4'-Chloro-3,5-difluoro-3'-methoxybiphenyl-4-ylcarbamoyl)benzoic acid

The title compound (42 mg) was obtained from intermediate 50 (80 mg, 0.3 mmol) and phthalic anhydride (85 mg, 0.6 mmol) as a white solid. M.P.: 156.1-158.3° C. $^1$H-NMR (δ ppm, DMSO-$d_6$, 400 MHz): 13.04 (s, 1H), 10.21 (s, 1H), 7.84 (d, J 12.6, 2H), 7.70-7.57 (m, 4H), 7.55-7.49 (m, 1H), 7.46 (s, 1H), 7.34 (d, J 8.1, 1H), 3.97 (s, 3H).

Example 60

2-(3,4'-Dichloro-5-fluoro-3'-methoxybiphenyl-4-ylcarbamoyl)benzoic acid

The title compound (63 mg) was obtained from intermediate 51 (80 mg, 0.27 mmol) and phthalic anhydride (83 mg, 0.55 mmol) as a white solid. M.P.: 147.6-150.4° C. $^1$H-NMR (δ ppm, DMSO-$d_6$, 400 MHz): 13.02 (s, 1H), 10.24 (s, 1H), 7.85-7.79 (m, 2H), 7.73 (d, J 7.8, 1H), 7.70-7.58 (m, 3H), 7.51 (d, J 8.1, 1H), 7.46 (s, 1H), 7.34 (d, J 6.5, 1H), 3.97 (s, 3H).

Example 61

2-(3-chloro-2',5-difluoro-5'-methoxybiphenyl-4-ylcarbamoyl)benzoic acid

The title compound (40 mg) was obtained from intermediate 52 (70 mg, 0.26 mmol) and phthalic anhydride (76 mg, 0.52 mmol) as an off-white solid. M.P.: 160.1-163.5° C. $^1$H-NMR (δ ppm, DMSO-$d_6$, 400 MHz): 13.05 (s, 1H), 10.28 (s, 1H), 7.83 (d, J 7.3, 1H), 7.70-7.51 (m, 5H), 7.28 (d, J 9.5, 1H), 7.17-7.11 (m, 1H), 7.05-6.97 (m, 1H), 3.81 (s, 3H).

Example 62

2-(3,4',5-trifluoro-3'-methoxybiphenyl-4-ylcarbamoyl)benzoic acid

The title compound (60 mg) was obtained from intermediate 53 (200 mg, 0.79 mmol) and phthalic anhydride (230 mg, 1.58 mmol) as an off-white solid. M.P.: 125.6-128.8° C. $^1$H-NMR (δ ppm, DMSO-$d_6$, 400 MHz): 13.04 (s, 1H), 10.18 (s, 1H), 7.83 (d, J 7.6, 1H), 7.68-7.64 (m, 1H), 7.63-7.54 (m, 4H), 7.50 (d, J 8, 1H), 7.35-7.28 (m, 2H), 3.94 (s, 3H).

Example 63

2-[2,6-difluoro-4-(3-methyl-1H-indol-5-yl)phenylcarbamoyl]benzoic acid

The title compound (84 mg) was obtained from intermediate 54 (66 mg, 0.25 mmol) and phthalic anhydride (75 mg, 0.51 mmol) as a white solid. M.P.: 182-186.5° C. $^1$H-NMR (δ ppm, DMSO-$d_6$, 400 MHz): 13.03 (s, 1H), 10.86 (s, 1H), 10.11 (s, 1H), 7.87 (s, 1H), 7.83 (d, J 7.3, 1H), 7.69-7.63 (m, 1H) 7.62-7.57 (m, 2H), 7.52 (d, J 9.3, 2H), 7.45 (d, J 8.5, 1H), 7.40 (d, J 8.4, 1H), 7.15 (s, 1H), 2.31 (s, 3H).

Example 64

2-[2,6-difluoro-4-(3-methyl-1H-indazol-5-yl)phenyl-carbamoyl]benzoic acid

The title compound (38 mg) was obtained from intermediate 55 (50 mg, 0.19 mmol) and phthalic anhydride (57 mg, 0.39 mmol) as a white solid. M.P.: 179-184° C. $^1$H-NMR (δ ppm, DMSO-d$_6$, 400 MHz): 12.79 (bs, 1H), 10.15 (s, 1H), 8.14 (s, 1H), 7.84 (d, J 7.3, 1H), 7.73 (d, J 7.3, 1H), 7.69-7.65 (m, 1H), 7.62-7.55 (m, 4H), 7.53 (d, J 8.7, 1H), 6.02 (bs, 1H), 2.54 (s, 3H).

Example 65

2-(3-chloro-3'-ethyl-5-fluorobiphenyl-4-ylcarbamoyl)benzoic acid

The title compound (38 mg) was obtained from intermediate 56 (50 mg, 0.19 mmol) and phthalic anhydride (57 mg, 0.39 mmol) as a white solid. M.P.: 179-184° C. $^1$H-NMR (δ ppm, DMSO-d$_6$, 400 MHz): 13.02 (bs, 1H), 10.22 (s, 1H), 7.82 (d, J 7.7, 1H), 7.74-7.54 (m, 7H), 7.39 (t, J 7.6, 1H), 7.27 (d, J 7.6, 1H). 2.68 (q, J 7.6, 2H), 1.23 (t, J 7.6, 3H).

Example 66

2-(3-chloro-3'-ethoxy-2',5-difluorobiphenyl-4-ylcarbamoyl)benzoic acid

The title compound (54 mg) was obtained from intermediate 57 (60 mg, 0.21 mmol) and phthalic anhydride (63 mg, 0.42 mmol) as a white solid. M.P.: 160-163° C. $^1$H-NMR (δ ppm, DMSO-d$_6$, 400 MHz): 13.04 (s, 1H), 10.29 (s, 1H), 7.83 (d, J 7.6, 1H), 7.70-7.55 (m, 4H), 7.51 (d, J 10, 1H), 7.26-7.21 (m, 2H), 7.16-7.10 (m, 1H), 4.14 (q, J 6.8, 2H), 1.37 (t, J 6.8, 3H).

Example 67

2-[2-chloro-4-(2,3-dihydrobenzo[b][1,4]dioxin-6-yl)-6-fluorophenylcarbamoyl]benzoic acid The title compound (54 mg) was obtained from intermediate 58 (60 mg, 0.21 mmol) and phthalic anhydride (63 mg, 0.42 mmol) as a white solid. M.P.: 147-151° C. $^1$H-NMR (δ ppm, DMSO-d$_6$, 400 MHz): 13.02 (s, 1H), 10.19 (s, 1H), 7.82 (d, J 7.5, 1H), 7.68-7.53 (m, 5H), 7.29 (d, J 2.1, 1H), 7.24 (dd, J 2.1, 8.4, 1H), 6.94 (d, J 8.4, 1H), 4.28 (s, 4H).

Example 68

2-[3-chloro-5-fluoro-3'-(2,2,2-trifluoroethoxy)biphenyl-4-ylcarbamoyl]benzoic acid The title compound (21 mg) was obtained from intermediate 59 (80 mg, 0.25 mmol) and phthalic anhydride (74 mg, 0.5 mmol) as a white solid. M.P.: 133-137° C. $^1$H-NMR (δ ppm, DMSO-d$_6$, 400 MHz): 13.02 (s, 1H), 10.25 (s, 1H), 7.86-7.79 (m, 2H), 7.72 (d, J 10.5, 1H), 7.70-7.55 (m, 3H), 7.48-7.42 (m, 3H), 7.15-7.06 (m, 1H), 4.88 (q, J 9.3, 2H).

Example 69

2-(3-fluoro-3'-methoxybiphenyl-4-ylcarbamoyl)benzoic acid

The title compound (82 mg) was obtained from intermediate 60 (150 mg, 0.69 mmol) and phthalic anhydride (200 mg, 1.4 mmol) as a white solid. M.P.: 141-143° C. $^1$H-NMR (δ ppm, DMSO-d$_6$, 400 MHz): 13.04 (s, 1H), 10.23 (s, 1H), 7.97-7.93 (m, 1H), 7.87 (d, J 7.5, 1H), 7.70-7.50 (m, 5H), 7.37 (t, J 7.9, 1H), 7.29-7.20 (m, 2H), 6.94 (d, J 6.1, 1H), 3.82 (s, 3H).

Example 70

2-(3'-ethoxybiphenyl-4-ylcarbamoyl)benzoic acid

The title compound (82 mg) was obtained from intermediate 61 (150 mg, 0.69 mmol) and phthalic anhydride (200 mg, 1.4 mmol) as a white solid. M.P.: 141-143° C. $^1$H-NMR (δ ppm, DMSO-d$_6$, 400 MHz): 13.03 (s, 1H), 10.41 (s, 1H), 7.87 (d, J 7.6, 1H), 7.76 (d, J 8.6, 2H), 7.69-7.61 (m, 3H), 7.60-7.52 (m, 2H), 7.33 (t, J 7.9, 1H), 7.20 (d, J 7.8, 1H), 7.14 (s, 1H), 6.87 (dd, J 2.1, 8.0, 1H), 4.07 (q, J 7, 2H), 1.34 (t, J 7, 2H).

Example 71

2-[3'-(ethylthio)-3,5-difluorobiphenyl-4-ylcarbamoyl]benzoic acid

The title compound (65 mg) was obtained from intermediate 62 (150 mg, 0.69 mmol) and phthalic anhydride (200 mg, 1.4 mmol) as a white solid. M.P.: 137.8-142.1° C. $^1$H-NMR (δ ppm, DMSO-d$_6$, 400 MHz): 13.03 (s, 1H), 10.2 (s, 1H), 7.84 (d, J 7.6, 1H), 7.70-7.52 (m, 7H), 7.42 (t, J 7.7, 1H), 7.34 (d, J 7.6, 1H), 3.08 (q, J 7.3, 2H), 1.26 (t, J 7.3, 3H). MS (m/z): 413.80 ([M+H]$^+$).

Example 72

2-[3'-(ethylsulfinyl)-3,5-difluorobiphenyl-4-ylcarbamoyl]benzoic acid

Oxone (241 mg, 0.39 mmol) was added to a solution of example 71 (210 mg, 0.43 mmol) in water-acetone (1:1, 4.2 ml) and stirred at RT for 2 h. Solid that formed in reaction mixture was filtered and dried to obtain the title compound (95 mg) as a white solid. $^1$H-NMR (δ ppm, DMSO-d$_6$, 400 MHz): 13.04 (s, 1H), 10.26 (s, 1H), 8.19 (s, 1H), 8.14 (d, J 7.8, 1H), 7.91 (d, J 7.8, 1H), 7.84 (d, J 7.3, 1H), 7.77 (t, J 7.8, 1H), 7.72-7.64 (m, 3H), 7.62-7.56 (m, 2H), 3.41 (q, J 7.3, 2H), 1.13 (t, J 7.3, 3H). MS (m/z): 430.07 ([M+H]$^+$).

Example 73

2-(3'-cyclopropoxy-3,5-difluorobiphenyl-4-ylcarbamoyl)benzoic acid

The title compound (96 mg) was obtained from intermediate 63 (160 mg, 0.61 mmol) and phthalic anhydride (181 mg, 1.2 mmol) as a white solid. M.P.: 125-127° C. MS (m/z): 410.2 ([M+H]$^+$).

Example 74

2-(3'-ethoxy-3,5-difluorobiphenyl-4-ylcarbamoyl)-6(5)-methylbenzoic acid

The title compound (75 mg) was obtained from intermediate 5 (200 mg, 0.8 mmol) and 4-methylisobenzofuran-1,3-dione (260 mg, 1.6 mmol) as a white solid. M.P.: 138-140° C. $^1$H-NMR (δ ppm, DMSO-d$_6$, 400 MHz): 13.02 (s, 1H), 10.09 (s, 1H), 7.77 (d, J 7.8, 1H), 7.52 (d, J 9.3, 3H), 7.47-7.41 (m, 1H), 7.38 (t, J 7.9, 1H), 7.32-7.24 (m, 2H), 6.98-6.95 (m, 1H), 4.11 (q, J 6.9, 2H), 2.41 (s, 3H), 1.35 (t, J 6.9, 3H). MS (m/z): 410.07 ([M−H]$^-$).

Example 75

2-[4-(3-ethyl-1H-indol-5-yl)-2,6-difluorophenylcarbamoyl]benzoic acid

The title compound (75 mg) was obtained from intermediate 65 (250 mg, 0.992 mmol) and phthalic anhydride (271 mg, 1.84 mmol) as a white solid. M.P.: 157.9-160.9° C. $^1$H-NMR (δ ppm, DMSO-d$_6$, 400 MHz): 13.03 (s, 1H), 10.88 (s, 1H), 10.11 (s, 1H), 7.89 (s, 1H), 7.83 (d, J 7.3, 1H), 7.69-7.63 (m, 1H), 7.62-7.56 (m, 2H), 7.51 (d, J 9.3, 2H), 7.47-7.39 (m, 2H), 7.16 (s, 1H), 2.75 (q, J 7.4, 2H), 1.28 (t, J 7.4, 3H). MS (m/z): 418.75 ([M−H]$^-$).

Example 76

2-(3'-ethoxy-3,5-difluorobiphenyl-4-ylcarbamoyl) nicotinic acid

The title compound (15 mg) was obtained from intermediate 5 (150 mg, 0.6 mmol) and furo[3,4-b]pyridine-5,7-dione (180 mg, 1.2 mmol) as a grey solid. M.P.: 207-210° C. MS (m/z): 399.08 ([M+H]$^+$).

Example 77

4-(3'-ethoxy-3,5-difluorobiphenyl-4-ylcarbamoyl) nicotinic acid

The title compound (10 mg) was obtained from intermediate 5 (100 mg, 0.4 mmol) and furo[3,4-c]pyridine-1,3-dione (119 mg, 0.8 mmol) as a white solid. M.P.: 219-221° C. MS (m/z): 399.01 ([M+H]$^+$). The regiochemical assignment is based on earlier reports, e.g. Nailton et. al. Bioorganic & Medicinal Chemistry Letters 2010, 20(1), 74-77.

Example 78

2-[3'-(ethylthio)-2,3,5,6-tetrafluorobiphenyl-4-ylcarbamoyl]benzoic acid

The title compound (82 mg) was obtained from intermediate 66 (280 mg, 0.93 mmol) and phthalic anhydride (206 mg, 1.4 mmol) as a white solid. M.P.: 158-160° C. MS (m/z): 448.29 ([M−H]$^-$).

Example 79

2-(2'-chloro-2-fluoro-5'-methoxybiphenyl-4-ylcarbamoyl)benzoic acid

The title compound (50 mg) was obtained from intermediate 67 (210 mg, 0.83 mmol) and phthalic anhydride (185 mg, 1.2 mmol) as a grey solid. M.P.: 185-187° C. MS (m/z): 398.24 ([M−H]$^-$).

Example 80

2-(3-fluoro-3'-propoxybiphenyl-4-ylcarbamoyl)benzoic acid

The title compound (14 mg) was obtained from intermediate 68 (170 mg, 0.7 mmol) and phthalic anhydride (153 mg, 1.03 mmol) as a white solid. M.P.: 116-119° C. MS (m/z): 394.2 ([M+H]$^+$).

Example 81

2-(3'-propoxybiphenyl-4-ylcarbamoyl)benzoic acid

The title compound (60 mg) was obtained from intermediate 69 (60 mg, 0.26 mmol) and phthalic anhydride (58 mg, 0.4 mmol) as a white solid. M.P.: 152-154° C. MS (m/z): 376.2 ([M+H]$^+$).

Example 82

2-[3'-(ethylthio)-2-fluorobiphenyl-4-ylcarbamoyl]benzoic acid

The title compound (200 mg) was obtained from intermediate 70 (430 mg, 1.74 mmol) and phthalic anhydride (380 mg, 2.6 mmol) as a white solid. M.P.: 74-76° C. MS (m/z): 395.72 ([M+H]$^+$).

Example 83

2-[3,5-difluoro-3'-(2,2,2-trifluoroethoxy)biphenyl-4-ylcarbamoyl]benzoic acid

The title compound (80 mg) was obtained from intermediate 71 (88 mg, 0.29 mmol) and phthalic anhydride (86 mg, 0.58 mmol) as a white solid. M.P.: 152-156° C. $^1$H-NMR (δ ppm, DMSO-d$_6$, 400 MHz): 13.04 (s, 1H), 10.19 (s, 1H), 7.84 (d, J 7.2, 1H), 7.68-7.53 (m, 6H), 7.46-7.41 (m, 2H), 7.13-7.06 (m, 1H), 4.87 (q, J 9, 2H).

Example 84

2-(3'-ethyl-3,5-difluorobiphenyl-4-ylcarbamoyl)benzoic acid

The title compound (15 mg) was obtained from intermediate 72 (170 mg, 0.73 mmol) and phthalic anhydride (210 mg, 1.45 mmol) as a white solid. M.P.: 132-136° C. $^1$H-NMR (δ ppm, DMSO-d$_6$, 400 MHz): 13.04 (s, 1H), 10.18 (s, 1H), 7.83 (d, J 7.3, 1H), 7.69-7.48 (m, 7H), 7.39 (t, J 7.6, 1H), 7.26 (d, J 7.3, 1H), 2.67 (q, J 7.6, 2H), 1.23 (t, J 7.6, 3H).

Example 85

2-(biphenyl-4-ylcarbamoyl)benzoic acid

The title compound (46 mg) was obtained from biphenyl-4-amine (65 mg, 0.38 mmol) and phthalic anhydride (85 mg, 0.58 mmol) as a white solid. M.P.: 276-278° C. MS (m/z): 318.1 ([M+H]$^+$).

Example 86

2-(2'-chlorobiphenyl-4-ylcarbamoyl)benzoic acid

The title compound (223 mg) was obtained from intermediate 73 (170 mg, 0.83 mmol) and phthalic anhydride (185 mg, 1.25 mmol) as a white solid. M.P.: 243-247° C. MS (m/z): 352.1 ([M+H]$^+$).

Example 87

2-(3'-methoxybiphenyl-4-ylcarbamoyl)benzoic acid

The title compound (223 mg) was obtained from intermediate 74 (170 mg, 0.83 mmol) and phthalic anhydride (185 mg, 1.25 mmol) as a white solid. M.P.: 243-247° C. MS (m/z): 348.2 ([M+H]$^+$).

Example 88

2-[3'-(trifluoromethoxy)biphenyl-4-ylcarbamoyl] benzoic acid

The title compound (110 mg) was obtained from intermediate 75 (280 mg, 1.1 mmol) and phthalic anhydride (245 mg, 1.66 mmol) as a white solid. M.P.: 154.4-158.5° C. MS (m/z): 402.2 ([M+H]$^+$).

Example 89

2-[3'-(ethylthio)-2,6-difluorobiphenyl-4-ylcarbamoyl]benzoic acid

The title compound (50 mg) was obtained from intermediate 76 (240 mg, 0.9 mmol) and phthalic anhydride (200 mg, 1.35 mmol) as a white solid. M.P.: 162-167° C. MS (m/z): 414.2 ([M+H]$^+$).

Example 90

2-(3'-ethylbiphenyl-4-ylcarbamoyl)benzoic acid

The title compound (96 mg) was obtained from intermediate 77 (100 mg, 0.5 mmol) and phthalic anhydride (110 mg, 0.76 mmol) as an off-white solid. M.P.: 178-182° C. MS (m/z): 346.2 ([M+H]$^+$).

Example 91

2-(3'-butoxy-2,3,5,6-tetrafluorobiphenyl-4-ylcarbamoyl)benzoic acid

The title compound (130 mg) was obtained from intermediate 78 (180 mg, 0.57 mmol) and phthalic anhydride (127 mg, 0.86 mmol) as a white solid. M.P.: 215.5-218.5° C. MS (m/z): 460.18 ([M−H]$^-$).

Example 92

2-(3'-butoxy-3-fluorobiphenyl-4-ylcarbamoyl)benzoic acid

The title compound (130 mg) was obtained from intermediate 79 (170 mg, 0.65 mmol) and phthalic anhydride (145 mg, 0.98 mmol) as a white solid. M.P.: 102-105° C. MS (m/z): 406.17 ([M−H]$^-$).

Example 93

2-[3,5-difluoro-3'-(trifluoromethoxy)biphenyl-4-ylcarbamoyl]benzoic acid

The title compound (50 mg) was obtained from intermediate 8 (200 mg, 0.69 mmol) and phthalic anhydride (150 mg, 1.03 mmol) as a white solid. M.P.: 158-160° C. MS (m/z): 435.93 ([M−H]$^-$).

Example 94

2-(3'-cyclopropoxy-3-fluorobiphenyl-4-ylcarbamoyl)benzoic acid

The title compound (120 mg) was obtained from intermediate 80 (100 mg, 0.41 mmol) and phthalic anhydride (91 mg, 0.62 mmol) as a white solid. M.P.: 134.5-137.5° C. MS (m/z): 390.27 ([M−H]$^-$).

Example 95

2-(3'-cyclopropoxybiphenyl-4-ylcarbamoyl)benzoic acid

The title compound (90 mg) was obtained from intermediate 81 (98 mg, 0.43 mmol) and phthalic anhydride (96 mg, 0.65 mmol) as a white solid. M.P.: 150.2-154.3° C. MS (m/z): 372.14 ([M−H]$^-$).

Example 96

2-(3'-butoxybiphenyl-4-ylcarbamoyl)benzoic acid

The title compound (37 mg) was obtained from intermediate 82 (80 mg, 0.33 mmol) and phthalic anhydride (73 mg, 0.5 mmol) as a white solid. M.P.: 155-157° C. MS (m/z): 388.38 ([M−H]$^-$).

Example 97

2-(3'-butoxy-2-fluorobiphenyl-4-ylcarbamoyl)benzoic acid

The title compound (171 mg) was obtained from intermediate 83 (240 mg, 0.92 mmol) and phthalic anhydride (205 mg, 1.3 mmol) as a white solid. M.P.: 164-167° C. MS (m/z): 406.31 ([M−H]$^-$).

Example 98

2-(3'-Butoxy-2,6-difluorobiphenyl-4-ylcarbamoyl) benzoic acid

The title compound (91 mg) was obtained from intermediate 84 (170 mg, 0.6 mmol) and phthalic anhydride (136 mg, 0.9 mmol) as an off-white solid. M.P.: 181.1-184.2° C. MS (m/z): 423.95 ([M−H]$^-$).

Example 99

2-[2,6-Difluoro-4-(3-propyl-1H-indol-5-yl)phenylcarbamoyl]benzoic acid

The title compound (150 mg) was obtained from intermediate 86 (240 mg, 0.84 mmol) and phthalic anhydride (186 mg, 1.25 mmol) as a white solid. M.P.: 76-80° C. $^1$H-NMR (δ ppm, DMSO-d$_6$, 400 MHz): 10.88 (s, 1H), 7.88 (s, 1H), 7.81 (d, J 6.6, 1H), 7.75-7.71 (m, 1H), 7.53-7.47 (m, 5H), 7.44-7.38 (m, 2H), 7.14 (s, 1H), 2.72 (t, J 7.4, 2H), 1.69 (h, J 7.5, 2H), 0.96 (t, J 7.3, 3H). MS (m/z): 433.13 ([M−H]$^-$).

Example 100

2-[2-Chloro-4-(3-ethyl-1H-indol-5-yl)-6-fluorophenylcarbamoyl]benzoic acid

The title compound (25 mg) was obtained from intermediate 87 (60 mg, 0.21 mmol) and phthalic anhydride (46 mg, 0.31 mmol) as a white solid. M.P.: 98-102° C. MS (m/z): 435.23 ([M−H]⁻).

Biological Assay

The properties of the compounds of this invention may be confirmed by a number of biological and pharmacological assays. The biological and pharmacological assay which can be been carried out with the compounds according to the invention and/or their pharmaceutically acceptable salts are exemplified below. Similarly the compounds of the present invention may also be tested using other assays such as cytokine (IL-17 and interferon gamma) estimation in human whole blood and PBMCs.

The compounds of the invention may also be tested in various animal models to establish the various therapeutic potential of the compounds of this invention.

1. In-Vitro DHODH Inhibition Assays

The properties of the compounds of this invention may be confirmed by a number of biological/pharmacological assays. The biological/pharmacological assay which can be been carried out with the compounds according to the invention and/or their pharmaceutically acceptable salts is exemplified below. Similarly the compounds of the present invention may also be tested using other assays such as cytokine (IL-17, interferon gamma etc.) estimation in human whole blood and PBMCs.

Dihydro-Orotate Dehydrogenase Inhibition Assay

Dihydro-orotate dehydrogenase (DHODH) catalyzes the reduction of dihydro-orotate to orotate during de novo biosynthesis of pyrimidines. Inhibition of DHODH activity in U937 membrane preparations was measured by the dihydro-orotate driven reduction of 2,6 dichloroindophenol (DCIP).

U937 cells were homogenized in 20 mM Tris/HCl (pH 7.2) containing 1 mM EDTA. Cell debris was removed by centrifugation at 2000×g for 10 min. Membrane fractions were pelleted by centrifuging the supernatant at 160000×g for 1 h at 4° C. and washed with buffer containing 125 mM sucrose and 150 mM NaCl. Following washes, the pellet was dissolved in 20 mM Tris/HCl containing 150 mM NaCl, 1 mM EDTA, and 1% octyl glucoside on ice for 1 h. Particulate matter was removed by centrifugation at 100000×g for 1 h at 4° C. Extracts (~50 µg protein) were added to an assay mixture (200 µM CoQD, 500 µM dihydro-orotate, 75 µM DCIP in 100 mM HEPES pH 8.0, 150 mM NaCl, 10% glycerol, 0.05% Triton X-100) containing inhibitors at desired concentrations in a 96-well plate. The mixture was incubated at 37° C. for 4 h before measuring the change in absorbance on a plate reader (BMG Labtech., Germany) at 600 nm. Data were analyzed using GraphPad Prism. $IC_{50}$ for each compound was determined based on the percent inhibition of dihydro-orotate reduction.

Results:

TABLE 2

| Compound | h- DHODH % inhibition 1 uM | IC50 (nM) |
|---|---|---|
| Teriflunomide# | 77.16 | 875.9 |
| Example 1 | 53.27 | 740.8 |
| Example 2 | 12.18 | |
| Example 3 | 14.27 | |
| Example 4 | 42.95 | |
| Example 5 | 85.70 | 49.8 |
| Example 6 | 2.26 | |
| Example 7 | 4.53 | |
| Example 8 | 85.75 | 90.03 |
| Example 9 | 10.33 | |
| Example 10 | 46.78 | |
| Example 11 | — | |
| Example 12 | 64.47 | 204.7 |
| Example 13 | 76.36 | 150 |
| Example 14 | 52.19 | |
| Example 15 | 75.48 | 129.2 |
| Example 16 | 28.04 | |
| Example 17 | 50.26 | |
| Example 18 | 62.23 | 294.1 |
| Example 19 | 82.18 | 44.65 |
| Example 20 | 55.37 | |
| Example 21 | 56.44 | |
| Example 22 | 41.83 | |
| Example 23 | 47.16 | |
| Example 24 | 40.18 | |
| Example 25 | 60.17 | |
| Example 26 | 85.34 | 122 |
| Example 27 | 82.93 | 147.5 |
| Example 28 | 12.90 | |
| Example 29 | 94.02 | 7.93 |
| Example 30 | 67.97 | |
| Example 31 | 73.51 | 44.65 |
| Example 32 | 58.91 | |
| Example 33 | | |
| Example 34 | 95.78 | 62.52 |
| Example 35 | 86.45 | 11.85 |
| Example 36 | — | |
| Example 37 | 14.77 | |
| Example 38 | 27.84 | |
| Example 39 | 74.43 | 177.8 |
| Example 40 | — | |
| Example 41 | 72.16 | 83.39 |
| Example 42 | 76.91 | 24.04 |
| Example 43 | 58.24 | 180.8 |
| Example 44 | 71.12 | 90.63 |
| Example 45 | 96.21 | 44.09 |
| Example 46 | 55.97 | |
| Example 47 | 55.19 | |
| Example 48 | 47.10 | |
| Example 49 | — | |
| Example 50 | 28.65 | |
| Example 51 | 26.56 | |
| Example 52 | 12.82 | |
| Example 53 | — | |
| Example 54 | — | |
| Example 55 | 44.50 | |
| Example 56 | 1.77 | |
| Example 57 | 68.11 | |
| Example 58 | 76.14 | |
| Example 59 | 34.54 | |
| Example 60 | 41.77 | |
| Example 61 | 73.73 | |
| Example 62 | 12.37 | |
| Example 63 | 76.68 | 22.0 |
| Example 64 | 23.37 | |
| Example 65 | 71.16 | 146.2 |
| Example 66 | 87.51 | 84.42 |
| Example 67 | 54.12 | |
| Example 68 | 86.47 | 62.2 |
| Example 69 | 21.98 | |
| Example 70 | 14.02 | |
| Example 71 | 84.84 | 53.51 |
| Example 72 | 16.92 | |
| Example 73* | 84.98 | 28.01 |
| Example 74* | 7.14 | |
| Example 75* | 100 | 1.52 |
| Example 76* | 44.05 | |
| Example 77* | 50.22 | |

TABLE 2-continued

| Compound | h-DHODH % inhibition 1 uM | IC50 (nM) |
|---|---|---|
| Example 78* | 32.92 | |
| Example 79* | — | |
| Example 80* | 47.65 | |
| Example 81* | 11.25 | |
| Example 82* | 57.87 | |
| Example 83* | 43.56 | |
| Example 84* | 36.61 | |
| Example 85* | 15.13 | |
| Example 86* | 33.61 | |
| Example 87* | 30.25 | |
| Example 88* | 62.18 | |
| Example 89 | — | |
| Example 90 | 29.41 | |
| Example 91 | 42.39 | |
| Example 92 | 9.65 | |
| Example 93 | 10.46 | |
| Example 94 | 13.86 | |
| Example 95 | 1.49 | |
| Example 96 | — | |
| Example 97 | — | |
| Example 98 | 30.97 | |
| Example 99 | 42.58 | |
| Example 100 | 58.71 | | compound tested at 10 uM;
*compound tested at 0.3 uM

2. Inhibition of IL-17 Release from Mouse Splenocytes:

Splenocytes isolated from Balb/c mice were re-suspended in RPMI medium at a concentration of 1×10$^6$ cells/ml and seeded in a 6 well plate. Cells were incubated with desired concentrations of the inhibitor for 15 min prior to induction with 10 ng/ml PMA+1 µM ionomycin. After a 3 h incubation, supernatant was collected and analyzed for IL-17 concentration using an ELISA kit. Data were analysed using GraphPad Prism. IC$_{50}$ values for each compound were determined based on the percent inhibition due to the test compound compared to the control.

Results:

TABLE 3

| Compound | IL-17 % inhibition @ 10 µM | IC50 (µM) |
|---|---|---|
| Teriflunomide | 0 | |
| Example 1 | 6.13 | |
| Example 2 | 29.25 | |
| Example 3 | 17.15 | |
| Example 4 | 11.23 | |
| Example 5 | 30.79 | |
| Example 6 | 9.52 | |
| Example 7 | 8.58 | |
| Example 8 | 35.43 | |
| Example 9 | 26.89 | |
| Example 10 | 6.82 | |
| Example 11 | 2.62 | |
| Example 12 | 2.96 | |
| Example 13 | 3.43 | |
| Example 14 | 13.49 | |
| Example 15 | 57.45 | |
| Example 16 | 12.35 | |
| Example 17 | 11.11 | |
| Example 18 | 12.09 | |
| Example 19 | 19.00 | |
| Example 20 | 24.27 | |
| Example 21 | 17.84 | |
| Example 22 | 12.91 | |
| Example 23 | 14.97 | |
| Example 24 | 8.46 | |
| Example 25 | 17.54 | |
| Example 26 | 8.70 | |
| Example 27 | 12.39 | |
| Example 28 | 18.83 | |
| Example 29 | 46.09 | 18.76 |
| Example 30 | 10.29 | |
| Example 31 | 21.10 | |
| Example 32 | 11.83 | |
| Example 33 | 14.02 | |
| Example 34 | 5.96 | |
| Example 35 | 7.76 | |
| Example 36 | 45.45 | |
| Example 37 | 17.84 | |
| Example 38 | 9.35 | |
| Example 39 | 5.87 | |
| Example 40 | 8.79 | |
| Example 41 | 7.16 | |
| Example 42 | 22.26 | |
| Example 43 | 6.82 | |
| Example 44 | 35.00 | |
| Example 45 | 48.51 | |
| Example 46 | 3.69 | |
| Example 47 | 6.22 | |
| Example 48 | 22.04 | |
| Example 49 | 3.95 | |
| Example 50 | 10.08 | |
| Example 51 | 10.85 | |
| Example 52 | 13.77 | |
| Example 53 | 8.28 | |
| Example 54 | 22.56 | |
| Example 55 | 5.66 | |
| Example 56 | 5.49 | |
| Example 58 | 5.46 | |
| Example 59 | 7.36 | |
| Example 60 | 20.29 | |
| Example 61 | 4.23 | |
| Example 62 | 8.34 | |
| Example 63 | 0 | |
| Example 64 | 15.33 | |
| Example 65 | 11.04 | |
| Example 67 | 3.56 | |
| Example 69 | 5.54 | |
| Example 70 | 48.43 | 9.11 |
| Example 71 | 27.77 | |
| Example 72 | 7.36 | |
| Example 73 | 7.86 | |
| Example 74 | 13.81 | |
| Example 75 | 29.40 | 32.86 |
| Example 76 | 7.88 | |
| Example 77 | 9.25 | |
| Example 78 | 11.14 | |
| Example 79 | 24.63 | |
| Example 80 | 20.07 | |
| Example 81 | 23.00 | |
| Example 82 | 17.59 | |
| Example 83 | 8.79 | |
| Example 84 | 12.12 | |
| Example 85 | 13.03 | |
| Example 86 | 23.84 | |
| Example 87 | 20.91 | |
| Example 88 | 19.09 | |
| Example 89 | 25.54 | |
| Example 90 | 22.35 | |

3. Determination of IL-17 Producing Cells by Flow Cytometry:

PBMC isolated from human blood were stimulated and treated with desired concentrations of the test compounds prior to stimulation with Cytostim (Milteny Biotech, Germany). After 4 h, IL-17 secreting cells were stained using the IL-17 secretion assay kit as per the manufacturer's instruction and normalized to total CD4+ cells within the PBMC population. Data were analyzed using Graph pad prism. For instance example 29 showed a 43.6% inhibition of IL17 when tested at at 1 uM. The results indicate the potential of the compounds of invention to inhibit IL17 release independent of DHODH inhibition.

4. In Vitro Inhibition of Proliferation and Cytokine Release in Peripheral Blood Mononuclear Cells (PBMC)

a. Inhibition of PHA Induced PBMC Proliferation:

PBMC from freshly collected HWB was isolated by density gradient using Histopaque and seeded in a 96-well plate. Wells were incubated with desired concentrations of the inhibitor for 15 min. Proliferation was induced by the addition of 2 µM Phytohemagglutinin at 37° C. in an atmosphere containing 95% $CO_2$. Viability was determined after 48 h using an 3-(4,5-Dimethylthiazol-2-yl)-2,5-diphenyltetrazolium bromide (MTT) assay. Data were analysed using GraphPad Prism. percent inhibition and/or $GI_{50}$ values for each compound were determined based on the percent inhibition due to the test compound compared to the control. For instance example 29, 42 & 75 showed a greater than 70% inhibition when tested at 10 uM.

b. Inhibition of PHA Induced Cytokine (IL17) Release:

PBMC from freshly collected HWB were isolated by density gradient using Histopaque and seeded in a 96-well plate. Wells were incubated with desired concentrations of the inhibitor for 15 min. Proliferation was induced by the addition of 2 µM Phytohemagglutinin at 37° C. in an atmosphere containing 95% $CO_2$. Supernatant was collected after 48 h for estimation of cytokines by ELISA. Data were analysed using GraphPad Prism. Percent inhibition and $IC_{50}$ values for each compound were determined based on the percent inhibition due to the test compound compared to the control. For instance example 5 showed a greater than 50% inhibition when tested at 10 uM.

c. Inhibition of PHA Induced CD4+ Cell Proliferation in Human Whole Blood:

HWB or were treated with desired concentration of inhibitor and induced with 5 µM PHA. % CD4+ cell viability was determined after 48 h by flow cytometry. Data were analysed using GraphPad Prism. Percent inhibition and $IC_{50}$ values for each compound were determined based on the percent inhibition due to the test compound compared to the control. For instance example 29 and 75 showed a greater than 65% inhibition when tested at 1 uM.

d. Inhibition of PHA Induced CD4+ Cell Proliferation in PBMC:

Isolated PBMC were treated with desired concentration of inhibitor and induced with 5 µM PHA. % CD4+ cell viability was determined after 48 h by flow cytometry. Data were analysed using GraphPad Prism. $IC_{50}$ values for each compound were determined based on the percent inhibition due to the test compound compared to the control. For instance example 29 and 75 showed a greater than 90% inhibition when tested at 1 uM.

5. Single Dose Oral Hepatotoxicity Assay:

BALB/cJ (n=4 or 5/sex) mice aged 8 to 10 weeks, with weights ranging from 18 to 25 g were used. They were housed under conditions of controlled temperature and humidity and a 12-h light/dark cycle. They were given continuous access to bottled spring water and fed a standard chow at ad libitum. The mice were allowed to acclimate for 1 week before use. On the day of experiment mice were fasted overnight for 12 h and administered with test item formulation (100 mg/kg·b·wt/po) or vehicle (10 ml/kg·b·wt/po) by oral route and food was given 4 hr after test item administration. After 24 hr post administration blood samples were collected from orbital sinus of all the animals and serum was separated to assess the hepatotoxicity. Biochemical evaluation of liver function was determined by measuring serum enzyme activities of alanine aminotransferase (ALT) and aspartate aminotransferase (AST) using commercially available kits from Sigma (St. Louis, Mo.).

Results:

The compounds of the invention were found to be Non-Hepatotoxic and the data is as disclosed herein below in Table-4.

| Group | Total number of animals (n) | AST (U/L) | ALT (U/L) | Hepatotoxic |
|---|---|---|---|---|
| Sham Control | — | 116.2 | 77.6 | NO |
| Vehicle Control | 8 | 131.1 | 60 | NO |
| Vehicle Control | 8 | 239.8 | 96.8 | NO |
| Example 5 | 8 | 137.8 | 113.6 | NO |
| Example 19 | 8 | 126.5 | 87.9 | NO |
| Example 29 | 8 | 114.4 | 67.9 | NO |
| Example 31 | 10 | 161.4 | 65.1 | NO |
| Example 35 | 8 | 172 | 108.3 | NO |
| Example 42 | 10 | 189.6 | 113 | NO |
| Example 70 | 8 | 210.4 | 84 | NO |
| Example 75 | 8 | 210.8 | 93.9 | NO |

6. Evaluation of Usefulness of DHODH Modulators in Various Anti-Inflammatory and Autoimmune Disorders Using In-Vivo Animal Models has been or can be Established Using the Methodology as Given Below.

i. Inhibition of Concanavalin Induced Lymphocyte Proliferation in Wistar Rats:

Con A is often used to prepare experimental animals with high levels of cytotoxic T-lymphocytes, because these cells are involved in the development of viral infections in humans. To evaluate the effect of an inhibitor on lymphocyte proliferation in rats, animals were treated with 10 mg/kg po of a compound of the present invention prior to intravenous administration of 5 mg/kg concanavalin A. Lymphocyte count was determined after 48 h on a Medonic blood analyzer. Data indicated a ~75% reduction in peripheral blood lymphocytes upon treatment with the test compound implicating the therapeutic potential of the compound in immune-mediated disorders such as rheumatoid arthritis.

ii. Inhibition of Concanavalin Induced IL-17 Release in Balb/c Mice:

Balb/c mice were treated with 10 mg/kg po of the test compound prior to intravenous administration of 20 mg/kg concanavalin A. Plasma was obtained after 2 h and estimated for inhibition of IL-17 release by ELISA. The test compound reduced IL-17 secretion from Th17 cells in a dose-dependent manner.

iii. Inhibition of TNBS Induced Colitis in Balb/c Mice:

Female BALB/c Mice are to be fasted overnight and administered PBS, 50% Ethanol/PBS, or 50% Ethanol/20 mg/kg TNBS (40 µL enema), while under isoflourane anesthesia (study day 1). Animals are to be dosed p.o. with Vehicle, Dexamethasone (5 mg/kg), or test compounds at for example 25 mg/kg. The dosing would begin on study day 1 (5 hours after the TNBS enema). Mice are to be euthanized on day 7. Various parameters of colitis are to be measured, essentially according to a previously published study (see. Fitzpatrick et al., *Inflammatory Bowel Diseases*, 2010).

Other in-vivo models wherein the effect of DHODH modulators in various Anti-inflammatory and Autoimmune disorders can be tested include Collagen-induced arthritis in male DBA/a Ola HSD mice and Chronic Experimental Autoimmune Encephalomyelitis in C57/Bl6J mice: Collagen induced arthritis in rodent models have been widely used to illustrate and understand the development of the disease besides serving as a surrogate for validation of therapeutic targets for human rheumatoid arthritis. Mice are anesthetized with Isoflurane and given 150 μl of Bovine Type II collagen in Freund's complete adjuvant injections (day 0 and day 21). Treatment is initiated on study day 0 and continued once daily, every day (po, qd). Starting on day 18, clinical scores are given daily for each of the paws (right front, left front, right rear, left rear) and continued till the day of sacrifice (day 34).

Experimental Autoimmune Encephalomyelitis (EAE) is an inflammatory disease of the central nervous system and widely used as an animal model of Multiple Sclerosis. Animals are administered pertussis toxin intravenously and myelin oligodendrocyte glycoprotein (MOG) subcutaneously on day 0. Treatment is initiated at day 0 and continued till sacrifice. Development of EAE is observed between day 9 to day 42. At the end of the treatment period, animals are sacrificed for histopathological analysis as well as cytokine estimation in plasma.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above and the appended claim.

All publications and patent and/or patent applications cited in this application are herein incorporated by reference to the same extent as if each individual publication or patent application was specifically and individually indicated to be incorporated herein by reference.

The invention claimed is:
1. A compound of formula (I)

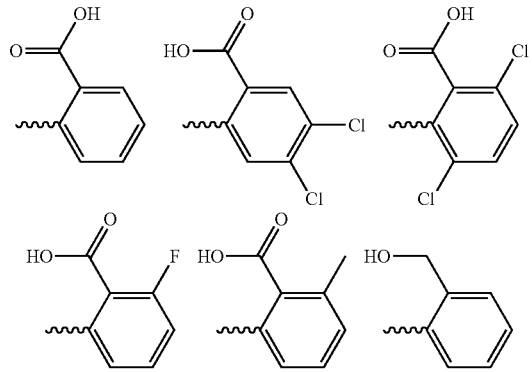

or a tautomer, stereoisomer, pharmaceutically acceptable salt, pharmaceutically acceptable ester, or N-oxide thereof, wherein Ring A including substituent $R^1$ is

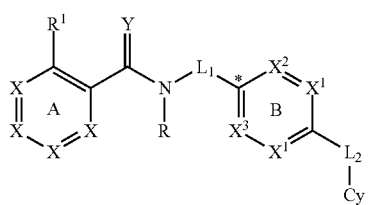

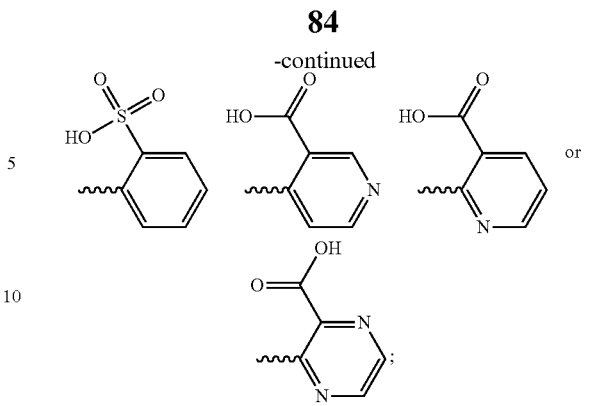

Ring B, including $X^1$, $X^2$ and $X^3$ is selected from

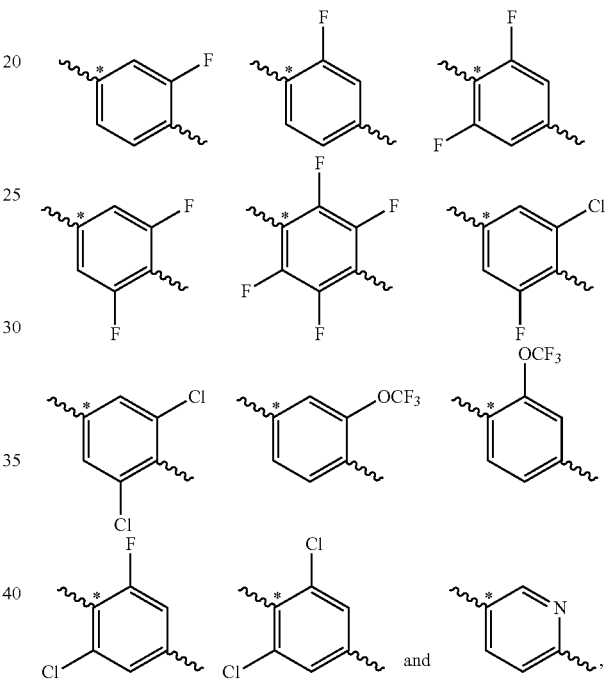

wherein Ring A and Ring B may each independently be optionally substituted by one or more $R^4$ and C* is attached to —NR—;

R is hydrogen;

$L^1$ and $L^2$ are absent;

Cy is selected from the group consisting of

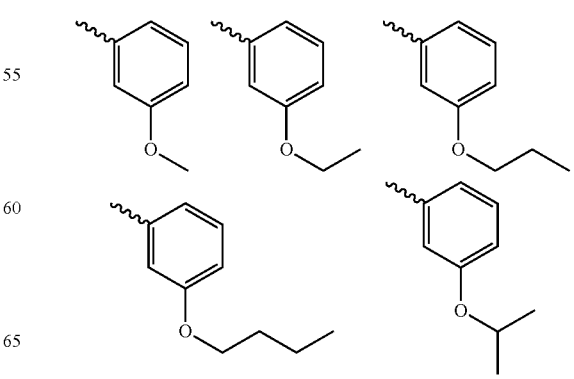

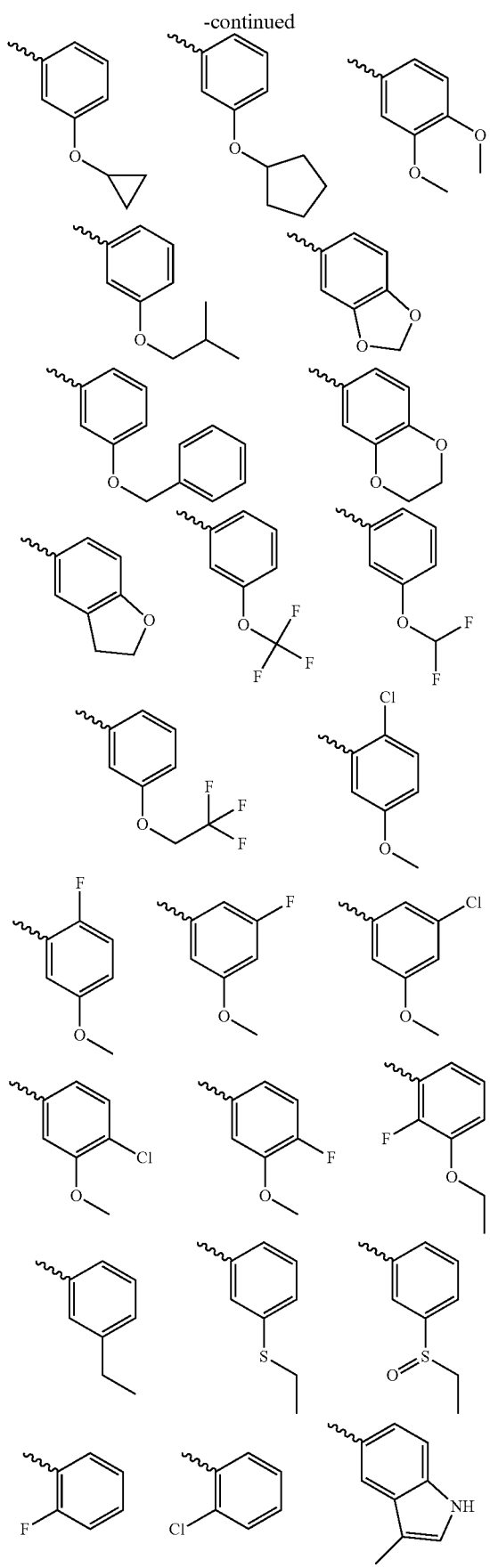

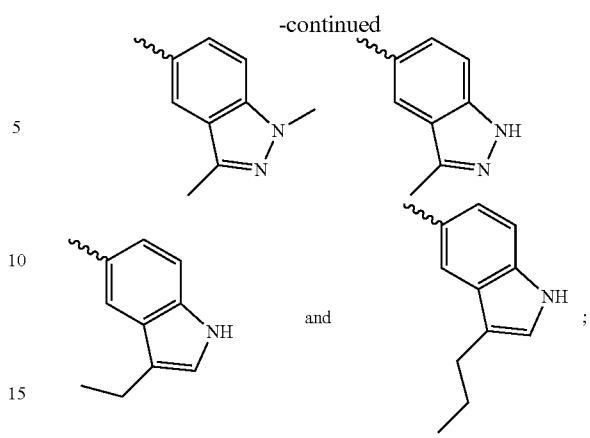

and each occurrence of $R^4$ is independently selected from the group consisting of hydrogen, hydroxy, halogen, cyano, —$OR^a$, —$S(=O)_q$—$R^a$, —$NR^aR^b$, —$C(=Y)$—$R^a$, —$C(=Y)$—$OR^a$, —$C(=Y)$—$NR^aR^b$, —$S(=O)_q$—$NR^aR^b$, substituted or unsubstituted alkyl, substituted or unsubstituted alkenyl, substituted or unsubstituted alkynyl, substituted or unsubstituted cycloalkyl, substituted or unsubstituted cycloalkylakyl, and substituted or unsubstituted cycloalkenyl;

each occurrence of $R^a$ and $R^b$ may be the same or different and are independently selected from the group consisting of hydrogen, halogen, hydroxy, cyano, substituted or unsubstituted $(C_{1-6})$alkyl, and —$OR^c$ (wherein $R^c$ is substituted or unsubstituted $(C_{1-6})$alkyl);

each occurrence of Y is independently selected from the group consisting of O, S and $NR^a$; and each occurrence of q independently represents 0, 1 or 2 wherein the term substituted refers to substitution with any one or any combination of the following substituents which may be the same or different and are selected from hydroxy, halogen, carboxyl, cyano, nitro, oxo (=O), thio (=S), unsubstituted alkyl, unsubstituted alkoxy, halo-substituted alkoxy, unsubstituted alkenyl, unsubstituted (alkynyl, unsubstituted cycloalkyl, unsubstituted cycloalkenyl, unsubstituted cycloalkylalkyl, unsubstituted cycloalkenylalkyl, unsubstituted heterocyclic ring, unsubstituted heterocycicylalkyl, unsubstituted aryl, unsubstituted arylalkyl, unsubstituted heteroaryl, unsubstituted heteroarylalkyl, unsubstituted guanidine, —$COOR^x$, —$C(O)R^x$, —$C(S)R^x$, —$C(O)NR^xR^y$, —$C(O)ONR^xR^y$, —$NR^yR^z$, —$NR^xCOR^yR^z$, —$N(R^x)SOR^y$, —$N(R^x)SO_2R^y$, —$(=N-N(R^x)R^y)$, —$NR^xC(O)OR^y$, —$NR^xC(O)R^y$—, —$NR^xC(S)R^y$, —$NR^xC(S)NR^yR^z$, —$SONR^xR^y$, —$SO_2NR^xR^y$—, —$OR^x$, —$OR^xC(O)NR^yR^z$, —$OR^xC(O)OR^y$, —$OC(O)R^x$, —$OC(0)NR^xR^y$, —$RxNR^yC(O)R^z$, —$R^xOR^y$, —$R^xC(O)OR^y$, —$R^xC(O)NR^yR^z$, —$R^xC(O)R^x$, —$R^xOC(O)R^y$, —$SR^x$, —$SOR^x$, —$SO_2R^x$, —$ONO_2$, wherein $R^x$, $R^y$ and $R^z$ in each of the above groups can be hydrogen, unsubstituted alkyl, unsubstituted alkoxy, unsubstituted alkenyl, unsubstituted alkynyl, unsubstituted cycloalkyl, unsubstituted cycloalkenyl, unsubstituted cycloalkylalkyl, unsubstituted cycloalkenylalkyl, unsubstituted heterocyclic ring, heterocycicylalkyl, unsubstituted aryl, unsubstituted arylalkyl, unsubstituted heteroaryl, unsubstituted heteroarylalkyl.

2. A pharmaceutical composition, comprising a compound of claim 1 and a pharmaceutically acceptable carrier.

3. The pharmaceutical composition of claim 2, further comprising one or more additional therapeutic agents selected from the group consisting of anti-inflammatory agents, immunosuppressive and/or immunomodulatory agents, steroids, non-steroidal anti-inflammatory agents, antihistamines, analgesics, and suitable mixtures thereof.

4. A method of inhibiting dihydroorate dehydrogenase (DHODH) activity in a mammal comprising administering to the mammal a compound of claim 1, wherein the compound inhibits DHODH activity in the mammal.

5. A compound selected from
2-(6-(3-Methoxyphenyl)pyridin-3-ylcarbamoyl)benzoic acid
2-(3'-Ethoxy-3-fluorobiphenyl-4-ylcarbamoyl)benzoic acid
2-[3-Fluoro-3'-(trifluoromethoxy)biphenyl-4-ylcarbamoyl]benzoic acid
2-[2'-Fluoro-3-(trifluoromethoxy)biphenyl-4-ylcarbamoyl]benzoic acid
2-(3-fluoro-3'-methoxybiphenyl-4-ylcarbamoyl)benzoic acid
2-(3'-ethoxybiphenyl-4-ylcarbamoyl)benzoic acid
2-[3'-(ethylthio)-2,3,5,6-tetrafluorobiphenyl-4-ylcarbamoyl]benzoic acid
2-(2'-chloro-2-fluoro-5'-methoxybiphenyl-4-ylcarbamoyl)benzoic acid
2-(3-fluoro-3'-propoxybiphenyl-4-ylcarbamoyl)benzoic acid
2-(3'-propoxybiphenyl-4-ylcarbamoyl)benzoic acid
2-[3'-(ethylthio)-2-fluorobiphenyl-4-ylcarbamoyl]benzoic acid
2-(2'-chlorobiphenyl-4-ylcarbamoyl)benzoic acid
2-(3'-methoxybiphenyl-4-ylcarbamoyl)benzoic acid
2-[3'-(trifluoromethoxy)biphenyl-4-ylcarbamoyl]benzoic acid
2-(3'-ethylbiphenyl-4-ylcarbamoyl)benzoic acid
2-(3'-butoxy-2,3,5,6-tetrafluorobiphenyl-4-ylcarbamoyl)benzoic acid
2-(3'-butoxy-3-fluorobiphenyl-4-ylcarbamoyl)benzoic acid
2-(3'-cyclopropoxy-3-fluorobiphenyl-4-ylcarbamoyl)benzoic acid
2-(3'-cyclopropoxybiphenyl-4-ylcarbamoyl)benzoic acid
2-(3'-butoxybiphenyl-4-ylcarbamoyl)benzoic acid
2-(3'-butoxy-2-fluorobiphenyl-4-ylcarbamoyl)benzoic acid
2-[2,6-Difluoro-4-(3-propyl-1H-indol-5-yl)phenylcarbamoyl]benzoic acid
2-[2-Chloro-4-(3-ethyl-1H-indol-5-yl)-6-fluorophenylcarbamoyl]benzoic acid
and pharmaceutically acceptable salts thereof.

6. A pharmaceutical composition, comprising a compound of claim 5 and a pharmaceutically acceptable carrier.

7. The pharmaceutical composition of claim 6, further comprising one or more additional therapeutic agents selected from the group consisting of anti-inflammatory agents, immunosuppressive and/or immunomodulatory agents, steroids, non-steroidal anti-inflammatory agents, antihistamines, analgesics, and suitable mixtures thereof.

8. A method of inhibiting DHODH activity in a mammal comprising administering to the mammal a compound of claim 5, wherein the compound inhibits DHODH activity in the mammal.

* * * * *